US010548944B1

(12) United States Patent
Jaynes et al.

(10) Patent No.: US 10,548,944 B1
(45) Date of Patent: Feb. 4, 2020

(54) ANTIMICROBIAL PEPTIDES AND METHODS OF USING THE SAME

(71) Applicant: Riptide Bioscience, Inc., Vallejo, CA (US)

(72) Inventors: Jesse Jaynes, Auburn, AL (US); L. Edward Clemens, Sacramento, CA (US); Henry Willfred Lopez, Napa, CA (US); George R. Martin, Rockville, MD (US); Kathryn Woodburn, Saratoga, CA (US)

(73) Assignee: Riptide Bioscience, Inc., Vallejo, CA (US)

( * ) Notice: Subject to any disclaimer, the term of this patent is extended or adjusted under 35 U.S.C. 154(b) by 0 days.

(21) Appl. No.: 16/165,727

(22) Filed: Oct. 19, 2018

(51) Int. Cl.
| | |
|---|---|
| C07K 7/08 | (2006.01) |
| C07K 14/00 | (2006.01) |
| A61K 38/10 | (2006.01) |
| A61K 9/00 | (2006.01) |
| A61P 31/10 | (2006.01) |
| A61K 45/06 | (2006.01) |
| A61P 31/04 | (2006.01) |
| A61K 38/16 | (2006.01) |

(52) U.S. Cl.
CPC ............ *A61K 38/10* (2013.01); *A61K 9/0014* (2013.01); *A61K 9/0053* (2013.01); *A61K 9/0073* (2013.01); *A61K 38/16* (2013.01); *A61K 45/06* (2013.01); *A61P 31/04* (2018.01); *A61P 31/10* (2018.01); *C07K 7/08* (2013.01); *C07K 14/00* (2013.01)

(58) Field of Classification Search
None
See application file for complete search history.

(56) References Cited

U.S. PATENT DOCUMENTS

| | | | |
|---|---|---|---|
| 5,717,064 A | 2/1998 | Julian et al. | |
| 5,861,478 A | 1/1999 | Jaynes | |
| 5,962,410 A | 10/1999 | Jaynes | |
| 6,255,282 B1 | 7/2001 | Jaynes | |
| 6,514,581 B1 | 2/2003 | Jaynes | |
| 6,559,281 B1 | 5/2003 | Jaynes | |
| 6,635,740 B1 | 10/2003 | Enright | |
| 7,566,777 B2 | 7/2009 | Enright | |
| 7,803,755 B2 * | 9/2010 | Jaynes ................... | A61K 38/02 424/61 |
| 8,258,100 B2 | 9/2012 | Enright | |
| 8,569,230 B2 * | 10/2013 | Yount ................... | C07K 14/521 514/2.3 |
| 8,734,775 B2 | 5/2014 | Yates-Binder | |
| 9,090,655 B2 | 7/2015 | Cheng et al. | |
| 9,492,499 B2 | 11/2016 | Jaynes | |
| 10,016,480 B2 | 7/2018 | Rudloff | |
| 10,017,542 B2 * | 7/2018 | Jaynes ................... | A61K 45/06 |
| 2002/0155132 A1 | 10/2002 | Jaynes | |

| | | | |
|---|---|---|---|
| 2004/0018967 A1 | 1/2004 | Enright | |
| 2005/0187151 A1 | 8/2005 | Strom | |
| 2008/0153748 A1 | 6/2008 | Jaynes | |
| 2010/0016227 A1 | 1/2010 | Enright | |
| 2012/0270770 A1 | 10/2012 | Jaynes | |
| 2014/0128312 A1 | 5/2014 | Jaynes | |
| 2014/0329753 A1 | 11/2014 | Jaynes | |
| 2016/0296594 A1 * | 10/2016 | Jaynes ................... | A61K 45/06 |
| 2017/0020956 A1 | 1/2017 | Jaynes | |

FOREIGN PATENT DOCUMENTS

| | | |
|---|---|---|
| WO | WO90/12866 | 11/1990 |
| WO | WO93/03749 | 3/1993 |
| WO | WO95/28832 | 11/1995 |
| WO | WO96/03519 | 2/1996 |
| WO | WO96/03522 | 2/1996 |
| WO | WO98/42634 | 10/1998 |
| WO | WO00/73433 | 12/2000 |
| WO | WO2004/033715 | 4/2004 |
| WO | WO2005/046714 | 5/2005 |
| WO | WO2012/050892 | 4/2012 |

OTHER PUBLICATIONS

Muta et al. ("Tachyplesins Isolated from Hemocytes of Southeast Asian Horseshoe Crabs (*Carcinoscorpis rotundicauda* and *Tachypleus gigas*): Identification of a New Tachyplesin, Tachyplesin III, and a Processing Intermediate of its Precursor", J. Biochem.,1990, 261-266 (Year: 1990).*
U.S. Appl. No. 15/286,491, filed Oct. 5, 2016, Jaynes.
U.S. Appl. No. 16/000,709, filed Jun. 5, 2018, Jaynes.
U.S. Appl. No. 16/116,619, filed Aug. 29, 2018, Jaynes.
Partial Supplementary European Search Report from European Application No. EP15851584, dated May 30, 2018, 17 pages.
Blondell, S. et al. "Optimization and High-Throughput Screening of Antimicrobial Peptides," Current Pharmaceutical Design, vol. 16, No. 28, Sep. 1, 2010, pp. 3204-3211.
Clemens, Edward L. et al. "Designed Host Defense Peptides for the Treatment of Bacterial Keratitis", Investigative Ophthalmology & Visual Science, vol. 58, No. 14, Dec. 14, 2017, p. 6273.
Jankowski et al. "Anti-inflammatory effect of oxytocin in rat myocardial infarction," Basic Res Cardiol., (2010) 105(2):205-18.
Jaynes et al. "Structure/Function Link Between Cytokine Domains and Natural and Designed Lytic Peptides: Medical Promise," (2012) American Chemical Society, pp. 21-45.
Ko et al. "Folfirinox: A Small Step or a Great Leap Forward?" Journal of Clinical Oncology, vol. 29 No. 28, Oct. 1, 2011, pp. 3727-3729.
Oxytocin, NCBI, PRF:229114, GI:229114 (Jul. 10, 1992), 1 page, also available at http://www.ncbi.nlm.nig.gov/protein/229114 (last visited Jan. 28, 2016).
Park et al. "Melittin Inhibits Inflammatory Target Gene Expression and Mediator Generation Via Interaction With kappaB Kinase," Biochemical Pharmacology, Sep. 29, 2006, vol. 73, No. 2, pp. 237-247.

(Continued)

*Primary Examiner* — Lianko G Garyu
(74) *Attorney, Agent, or Firm* — Bret E. Field; Bozicevic, Field & Francis LLP

(57) ABSTRACT

Aspects of the present invention relate to peptides having antimicrobial activity. In certain aspects, the invention relates to peptides having potent antimicrobial activity, broad-spectrum antimicrobial activity, and/or the ability to kill otherwise antibiotic-resistant microbes, or microbes protected by biofilms.

23 Claims, 9 Drawing Sheets

Specification includes a Sequence Listing.

(56) References Cited

OTHER PUBLICATIONS

Raventos, D. et al. "Improving on Nature's Defenses: Optimization & High Throughput Screening of Antimicrobial Peptides," Current Topics in Medicinal Chemistry, Bentham Science Publishers Ltd, vol. 8, No. 2, May 1, 2005, pp. 219-233.
Smith et al. "Effects of Synthetic Amphiphilic α-Helical Peptides on the Electrochemical and Structural Properties of Supported Hybrid Bilayers on Gold," Langmuir, vol. 22(4):1919-1927 (Jan. 20, 2006).
Wang et al. "A Cell-Penetrating Peptide Suppresses Inflammation by Inhibiting NF-Kappa-Beta Signaling," Molecular Therapy, May 10, 2011, vol. 19, No. 10, pp. 1849-1857.
Water, from http://www.biologyOnline.org/dictionary/Water, pp. 1-3, accessed Apr. 24, 2014.
Sawabe, T. et al., Hypothetical Protein JCM19233_786 [*Vibrio* sp. C7], Genbank entry [online], Oct. 17, 2014 [retrieved on Dec. 14, 2018], <URL: https://www.ncbi.nlm.nih.gov/protein/GAL09809.1>, p. 1.
Panda, et al., Hypothetical Protein KCO_01177 [*Pectobacterium carotovorum* subsp. *brasiliensis* ICMP 19477], Genbank entry [online], Jun. 24, 2015 [retrieved on Dec. 14, 2018], <URL: https://www.ncbi.nlm.nih.gov/protein/KMK85879.1>, pp. 1-2.

\* cited by examiner

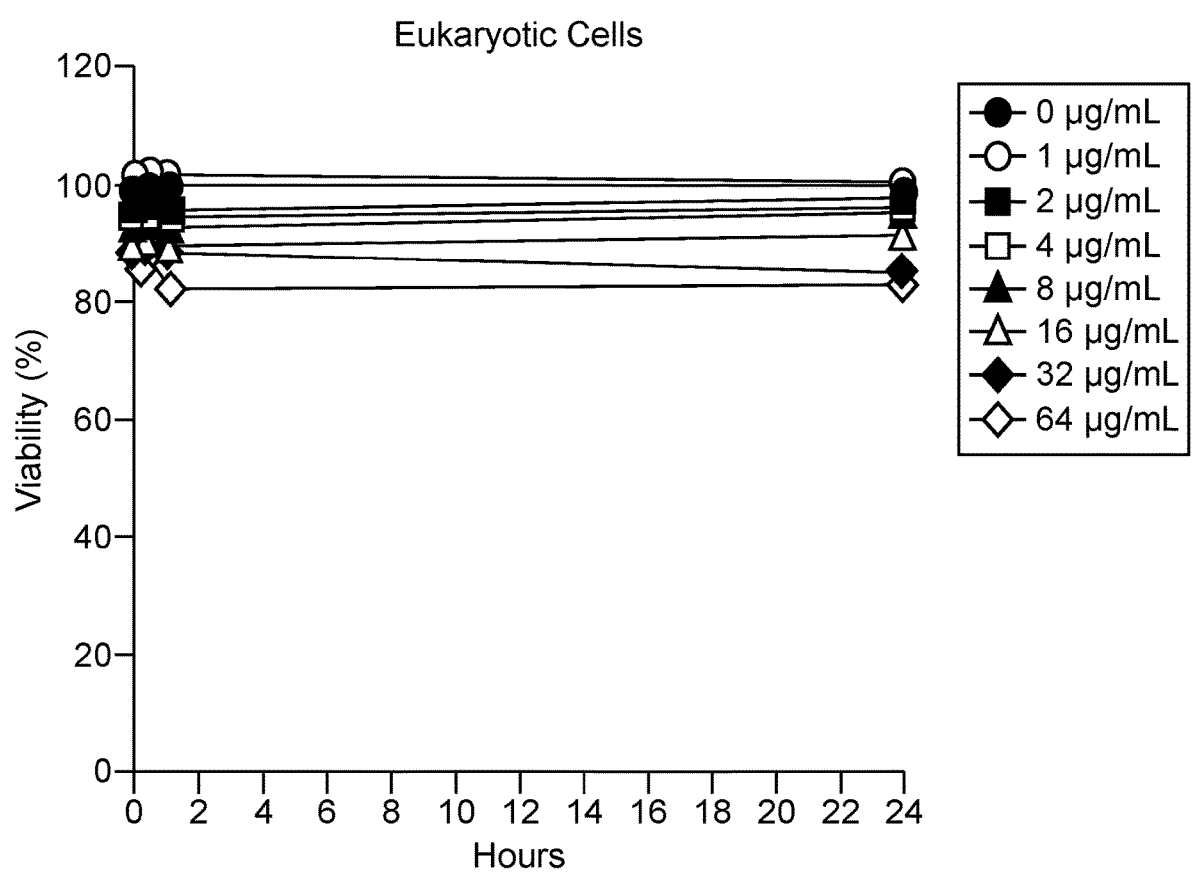

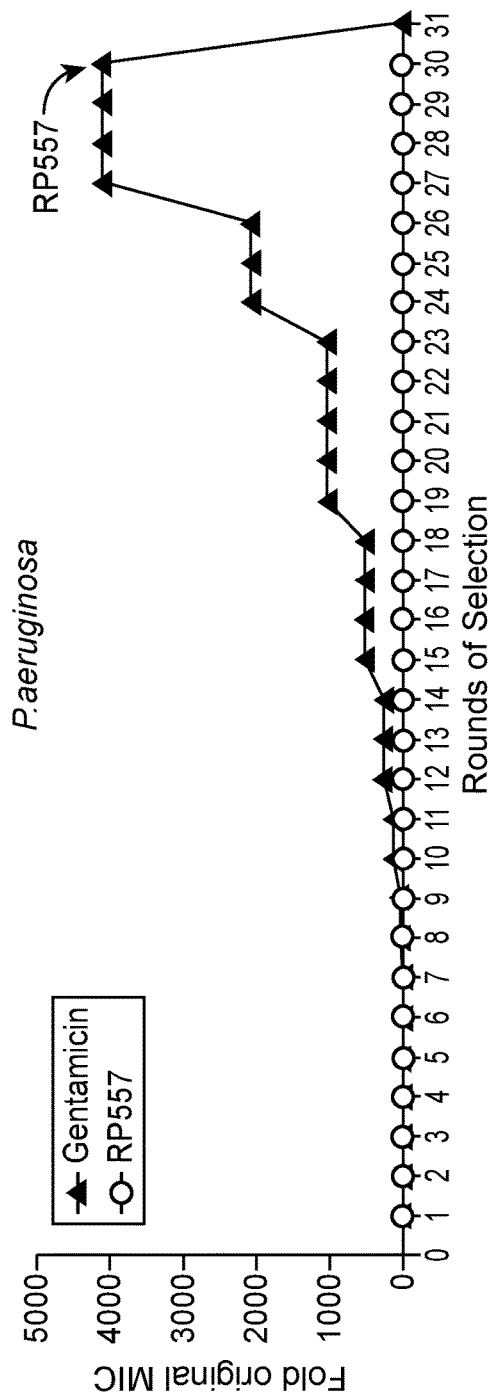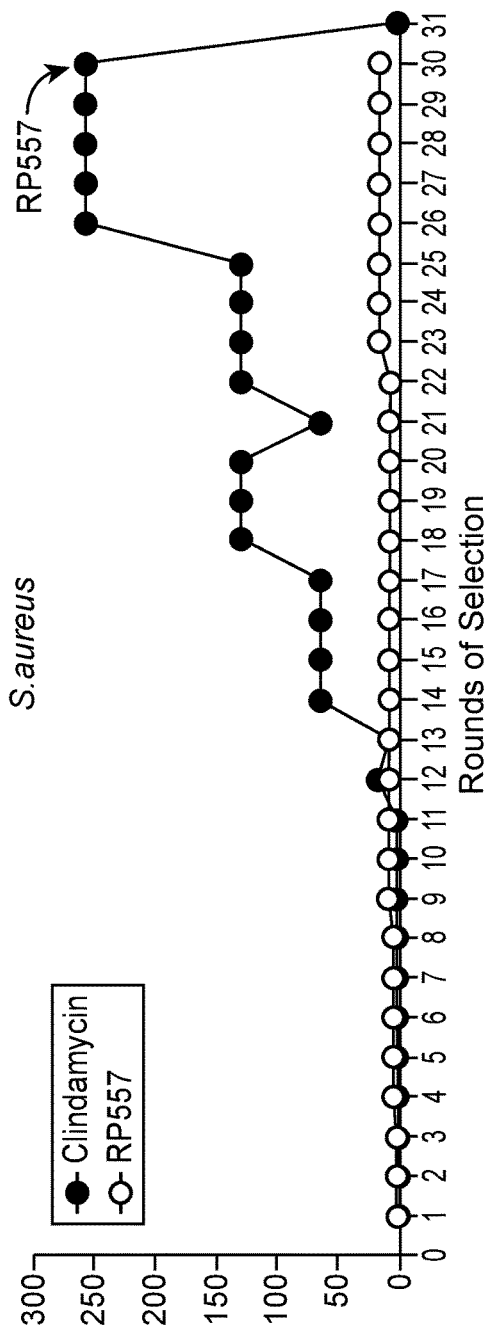

US 10,548,944 B1

ANTIMICROBIAL PEPTIDES AND METHODS OF USING THE SAME

GOVERNMENT RIGHTS

This invention was made with Government support under contract 1R434EY024463-01 awarded by the National Institutes of Health and contract DM140274 awarded by the Department of Defense. The Government has certain rights in the invention.

FIELD OF THE INVENTION

The technology disclosed and claimed below relates generally to peptides having antimicrobial activity. More particularly, the invention relates to peptides having potent antimicrobial activity, broad spectrum anti-bacterial activity, and/or the ability to kill otherwise antibiotic-resistant bacteria, or bacteria protected by biofilms.

INTRODUCTION

Antibiotic resistance is a major health problem. This is attributed in part to the widespread use of antibiotics not only in medicine, but also in agriculture and animal husbandry. Such overuse of antibiotics, while killing susceptible organisms, has also created a powerful selection bias toward antibiotic resistant bacteria. The resulting antibiotic resistant strains pose a particular problem for individuals with weakened immune systems and represent an increasingly serious problem for patients in hospitals. Acute bacterial skin and skin structure infections (ABSSSI) are responsible for 750,000 hospitalizations per year at substantial cost. Broad-spectrum coverage for gram-negative pathogens and multi-drug-resistant gram-positive bacteria, such as community-acquired methicillin resistant *Staphylococcus aureus* (MRSA) strains are limited and frequent outbreaks occur.

In addition to exhibiting inherited antibiotic resistance, many emerging bacterial strains can exist in complex associations known as biofilms, densely packed communities of microbial cells that can grow on living or inert surfaces and surround themselves with secreted polymers. The structure of a biofilm constitutes a physical barrier to antibiotic exposure. Biofilms are 20-1000 times more resistant to antibiotics than their planktonic counterparts and can form in and on tissues, particularly on chronic wounds and medical implants, such as indwelling catheters, artificial organs, and the like, where they have the potential to cause systemic infections requiring heroic treatments. There is an urgent need for materials that are active against antibiotic resistant organisms in both free and biofilm form.

As part of their natural defense against bacteria, many organisms including insects, amphibians, mammals, and humans, produce antimicrobial peptides. Such peptides are chemically diverse. Some antimicrobial peptides appear to act by penetrating the bacterial cell membrane and destroying it. Other antimicrobial peptides affect bacterial cellular processes. Considerable selectivity is observed, with many of the peptides targeting bacteria in preference to host cells. Unfortunately, host-produced antimicrobial peptides are generally not capable of effectively eliminating a wide range of microbial agents, including many antibiotic resistant bacterial strains. Antimicrobial peptides having potent antimicrobial activity, broad spectrum anti-bacterial activity, and/or the ability to kill otherwise antibiotic-resistant bacteria are of interest.

SUMMARY

The invention provides antimicrobial peptides and methods of using the same. The peptides of this disclosure can have anti-bacterial, anti-fungal, and/or anti-protozoal activity. The peptides can kill microbial strains that are resistant to conventional antibiotics. This disclosure provides antimicrobial peptides that are capable of killing microbes (e.g., bacteria) growing as a microbial biofilm. The technology described and claimed below represents the first description of particular types of antimicrobial peptides that can be used a variety of applications, e.g., to selectively kill microbes (e.g., bacteria) for purposes of treatment of conditions related to microbial infections.

The invention is put forth in the description that follows, in the figures, and in the appended claims.

BRIEF DESCRIPTION OF THE DRAWINGS

FIG. 2A depicts a monomeric version of the peptide where cysteine residues located in the amphipathic regions may be linked via an intramolecular disulfide bond. FIG. 2B depicts a dimeric version of the peptide where the two cysteine residues may be linked via an intermolecular disulfide bond.

FIG. 3A to 3C shows RP557 rapidly eradicates *P. aeruginosa* and *S. aureus* with no cytotoxicity to mammalian cells. Cell viability was performed using bioluminescent strains of *P. aeruginosa* 19660 (FIG. 3A), *S. aureus* 49525 (FIG. 3B) & L929 fibroblast cells (FIG. 3C).

FIG. 4A to 4B shows data indicating that *P. aeruginosa* and *S. aureus* did not develop resistance against RP557. Sub-inhibitory concentrations of RP557, gentamicin and clindamycin were incubated with *P. aeruginosa* 27853 and *S. aureus* 29213 for 24 hours. Bacteria showing growth in the highest concentration were re-passaged in fresh dilutions containing sub-minimum inhibitory concentration (MIC) levels of each component for 30 consecutive passages.

DETAILED DESCRIPTION

Figure 1:
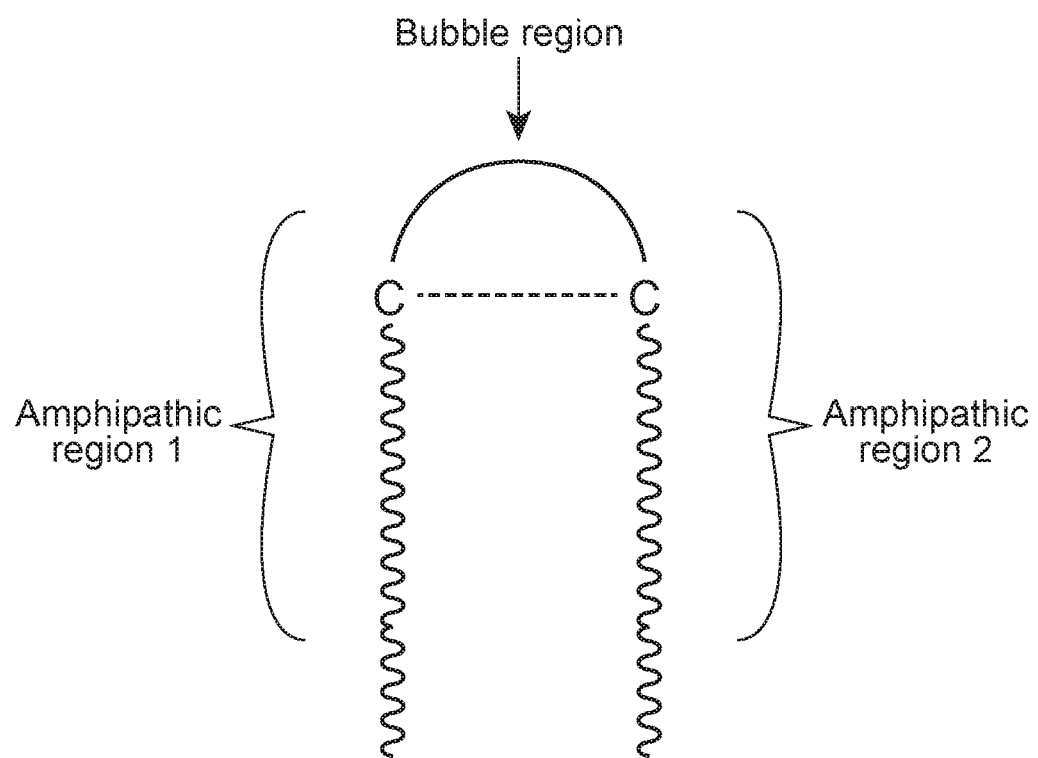
FIG. 1 depicts an exemplary bubble region-containing peptide of the disclosure. The peptide depicted includes a bubble region having a disulfide bond that is flanked by amphipathic regions 1 and 2.

As discussed above, the invention disclosed herein relates to antimicrobial peptides and methods of administering such antimicrobial peptides to a subject to prevent or treat a microbial infection.

Antimicrobial Peptides

Certain features of the antimicrobial peptides of this disclosure will now be described in more detail. The antimicrobial peptides generally include an amphipathic or striapathic region. In some cases, the peptide includes one contiguous amphipathic or striapathic region. In some cases, the peptide includes two amphipathic or striapathic regions separated by a linking region or bubble region (e.g., as described herein).

By "amphipathic region" is meant a peptide region or segment that possesses both hydrophobic and hydrophilic structural elements or characteristics, for example, a peptide region capable of possessing a structure having a hydrophilic surface and a hydrophobic surface. A peptide region is said to be amphipathic and in an amphipathic conformation when it exhibits an amphipathic characteristic. The amphipathic characteristics of a peptide can be dependent in part on the environmental conditions to which the peptide is subjected and/or utilized, e.g., aqueous conditions or physiological conditions. To be considered or referred to as amphipathic, a peptide sequence (or portion thereof) need not be in an amphipathic conformation at all times. Rather, it is sufficient that in some cases the amphipathic conformation be present, e.g., the peptide is capable of adopting an amphipathic conformation under suitable conditions, such as the conditions in which the peptide finds use.

An amphipathic region of a peptide can be referred to as a striapathic region. The term "striapathic region" refers to a region or portion of a peptide sequence that is composed of a sequence of alternating hydrophobic and hydrophilic modules. A "hydrophobic module" is a peptide sequence consisting of one to five (e.g., 1 to 3 or 1 to 2) hydrophobic amino acid residues, e.g., 1, 2, 3, 4 or 5 hydrophobic amino acid residues. A "hydrophilic module" is a peptide sequence consisting of one to five (e.g., 1 to 3 or 1 to 2) hydrophilic amino acid residues, e.g., 1, 2, 3, 4 or 5 hydrophilic amino acid residues.

Hydrophobic amino acid residues are characterized by a sidechain group that has predominantly non-polar chemical or physical properties, e.g., in an environment in which a peptide finds use, e.g., physiological conditions. Such hydrophobic amino acid residues can be naturally occurring or non-naturally occurring. A hydrophobic amino acid residue can be a mimetic of a naturally occurring amino acid that is characterized by a sidechain group that has predominantly non-polar chemical or physical properties. Conversely, hydrophilic amino acid residues are characterized by a sidechain group that is predominantly polar (e.g., charged or neutral hydrophilic), e.g., in an environment in which a peptide finds use, e.g., physiological conditions. Such hydrophilic amino acid residues can be naturally occurring or non-naturally occurring. A hydrophilic amino acid residue can be a mimetic of a naturally occurring amino acid characterized by a sidechain group that is predominantly hydrophilic (charged or neutral polar). Examples of hydrophilic and hydrophobic amino acid residues are shown in Table 1, below. The hydrophobic and hydrophilic amino acid residues can be L-amino acid residues. The hydrophobic and hydrophilic amino acid residues can be D-amino acid residues. Suitable non-naturally occurring amino acid residues and amino acid mimetics that can find use in the subject peptides are readily available in the art. See, e.g., Liang et al. (2013), "An Index for Characterization of Natural and Non-Natural Amino Acids for Peptidomimetics," PLoS ONE 8(7):e67844.

Although most amino acid residues can be considered as either hydrophobic (non-polar) or hydrophilic (polar or charged), a few, depending on the context, can behave as either hydrophobic or hydrophilic.

TABLE 1

Hydrophobic and Hydrophilic Amino Acid Residues

| Hydrophilic Residues (X) | Hydrophobic Residues (J) |
|---|---|
| lysine | phenylalanine |
| ornithine | tryptophan |
| arginine | tyrosine |
| histidine | isoleucine |
| aspartic acid | leucine |
| glutamic acid | valine |
| asparagine | methionine |
| glutamine | alanine |
| pyrrolysine | proline |
|  | glycine |
|  | cysteine |
|  | threonine |
|  | norleucine |
|  | norvaline |

As described in further detail below, aspects of the present disclosure include antimicrobial peptides having at least one amphipathic or striapathic region having a specific degree of cationic charge. In certain embodiments, the antimicrobial peptide includes a tail region (e.g., a hydrophobic tail sequence). In certain embodiments, an antimicrobial peptide (or peptide agent) includes two or more amphipathic or striapathic regions. In such embodiments, two amphipathic regions of an antimicrobial peptide are in the form of a dimer, where the two amphipathic regions can have the same or different amino acid sequences (i.e., be homodimer or a heterodimer). In certain embodiments, the two (or more) amphipathic or striapathic regions are connected via a linker or linking region. The linker can be a contiguous (or in-line) amino acid sequence or a non-amino acid moiety as desired by a user. The linking region can be, e.g., a bubble region or a beta-turn region.

In certain embodiments, an amphipathic region of a peptide is referred to as a striapathic region and includes an alternating sequence composed of 1 to 5 hydrophobic residues (a hydrophobic module $J_{1-5}$) followed by 1 to 5 hydrophilic amino acid residues (a hydrophilic module $X_{1-5}$). A striapathic region can thus be represented by the formulae $(X_{1-5}J_{1-5})_n$ or $(J_{1-5}X_{1-5})_n$, where each X signifies a hydrophilic amino acid residue, each J signifies a hydrophobic amino acid residue, and each n is an integer from 1 to 15, such as 2 to 15, 2 to 10, 3 to 10, 4 to 10 or 5 to 10. For example, an amphipathic region can have a sequence according to Formula 1, Formula 2 (the reverse of Formula 1) or Formula 3:

$X^1J^2J^3X^4X^5J^6J^7X^8X^9J^{10}X^{11}X^{12}J^{13}J^{14}X^{15}X^{16}J^{17}J^{18}$   Formula 1:

$J^1J^2X^3X^4J^5J^6X^7X^8J^9X^{10}X^{11}J^{12}J^{13}X^{14}X^{15}J^{16}J^{17}X^{18}$   Formula 2:

$J^1X^2J^3X^4J^5X^6J^7X^8J^9X^{10}J^{11}X^{12}J^{13}X^{14}J^{15}X^{16}J^{17}$   Formula 3:

Each hydrophobic amino acid residue J is selected from the group consisting of a naturally occurring hydrophobic amino acid, a non-naturally occurring hydrophobic amino acid, and a hydrophobic amino acid mimetic. Each hydrophilic amino acid residue X is selected from the group consisting of a naturally occurring hydrophilic amino acid, a non-naturally occurring hydrophilic amino acid, and a hydrophilic amino acid mimetic. Often, the amphipathic conformation will be associated with a particular secondary structure, such as a helical structure. Thus, the amphipathic region of an antimicrobial polypeptide can have an amphipathic $3_{10}$-helical conformation, an amphipathic α-helical conformation, an amphipathic π-helical conformation, or an amphipathic polyproline helical conformation. Alternatively, the amphipathic region of an antimicrobial polypeptide can have an amphipathic β-strand conformation.

In certain embodiments, the amphipathic region of an antimicrobial peptide according to aspects of the present disclosure includes one or more (e.g., 2, 3, 4, 5, 6, 7, 8, 9, 10 or more) large hydrophobic amino acid residues. Examples of large hydrophobic amino acid residues include tryptophan, phenylalanine, and tyrosine. In addition, under certain circumstances, histidine can be considered a large hydrophobic amino acid residue. In certain embodiments, the amphipathic region of an antimicrobial peptide according to aspects of the present disclosure includes one or more (e.g., 2, 3, 4, 5, 6, 7, 8, 9, 10 or more) small hydrophobic amino acid residues. Examples of small hydrophobic residues include glycine, alanine, valine, leucine, threonine, and proline. In addition, under certain circumstances serine or cysteine can be considered a small hydrophobic residue. In certain embodiments, the antimicrobial polypeptide has an amphipathic region that includes a combination of large and small hydrophobic residues.

Cationic Charge/Surface

Antimicrobial polypeptides according to aspects of the present disclosure can include an amphipathic region having a cationic surface. In certain embodiments, the amphipathic region has a cationic charge (i.e., charge >0, e.g., +1, +2, +3, +4, +5, +6, +7, +8, +9, +10 or more). Thus, in certain embodiments, an amphipathic region of the disclosed peptides contains one or more polar cationic amino acid residues (i.e., residues having positively charged side chains), such as 2 or more, 3 or more, 4 or more, or 5 or more polar cationic amino acid residues, in some cases, up to 10 polar cationic amino acid residues. Examples of amino acid residues having positively charged side groups (assuming physiological conditions) include lysine, ornithine and arginine, and sometimes histidine. Accordingly, an antimicrobial polypeptide can have an amphipathic region that includes from 1 to 20 cationic amino acid residues, such as 2 to 20, 3 to 30, 4 to 20, 5 to 20, 6 to 20, 8 to 20 or 10 to 20 cationic amino acid residues. Thus, an antimicrobial peptide of the invention can include polar amino acid residues, at least 40% (e.g., 50%, 60%, 70%, 80%, 90%, or 100%) of which are cationically charged (e.g., are selected from Arg, Lys and Orn).

Tail Region

In certain embodiments, an antimicrobial peptide includes a tail region. A tail region of an antimicrobial peptide of the invention can be from 3 to 15 amino acid residues in length, with at least 50% (e.g., at least 60%, at least 70%, at least 75%, at least 80%, at least 85%, at least 90%, or more) of the amino acid residues in the tail region being hydrophobic. The tail region can be located at either the N-terminus, the C-terminus, or both termini of the antimicrobial peptide. This disclosure provides peptides having a tail region including a sequence of 3, 4 or 5 hydrophobic amino acids. This disclosure provides peptides having a tail region including a sequence of 3-6 amino acids having one or lacking a hydrophilic amino acid residue. In certain embodiments, the tail region includes one hydrophilic amino acid for every 6 amino acids in the sequence. In some cases, a tail region sequence is shown in Formula 4, where each J signifies a hydrophobic amino acid residue (e.g., of Table 1):

$$J^1J^2J^3J^4J^5. \qquad \text{Formula 4:}$$

In some embodiments of Formula 4, $J^1$, $J^3$ and $J^5$ are independently a large hydrophobic residue (e.g., tryptophan, phenylalanine, and tyrosine), and $J^2$ and $J^4$ are independently a small hydrophobic residue (e.g., glycine, alanine, valine, leucine, threonine, and proline). In some embodiments of Formula 4, each J is independently a hydrophobic amino acid residue selected from Phe and Ala. In some cases of Formula 4, the tail region includes the sequence FAFAF (SEQ ID NO: 19). In some instances of Formula 4, the tail region includes the sequence AFAFA (SEQ ID NO: 20).

Specific examples of antimicrobial peptides according to aspects of this disclosure that include a tail region having the sequence FAFAF (SEQ ID NO: 19) include the following where the tail region is underlined:

| | |
|---|---|
| IOKFAKOFKOFIOKFAK<u>FAFAF</u> | (RP-551,SEQ ID NO: 2); and |
| <u>FAFAF</u>KAFKKAFKOFOOAFOOAF | (RP-552,SEQ ID NO: 3). |

Bubble Region

In certain embodiments, an antimicrobial peptide includes a bubble region. A "bubble" region of an antimicrobial peptide of this disclosure consists of a stretch of amino acid residues flanked by cross-linking residues (e.g., cysteine residues (C) capable of disulfide formation) at or near each end of the region (see FIG. 1A). The sequence of amino acid residues located between the flanking cross-linking residues (e.g., cysteine residues) can be from 2 to 10 amino acid residues in length. In certain cases, the stretch of amino acid residues between the cross-linking residues (e.g., cysteine residues) is from 3 to 6 amino acid residues in length, such as 3 to 5 amino acid residues in length, or in particular 3, 4 or 5 amino acid residues. A bubble region can link two amphipathic regions and contribute to the formation of a desirable hairpin secondary structure by the antimicrobial peptide. In some instances, the bubble region includes an intramolecular crosslink. Such an intramolecular crosslink, if present, can be covalent (e.g., a disulfide) or non-covalent (e.g., a salt bridge). In some cases, the bubble region includes a disulfide bond between two flanking cysteine residues (see FIG. 1A). This region can thus be classified as a type of "linker region" (as can other regions, described elsewhere herein). In certain embodiments, the hairpin secondary structure can significantly enhance antimicrobial activity.

A bubble region can include a two cysteine residues linked via a sequence of any 4 amino acids, e.g., a sequence $C(AA^1)AA^2)(AA^3)(AA^4)C$. Optionally, the cysteine residues of the bubble region may be linked to the adjacent stripathic regions of the peptide by a linker, such as one or more linking residues. In some cases, the one or more linking residues are glycine residue(s), e.g., a sequence $(G)_nC(AA^1)AA^2)(AA^3)(AA^4)C(G)_m$ where n and m are independently 0-6, such as 0, 1, 2, 3 or 4.

A bubble region can include, for example, a sequence as shown in Formula 5, where each J signifies a hydrophobic amino acid residue and each X signifies a hydrophilic amino acid residue:

C(J/X)(J/X)(J/X)(J/X)C.                        Formula 5:

In some instances of Formula 5, the bubble region has the sequence:

CJ(X/J)(X/J)JC                                   Formula 5b:

In some instances of Formula 5b, the bubble region has one of the following sequences:

CJGXJC                                           Formula 5c:

CJXGJC                                           Formula 5d:

CJGGJC.                                          Formula 5e:

In some instances of Formula 5c-5e, each J is selected from F, L, I, V and A. In some instances of Formula 5c-5d, X is selected from K, R and O.

Specific examples of antimicrobial peptides of this disclosure that include a bubble region having the sequence CLGRFC (SEQ ID NO: 21) or CYKGIC (SEQ ID NO: 22) include (the bubble region is underlined):

FKIOARL<u>CLGOFC</u>IOARLK      (RP-550,SEQ ID NO: 1); and

RFCWKV<u>CYKGIC</u>FKKCK      (RP-557,SEQ ID NO: 8).

In some embodiments antimicrobial peptides of the invention include a bubble region, and one or more additional linked regions. In certain embodiments, antimicrobial peptides of the invention that include a bubble region also include one or more additional stretches of amino acid residues flanked by cysteine residues positioned on either side of the bubble region. For example, a subject antimicrobial peptide may include four cysteine residues, with two cysteine residues forming a bubble region and the remaining two cysteine residues being positioned on opposing sides of the two amphipathic regions either side of the bubble region so as to form an additional linked region across the secondary hairpin structure (see FIG. 1B). Specific examples of antimicrobial peptides of the invention that include a bubble region having the sequence CYKGIC (SEQ ID NO: 22) and include an additional linked region include (the bubble region and additional linked region is underlined):

RW<u>CFKVCYKGIC</u>YKKCK      (RP-556,SEQ ID NO: 7)

RF<u>C̄WKVCYKGIC</u>FKKCK      (RP-557,SEQ ID NO: 8)

Dimerization

Figure 2A:
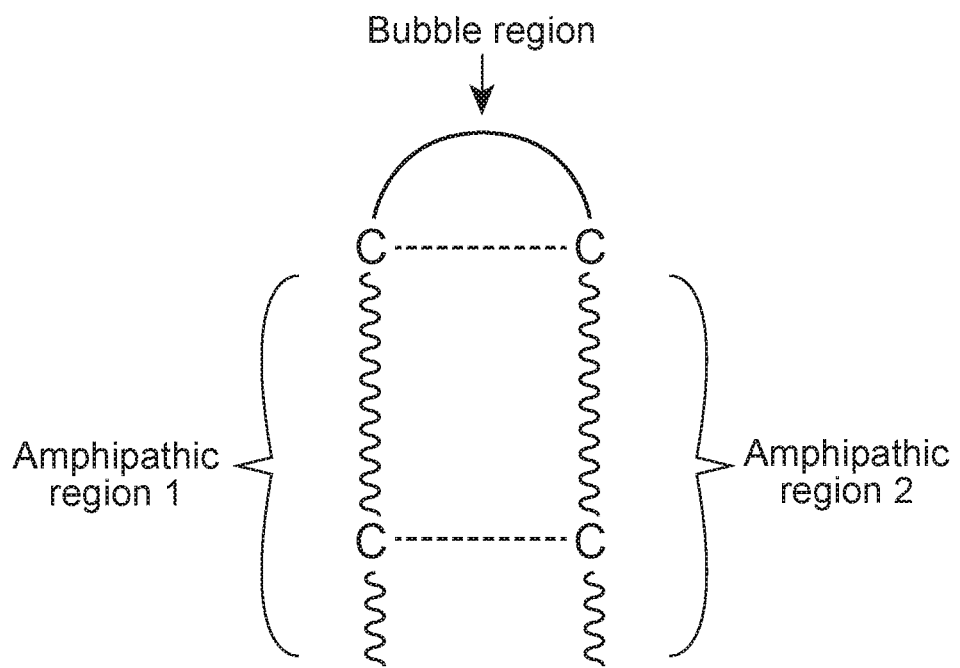
FIG. 2A and FIG. 2B depict peptides including a cysteine-containing bubble region flanked by two amphipathic regions that themselves include additional cysteine residues.
Figure 2B:
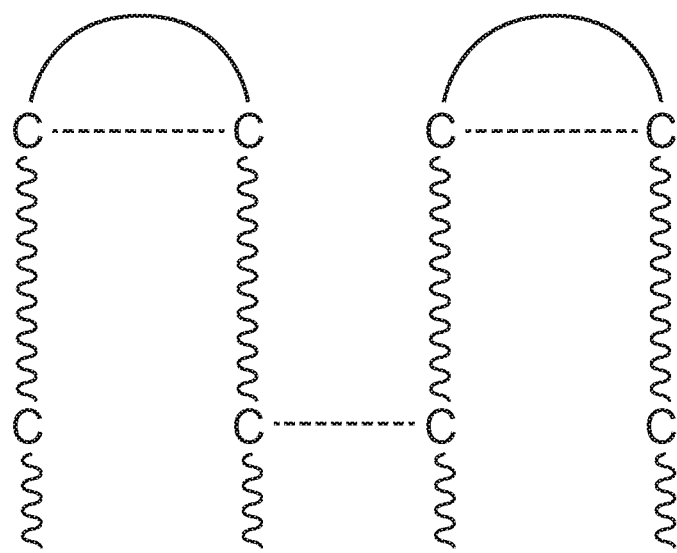

Without intending to be limited by theory, in some cases, efficacy of the antimicrobial peptides of the invention depends, in part, on peptide dimerization and clustering on the cell membrane of the target microbe (e.g., bacterial cell). It is believed that dimers can be efficient at penetrating and, ultimately, lysing the cell membrane. The formation of such dimers can be thermodynamically more favorable when the peptides are physically linked together, e.g., using linker regions or cross-linking amino acid residues. See FIG. 2B. Linker regions can include additional amino acid residues (e.g., like the bubble region described above) or be non-amino acid-containing linker moieties.

Beta Turn Region

A β-turn sequence can be used to physically link two regions, making intra-molecular interactions more likely to take place. This appears to be particularly important for amphipathic lytic peptides, as it allows their hydrophobic surfaces to be protected from the aqueous phase. A bubble region (e.g., as described here) can provide for a similar configuration. The β-turn sequence allows for two intra-chain amphipathic regions to form a dimer in an antiparallel orientation. This region can thus be classified as a type of "linker region" (as can other regions, described elsewhere herein).

A β-turn sequence that finds use in linking two striapathic regions can be any β-turn sequence known in the art. A β-turn sequence can have, for example, a sequence as shown in SEQ ID NO: 23, where J signifies hydrophobic amino acid residues and X signifies hydrophilic amino acid residues (i.e., any amino acid residue).

(J/X)GPGR(J/X)                            (SEQ ID NO: 23)

Exemplary antimicrobial peptide sequences are described below that include one or more of the features described above. Additional peptides of this disclosure can be readily designed by one skilled in the art by combining different regions or features of the exemplary antimicrobial peptides in different ways as described herein.

Examples of Antimicrobial Peptides

Particular antimicrobial peptides of interest, and fragments and variants thereof which find use in the subject pharmaceutical compositions and methods are now described in greater detail. In certain cases, the subject antimicrobial peptides are of 10 to 50 amino acid residues in length, such as 10 to 40, 10 to 30, 10 to 20, or 12 to 30, 13 to 30, 14 to 30, 15 to 30, 15 to 25, 15 to 20, 15 to 19, or 17 to 30, 17 to 25, or 17 to 20 amino acid residues in length. The subject peptide can comprise a striapathic region of alternating hydrophilic and hydrophobic modules that adopts an amphipathic conformation under physiological conditions (e.g., as described herein). In certain instances, the striapathic region of a peptide is of 5 to 30 amino acid residues in length, such as 5 to 25, 5 to 20, 5 to 19, 6 to 18, 6 to 17, 7 to 18 amino acid residues in length (e.g., 5, 6, 7, 8, 9, 10, 11, 12, 13, 14, 15, 16, 17, 18, 19 or 20 amino acids in length). The striapathic region can comprise: 2 or more (e.g., 3 or more, 4 or more, 5 or more, or 6 or more) hydrophobic modules; and one or more (e.g., 3 or more, 4 or more, 5 or more, or 6 or more) hydrophilic modules. In some cases, each hydrophilic module includes at least one cationic residue. In some instances, the peptide has one and only one striapathic region of 10 to 30 amino acid residues in length, such as 12 to 30, 15 to 25 or 10 to 20 or 15 to 20 amino acid residues in length (e.g., 15, 16, 17, 18, 19 or 20 amino acid residues in length). In some instances, the peptide has two striapathic regions linked via a bubble region or linking region, where each striapathic region is independently 5 to 15 amino acid residues in length, such as 5 to 12, 5 to 10, or 6 to 12 or 6 to 10 amino acid residues in length (e.g., 5, 6, 7, 8, 9 or 10 amino acid residues in length).

In certain instances, a striapathic region of the peptide is of 5 to 30 amino acid residues in length (e.g., 6 to 20, 6 to 19, 7 to 19, 14, 15, 16, 17, 18 or 19 amino acids in length), wherein the peptide is optionally further modified (e.g., as described herein). The striapathic region can comprise: 2 or more (e.g., 3 or more or 4 or more) hydrophobic modules; and one or more (e.g., 2 or more or 3 or more) hydrophilic modules each comprising at least one cationic residue. In some instances, the striapathic region of the peptide has a length of 7 to 20 amino acid residues.

The hydrophobic modules can consist of any convenient residues. In certain instances, the hydrophobic modules include amino acid residues selected from phenylalanine, tryptophan, alanine, valine, glycine, isoleucine, leucine, cysteine and tyrosine. The striapathic region can include 2 or more cationic amino acid residues in total, such as 3 or more, 4 or more, 5 or more, 6 or more, 7 or more, 8 or more, 9 or more, or even more. The antimicrobial peptide can include a striapathic region comprising 3 or more hydrophilic modules that consist of any convenient hydrophilic residues. In some instances, the hydrophilic modules include amino acid residues selected from lysine, arginine, histidine, aspartic acid, glutamic acid, asparagine, glutamine and ornithine. In certain instances, the hydrophilic modules include amino residues selected from lysine, arginine and ornithine.

In certain embodiments, the antimicrobial peptide comprises three or more hydrophilic modules (such as 3, 4, 5 or 6, or more) and three or more hydrophobic modules (such as 3, 4, 5 or 6, or more) and is a peptide of Formulae 1 or 2. Formulae 1 and 2 can be represented as follows to show the hydrophilic and hydrophobic modules:

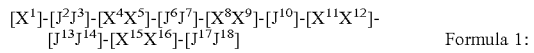

Formula 1:

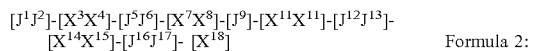

Formula 2:

wherein, each X is independently a hydrophilic amino acid residue (e.g. lysine, arginine, histidine, aspartic acid, glutamic acid, asparagine, glutamine or ornithine); and each J is independently a hydrophobic residue (e.g. phenylalanine, tryptophan, alanine, valine, glycine, isoleucine, leucine, or tyrosine). It is understood that, in some cases, an antimicrobial peptide of Formula 1 has a sequence which can be reversed to provide an antimicrobial peptide having a sequence of Formula 2.

In some cases of formula 1, each X is independently selected from arginine, lysine and ornithine. In some cases of formula 1, each X is independently selected from lysine and ornithine. In some cases of formula 1, each J is independently selected from phenylalanine, alanine, isoleucine, leucine and valine. In some cases of formula 1, each J is independently selected from phenylalanine and alanine. In some cases of formula 2, each X is independently selected from arginine, lysine and ornithine. In certain cases of formula 2, each X is independently selected from lysine and ornithine. In some cases of formula 2, each J is independently selected from phenylalanine, alanine, isoleucine, leucine and valine. In some cases of formula 2, each J is independently selected from phenylalanine, alanine and isoleucine. In some cases the antimicrobial polypeptide of formulae 1 or 2 includes one or more additional hydrophilic or hydrophobic residues at the C terminal or the N terminal. In some cases, the antimicrobial polypeptide of formulae 1 or 2 includes a tail region (e.g., as described herein) at the C terminal or the N terminal.

Formula 3 Peptides

In some embodiments, the antimicrobial polypeptide comprises a sequence defined by the formula 3 in which each residue in the sequence alternates between a hydrophobic residue (J) and a hydrophilic residue (X):

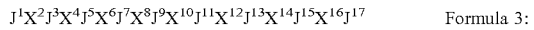

Formula 3:

wherein, each X is independently a hydrophilic amino acid residue; and each J is independently a hydrophobic residue.

In some cases of formula 3, each X is independently selected from lysine, arginine, histidine, aspartic acid, glutamic acid, asparagine, glutamine and ornithine. In some cases of formula 3, each X is independently selected from ornithine, lysine and arginine. In some cases of formula 3, each X is independently selected from ornithine and lysine. In some cases of formula 3, each J is independently selected from phenylalanine, tryptophan, alanine, valine, glycine, isoleucine, leucine and tyrosine. In some cases of formula 3, each J is independently selected from phenylalanine, alanine, isoleucine, leucine and valine. In certain cases of formula 3, the antimicrobial polypeptide includes one or more additional hydrophilic or hydrophobic residues at the C terminal and/or the N terminal. In some cases of formula 3, the antimicrobial peptide includes a tail region (e.g. as described herein) at the C terminal and/or the N terminal.

In some embodiments of the antimicrobial polypeptide of formula 3, the sequence has a formula defined by the formula 3A:

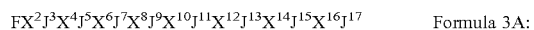

Formula 3A:

wherein:
$X^2$ and $X^{14}$ are each independently selected from O and R;
$J^3$ and $J^{17}$ are each independently selected from L and I;
$X^4$ and $X^{16}$ are each independently selected from K and O;
$J^5$ is selected from A and I;
$X^6$, $X^8$, $X^{10}$ and $X^{12}$ are each independently selected from R, K and O;
$J^7$ is selected from F, A and I;
$J^9$ is selected from V and L;
$J^{11}$ is selected from A, V and L;
$J^{13}$ is selected from A, I and L; and
$J^{15}$ is selected from I, F and L.

In some instances of formula 3A, the antimicrobial peptide includes a peptide sequence FRLKIKARLKVKIRFKL (RP554) (SEQ ID NO: 5), or a variant or fragment thereof.

In some embodiments of the antimicrobial polypeptide of formula 3, the sequence has a formula defined by the formula 3B:

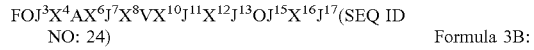

Formula 3B:

wherein:
$J^3$, $J^{15}$ and $J^{17}$ are each independently selected from I and L;
$X^4$, $X^8$ and $X^{16}$ are each independently selected from O and K;
$X^6$ and $X^{12}$ are each independently selected from O and R;
$J^7$ is selected from I and F;
$X^{10}$ are each independently selected from O, K and R; and
$J^{11}$ and $J^{13}$ are each independently selected from A and L.

In some instances of formula 3A or 3B, the antimicrobial peptide includes a peptide sequence FOIKARFOVRARLOLKI (RP553) (SEQ ID NO: 4), or a variant or fragment thereof.

In some instances of formula 3A or 3B, the antimicrobial peptide includes a peptide sequence FOLOAOIOVOLOAOIOL (RP555) (SEQ ID NO: 6), or a variant or fragment thereof.

In some instances of formula 3A or 3B, the antimicrobial peptide includes a peptide sequence FOLOAOIKVKLOAOIOL (RP556) (SEQ ID NO: 7), or a variant or fragment thereof.

Formula 6 Peptides

The antimicrobial polypeptide can include two striapathic regions linked via a bubble region (e.g., as described herein).

In some embodiments, the antimicrobial polypeptide comprises a sequence defined by the formula 6, in which two striapathic regions composed of alternating hydrophobic residues (J) and hydrophilic residues (X) are joined by a central bubble region (B):

Formula 6:

wherein:
B is a sequence selected from the following formulae C-Z-C and GGC-Z-CGG (SEQ ID NO: 25), wherein each C is a cysteine residue, each G is a glycine residue and Z consists of 3-5 amino acid residues selected from hydrophobic amino acid residues (J) and hydrophilic amino acid residue (X) (e.g., as described herein); and m is 0 or 1.

In some embodiments of the antimicrobial polypeptide of formula 6, B is a sequence selected from the following formulae $CJ^9J^{10}X^{11}J^{12}C$ and $(G)_nCJ^9J^{10}X^{11}J^{12}C(G)_n$ (SEQ ID NO: 26), wherein each C is a cysteine residue, each G is a glycine residue, each n is independently selected from 1-4 (e.g., 1, 2 or 3), each X is independently selected from a hydrophilic amino acid residue (e.g. lysine, arginine, histidine, aspartic acid, glutamic acid, asparagine, glutamine and ornithine) and each J is independently selected from a hydrophobic residue (e.g. phenylalanine, tryptophan, alanine, valine, glycine, isoleucine, leucine, and tyrosine).

In some cases of the peptide, $J^9$, $J^{10}$ and $J^{12}$ are independently selected from leucine, glycine and phenylalanine. In certain cases, $X^{11}$ is selected from ornithine and lysine.

In some embodiments of the antimicrobial polypeptide of formula 6, the polypeptide comprises a sequence defined by formula 6A:

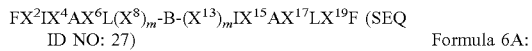
              ID NO: 27)              Formula 6A:

wherein:
B is a sequence selected from the following formulae $CLGX^{11}FC$ (SEQ ID NO: 28), $GCLGX^{11}FCG$ (SEQ ID NO: 29) and $GGCLGX^{11}FCGG$ (SEQ ID NO: 30), wherein each C is a cysteine residue, each G is a glycine residue and $X^{11}$ is selected from O and K;
$X^2$, $X^4$, each $X^8$, each $X^{13}$, $X^{15}$ and $X^{19}$ are independently selected from O and K;
$X^6$ and $X^{17}$ are each independently selected from R and O; and
each m is independently an integer selected from 0 and 1.

In some instances of formula 6A, the antimicrobial peptide includes a peptide sequence FOIOAOLGGCLGOFCGGIOAOLOF (RP564) (SEQ ID NO: 15), or a variant or fragment thereof.

In some instances of formula 6A, the antimicrobial peptide includes a peptide sequence FOIOAOLOGGCLGOFCGGOIOAOLOF (RP565) (SEQ ID NO: 16), or a variant or fragment thereof.

In some instances of formula 6A, the antimicrobial peptide includes a peptide sequence FOIKAOLGGCLGKFCGGIKAOLKF (RP566) (SEQ ID NO: 17), or a variant or fragment thereof.

In some instances of formula 6A, the antimicrobial peptide includes a peptide sequence
FOIKAOLKGGCLGKFCGGKIKAOLKF (RP 567) (SEQ ID NO: 18), or a variant or fragment thereof.

In some embodiments, the antimicrobial polypeptide comprises a sequence defined by the formula 6B, based on the formula 6:

                                                      Formula 6B:

wherein each C is a cysteine residue, each X is independently selected from a hydrophilic amino acid residue (e.g. lysine, arginine, histidine, aspartic acid, glutamic acid, asparagine, glutamine and ornithine); and each J is independently selected from a hydrophobic residue (e.g. phenylalanine, tryptophan, alanine, valine, glycine, isoleucine, leucine, and tyrosine). In some cases, each X is independently selected from ornithine, lysine and arginine. In some cases, each J is independently selected from phenylalanine, alanine, isoleucine, leucine and glycine.

In some instances of formula 6B, the antimicrobial peptide includes a peptide sequence FKIOARLCLGOFCIOARLK (RP550) (SEQ ID NO: 1), or a variant or fragment thereof.

In some embodiments, the antimicrobial polypeptide comprises a sequence defined by the formula 6C, based on the formula 6:

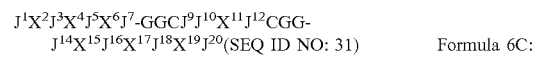
                                                Formula 6C:

wherein C is a cysteine residue, G is a glycine residue, each X is independently a hydrophilic amino acid residue (e.g. lysine, arginine, histidine, aspartic acid, glutamic acid, asparagine, glutamine or ornithine); and each J is independently a hydrophobic residue (e.g. phenylalanine, tryptophan, alanine, valine, glycine, isoleucine, leucine, or tyrosine). In some cases, each X is independently selected from ornithine, lysine and arginine. In some cases, each J is independently selected from phenylalanine, alanine, isoleucine, leucine and glycine.

In some instances of formula 6C, the antimicrobial peptide includes a peptide sequence FOIOAOLGGCLGOFCGGIOAOLOF (RP564) (SEQ ID NO: 15), or a variant or fragment thereof.

In some instances of formula 6C, the antimicrobial peptide includes a peptide sequence FOIKAOLGGCLGKFCGGIKAOLKF (RP566) (SEQ ID NO: 17), or a variant or fragment thereof.

In some embodiments, the antimicrobial polypeptide comprises a sequence defined by the formula 6D, based on the formula 6:

                                                Formula 6D:

wherein C is a cysteine residue, G is a glycine residue, each X is independently a hydrophilic amino acid residue (e.g. lysine, arginine, histidine, aspartic acid, glutamic acid, asparagine, glutamine or ornithine); and each J is independently a hydrophobic residue (e.g. phenylalanine, tryptophan, alanine, valine, glycine, isoleucine, leucine, or tyrosine). In some cases, each X is independently selected from ornithine, lysine and arginine. In some cases, each J is independently selected from phenylalanine, alanine, isoleucine, leucine and glycine.

In certain cases of the antimicrobial polypeptide of any one of formulae 6B to 6D, $J^1X^2J^3X^4J^5X^6J^7$ is $FX^2IX^4AX^6L$ (SEQ ID NO: 33), wherein $X^2$ and $X^4$ are each independently selected from O and K and $X^6$ is selected from R and O. In certain embodiments of any one of formulae 6B to 6D, $FX^2IX^4AX^6L$ (SEQ ID NO: 33) is selected from FKIOARL (SEQ ID NO: 34), FOIOAOL (SEQ ID NO: 35) and FOIKAOL (SEQ ID NO: 36). In some cases of any one of formulae 6B to 6D, $FX^2IX^4AX^6L$ (SEQ ID NO: 33) is FKIOARL (SEQ ID NO: 34). In some cases of any one of formulae 6B to 6D $FX^2IX^4AX^6L$ (SEQ ID NO: 33) is FOIOAOL (SEQ ID NO: 35). In other cases of any one of formulae 6B to 6D, $FX^2IX^4AX^6L$ (SEQ ID NO: 33) is FOIKAOL (SEQ ID NO: 36).

In some instances of formula 6D, the antimicrobial peptide includes a peptide sequence FOIOAOLOGGCLGOFCGGOIOAOLOF (RP565) (SEQ ID NO: 16), or a variant or fragment thereof.

In some instances of formula 6D, the antimicrobial peptide includes a peptide sequence FOIKAOLKGGCLGK-FCGGKIKAOLKF (RP567) (SEQ ID NO: 18), or a variant or fragment thereof.

In certain cases of any of formulae 6B to 6D, the sequence fragment $J^{14}X^{15}J^{16}X^{17}J^{18}X^{19}J^{20}$ is $IX^{15}AX^{17}LX^{19}$ $(F)_p$ (SEQ ID NO: 37) wherein $X^{15}$ and $X^{19}$ are each independently selected from O and K, $X^{17}$ is selected from R and O and p is 1 or 0. In some cases of any one of formulae 6B to 6D, the sequence fragment $IX^{15}AX^{17}LX^{19}$ $(F)_p$ (SEQ ID NO: 37) is selected from IOARLK (SEQ ID NO: 38), IOAOLOF (SEQ ID NO: 39) and IKAOLKF (SEQ ID NO: 40). In some cases of any one of formulae 6B to 6D, the sequence fragment $IX^{15}AX^{17}LX^{19}$ $(F)_p$ (SEQ ID NO: 37) is IOARLK (SEQ ID NO: 38). In some cases of any one of formulae 6B to 6D, the sequence fragment $IX^{15}AX^{17}LX^{19}$ $(F)_p$ (SEQ ID NO: 37) is IOAOLOF (SEQ ID NO: 39). In some cases of any one of formulae 6B to 6D, the sequence fragment $IX^{15}AX^{17}LX^{19}$ $(F)_p$ is IKAOLKF (SEQ ID NO: 40).

In some cases of the antimicrobial polypeptide of formulae 6, the region having the sequence C-Z-C or GGC-Z-CGG (SEQ ID NO: 25) is referred to as a bubble region as described herein. In certain cases, Z is of the formula $J^9J^{10}X^{11}J^{12}$, wherein each J is independently selected from leucine, glycine and phenylalanine and X is selected from ornithine and lysine. In some embodiments, the bubble region in any of formulae 6 to 6D has a sequence selected from, CLGOFC (SEQ ID NO: 41), CLGKFC (SEQ ID NO: 42), GGCLGOFC (SEQ ID NO: 43) and GGCLGKFCGG (SEQ ID NO: 44).

Formula 7 Peptides

In some embodiments, the antimicrobial polypeptide comprises a sequence defined by the formula 7, comprising four cysteine residues:

$$Z^1\text{-}C^1\text{-}Z^2\text{-}C^2\text{-}Z^3\text{-}C^3\text{-}Z^4\text{-}C^4\text{-}Z^5 \text{(SEQ ID NO: 45)} \quad \text{Formula 7:}$$

wherein, $C^1$ to $C^4$ are each cysteine residues; and $Z^1$ to $Z^5$ are each independently 1-5 amino acid residues. In some embodiments, each of $Z^1$, $Z^2$, $Z^4$ and $Z^5$ are each striapathic regions consisting of a mixture of hydrophobic amino acid residues (J) and hydrophilic residues (X) (e.g., as described herein). $Z^3$ can be any convenient linking sequence of residues.

In some embodiments, each of $Z^1$ to $Z^5$ consists of a mixture of hydrophobic amino acid residues and hydrophilic residues. In some embodiments, each of $Z^1$ to $Z^4$ consists of a mixture of hydrophobic residues and hydrophilic residues; and $Z^5$ is a single hydrophilic residue. In some embodiments, each of $Z^2$ to $Z^5$ consists of a mixture of hydrophobic residues and hydrophilic residues; and $Z^1$ is a single hydrophilic residue. In some embodiments, $Z^1$, $Z^3$ and $Z^5$ each consists of a mixture of hydrophobic residues and hydrophilic residues; and $Z^2$ and $Z^4$ are each a single hydrophilic residue. In some embodiments $Z^3$ consists of a mixture of four amino acid residues selected from hydrophobic residues and hydrophilic residues. In some embodiments $Z^2$ and $Z^4$ consist of an equivalent number of amino acid residues.

In some cases, the antimicrobial polypeptide of formula 7 includes one or more additional hydrophilic or hydrophobic residues at the C terminal or the N terminal.

In some embodiments, the antimicrobial polypeptide comprises a sequence defined by the formula 7A, based on the formula 7:

$$X^1J^2\text{-}C^1\text{-}J^3X^4J^5\text{-}C^2\text{-}J^6X^7J^8J^9\text{-}C^3\text{-}J^{10}X^{11}X^{12}\text{-}C^4\text{-}X^{13}$$
(SEQ ID NO: 46) Formula 7A:

wherein $C^1$ to $C^4$ are each a cysteine residue, each X is independently selected from a hydrophilic amino acid residue (e.g. lysine, arginine, histidine, aspartic acid, glutamic acid, asparagine, glutamine and ornithine); and each J is independently selected from a hydrophobic residue (e.g. phenylalanine, tryptophan, alanine, valine, glycine, isoleucine, leucine, and tyrosine). In some cases, each X is independently selected from lysine, ornithine and arginine. In some cases, each J is independently selected from phenylalanine, isoleucine, glycine, tryptophan, valine and tyrosine.

In some embodiments, the antimicrobial polypeptide of the formula 7A, has the formula 7A':

$$X^1J^2\text{-}C^1\text{-}J^3X^4V\text{-}C^2\text{-}YX^7GI\text{-}C^3\text{-}J^{10}X^{11}X^{12}\text{-}C^4\text{-}X^{13}$$
(SEQ ID NO: 47) Formula 7A¹:

wherein $X^1$ is selected from O and R;
$J^2$ and $J^3$ are each independently selected from F and W;
$X^4$, $X^7$, $X^{11}$, $X^{12}$ and $X^{13}$ are each independently selected from O and K; and
$J^{10}$ is selected from Y and F.

In some instances of formula 7A¹, the antimicrobial peptide includes a peptide sequence RFCWKVCYK-GICFKKCK (RP557) (SEQ ID NO: 8), or a variant or fragment thereof.

In some instances of formula 7A¹, the antimicrobial peptide includes a peptide sequence RWCFKVCYKGI-CYKKCK (RP560) (SEQ ID NO: 11), or a variant or fragment thereof.

In some instances of formula 7A¹, the antimicrobial peptide includes a peptide sequence OWCFOVCYOGICY-OOCO (RP559) (SEQ ID NO: 10), or a variant or fragment thereof.

In some instances of formula 7A¹, the antimicrobial peptide includes a peptide sequence OFCWOVCYOGIC-FOOCO (RP661) (SEQ ID NO: 12), or a variant or fragment thereof.

In some embodiments, the antimicrobial polypeptide comprises a sequence defined by the formula 7B, based on the formula 7:

$$X^1\text{-}C^1\text{-}X^2X^3J^4\text{-}C^2\text{-}J^5J^6X^7J^8\text{-}C^3\text{-}J^9X^{10}J^{11}\text{-}C^4\text{-}J^{12}X^{13}$$
(SEQ ID NO: 48) Formula 7B:

wherein $C^1$ to $C^4$ are each a cysteine residue, each X is independently selected from a hydrophilic amino acid residue (e.g. lysine, arginine, histidine, aspartic acid, glutamic acid, asparagine, glutamine and ornithine); and each J is independently selected from a hydrophobic residue (e.g. phenylalanine, tryptophan, alanine, valine, glycine, isoleucine, leucine, and tyrosine). In some cases, each X is independently selected from lysine, ornithine and arginine. In some cases, each J is independently selected from phenylalanine, isoleucine, glycine, tryptophan, valine and tyrosine.

In some embodiments, the antimicrobial polypeptide of the formula 7B, has the formula 7B¹:

$$X^1\text{-}C^1\text{-}X^2X^3J^4\text{-}C^2\text{-}IGX^7Y\text{-}C^3\text{-}VX^{10}J^{11}\text{-}C^4\text{-}J^{12}X^{13}$$
(SEQ ID NO: 49) Formula 7B¹:

wherein $X^1$, $X^2$, $X^3$, $X^7$ and $X^{10}$ are each independently selected from O and R;
$J^4$ is selected from Y and F;
$J^{11}$ and $J^{12}$ are each independently selected from F and W; and
$X^{13}$ is selected from K and O.

In some instances of formula 7B[1], the antimicrobial peptide includes a peptide sequence RCRRYCIGRYCVR-FCWK (RP558) (SEQ ID NO: 9), or a variant or fragment thereof.

In some instances of formula 7B', the antimicrobial peptide includes a peptide sequence OCOOFCIGOYCVOW-CFO (RP562) (SEQ ID NO: 13), or a variant or fragment thereof.

In some embodiments, the antimicrobial polypeptide comprises a sequence defined by the formula 7C, based on the formula 7:

$$X^1J^2J^3\text{-}C^1\text{-}J^4\text{-}C^2\text{-}J^5X^6X^7X^8\text{-}C^3\text{-}J^9\text{-}C^4\text{-}J^{10}X^{11}J^{12}J^{13}X^{14}$$
(SEQ ID NO: 50)     Formula 7C:

wherein $C^1$ to $C^4$ are each a cysteine residue, each X is independently selected from a hydrophilic amino acid residue (e.g. lysine, arginine, histidine, aspartic acid, glutamic acid, asparagine, glutamine and ornithine); and each J is independently selected from a hydrophobic residue (e.g. phenylalanine, tryptophan, alanine, valine, glycine, isoleucine, leucine, and tyrosine). In some cases, each X is arginine. In some cases, each J is independently selected from phenylalanine, glycine, leucine, valine and tyrosine.

In some embodiments of the antimicrobial polypeptide of formula 7, the region having the sequence $C^2\text{-}Z^3\text{-}C^3$ is a bubble region as described herein. In certain cases, $Z^3$ consists of a mixture of 3 to 5 hydrophobic and hydrophilic amino acid residues (e.g. J and X as described herein). In certain cases, $Z^3$ consists of a mixture of four amino acid residues selected from tyrosine, glycine, phenylalanine, isoleucine, lysine, arginine and ornithine. In some cases, $Z^3$ consists of three hydrophobic amino acid residues (J) and one hydrophilic amino acid residue (X). In certain cases, $Z^3$ consists of a tyrosine, a glycine, an isoleucine and a lysine residue. In certain cases, $Z^3$ consists of a tyrosine, a glycine, an isoleucine and an ornithine residue. In certain cases, $Z^3$ consists of a tyrosine, a glycine, an isoleucine and a lysine residue. In some embodiments, the bubble region in formula 7 has the formula CYKGIC (SEQ ID NO: 22). In some embodiments, the bubble region in formula 7 has the formula CYOGIC (SEQ ID NO: 51). In some embodiments, the bubble region in formula 7 has the formula CIGRYC (SEQ ID NO: 52). In some embodiments, the bubble region in formula 7 has the formula CIGOYC (SEQ ID NO: 53). In some cases, $Z^3$ consists of one hydrophobic amino acid residue (J) and three hydrophilic amino acid residues (X). In certain cases $Z^3$ consists of one phenylalanine residue and three arginine residues. In some embodiments, the bubble region in formula 7 has the formula CFRRRC (SEQ ID NO: 54).

In some embodiments of the antimicrobial polypeptide of formula 7, the bubble region having the sequence $C^2\text{-}Z^3\text{-}C^3$ forms one linked region, and the cysteines $C^1$ and $C^4$ link to form an additional linked region (e.g., see FIG. 1B). In certain embodiments, antimicrobial peptides of formula 7 comprises a formula selected from 7A to 7C, each of which form a hairpin secondary structure containing two linked regions. A specific example of an antimicrobial peptide of the invention according to 7A including a bubble region and an additional linked region includes:

RFCWKVCYKGICFKKCK     (RP557,SEQ ID NO: 8)

Examples of antimicrobial peptides according to aspects of the invention are provided below in Table 2. These examples are representative, and not meant to be limiting to the scope of the invention. For example, a fragment (e.g., as described herein), or a variant (e.g., as described herein) are also of interest. The "O" residues in the sequences listed below represent the amino acid ornithine.

TABLE 2

Examples of antimicrobial peptides

| RP # | SEQ ID NO: | Amino Acid Sequence |
|---|---|---|
| 550 | 1 | FKIOARLCLGOFCIOARLK |
| 551 | 2 | FIOKFAKOFKOFIOKFAKFAFAF |
| 552 | 3 | FAFAFKAFKKAFKOFOOAFOOAF |
| 553 | 4 | FOIKARFOVRARLOLKI |
| 554 | 5 | FRLKIKARLKVKIRFKL |
| 555 | 6 | FOLOAOIOVOLOAOIOL |
| 556 | 7 | FOLOAOIKVKLOAOIOL |
| 557 | 8 | RFCWKVCYKGICFKKCK |
| 558 | 9 | RCRRYCIGRYCVRFCWK |
| 559 | 10 | OWCFOVCYOGICYOOCO |
| 560 | 11 | RWCFKVCYKGICYKKCK |
| 561 | 12 | OFCWOVCYOGICFOOCO |
| 562 | 13 | OCOOFCIGOYCVOWCFO |
| 563 | 14 | RGVCVCFRRRCYCLRGGR |
| 564 | 15 | FOIOAOLGGCLGOFCGGIOAOLOF |
| 565 | 16 | FOIOAOLOGGCLGOFCGGOIOAOLOF |
| 566 | 17 | FOIKAOLGGCLGKFCGGIKAOLKF |
| 567 | 18 | FOIKAOLKGGCLGKFCGGKIKAOLKF |

The exemplary antimicrobial polypeptide sequences described herein (e.g., Table 2) are merely examples and are not the only antimicrobial polypeptides provided herein. Indeed, fragments and variants of the sequences of the disclosed peptides are within the scope of the present disclosure.

A "fragment" of the invention includes at least 6, 7, 8, 9, 10, 11, 12, 13, 14, 15, 16, 17, 18, 19, 20, 21, 22, or 23 contiguous amino acid residues of a polypeptide disclosed herein (or up to one less than the number of amino acid residues in the subject polypeptide) and retains at least one antimicrobial property of the subject polypeptide. Thus, fragments of the invention include polypeptides that are missing one, two, three, four, or more amino acids from the N-terminus and/or the C-terminus relative to a polypeptide disclosed herein.

A "variant" of the invention is a polypeptide that is substantially similar to a polypeptide disclosed herein and retains at least one antimicrobial property of the subject polypeptide. Variants can include deletions (i.e., truncations) of one or more amino acid residues at the N-terminus or the C-terminus of a subject polypeptide disclosed herein; deletion and/or addition of one or more amino acid residues at one or more internal sites in the subject polypeptide disclosed herein; and/or substitution of one or more amino acid residues at one or more positions in the subject polypeptide disclosed herein. For subject polypeptides that are 17 amino acid residues in length or shorter, variant polypeptides can include three or fewer (e.g., two, one, or none) deleted amino acid residues, whether located internally, at the N-terminal end, and/or at the C-terminal end.

As such, in certain embodiments, the invention provides polypeptides that include an amino acid sequence having from 1 to 10 amino acid differences (e.g., 10 or fewer, 9 or fewer, 8 or fewer, 7 or fewer, 6 or fewer, 5 or fewer, 4 or fewer, 3 or fewer, 2 or fewer, or 1 amino acid difference) to any one of the antimicrobial polypeptides disclosed herein (e.g., as shown in Table 2) and still retain at least one antimicrobial property. An "amino acid difference" as used herein includes: an amino acid substitution, an amino acid insertion, a terminal amino acid addition, an amino acid deletion, a terminal amino acid truncation, or any combination thereof. A substituted amino acid residue (or residues) can be unrelated to the amino acid residue being replaced (e.g., unrelated in terms or hydrophobicity/hydrophilicity, size, charge, polarity, etc.), or the substituted amino acid residue can constitute similar, conservative, or highly conservative amino acid substitution. As used herein, "similar," "conservative," and "highly conservative" amino acid substitutions are defined as shown in Table 3, below. The determination of whether an amino acid residue substitution is similar, conservative, or highly conservative is based exclusively on the side chain of the amino acid residue and not the peptide backbone, which may be modified to increase peptide stability, as discussed below.

TABLE 3

Classification of Amino Acid Substitutions

| Amino Acid in Subject Polypeptide | Similar Amino Acid Substitutions | Conservative Amino Acid Substitutions | Highly Conservative Amino Acid Substitutions |
|---|---|---|---|
| Glycine (G) | A,S,N | A | n/a |
| Alanine (A) | S,G,T,V,C,P,Q | S,G,T | S |
| Serine (S) | T,A,N,G,Q | T,A,N | T,A |
| Threonine (T) | S,A,V,N,M | S,A,V,N | S |
| Cysteine (C) | A,S,T,V,I | A | n/a |
| Proline (P) | A,S,T,K | A | n/a |
| Methionine (M) | L,I,V,F | L,I,V | L,I |
| Valine (V) | I,L,M,T,A | I,L,M | I |
| Leucine (L) | M,I,V,F,T,A | M,I,V,F | M,I |
| Isoleucine (I) | V,L,M,F,T,C | V,L,M,F | V,L,M |
| Phenylalanine (F) | W,L,M,I,V | W,L | n/a |
| Tyrosine (Y) | F,W,H,L,I | F,W | F |
| Tryptophan (W) | F,L,V | F | n/a |
| Asparagine (N) | Q | Q | Q |
| Glutamine (Q) | N | N | N |
| Aspartic Acid (D) | E | E | E |
| Glutamic Acid (E) | D | D | D |
| Histidine (H) | R,K,O | R,K,O | R,K,O |
| Lysine (K) | R,H,O | R,H,O | R,O |
| Arginine (R) | K,H,O | K,H,O | K,O |
| Ornithine (O) | R,H,K | R,H,K | R,K |

Accordingly, the invention further provides polypeptides that include an amino acid sequence that is at least 50% identical (e.g., at least 60%, 70%, 80%, 90%, 95%, 98%, 99% or more identical) to any one of the antimicrobial polypeptides disclosed herein (e.g., as shown in Table 2) and still retain at least one antimicrobial property. In certain embodiment, such polypeptide sequences include an amphipathic or striapathic region having a cationic charge as described in detail above. Moreover, such polypeptides may include additional structural features as described herein, including: a bubble region, a beta-turn region, a polyproline helix structure, a tail, amphipathic region dimer, etc.

In certain embodiments, the subject antimicrobial polypeptide includes a sequence comprising:

a) a peptide sequence selected from RP550-567 (SEQ ID NO: 1 to SEQ ID NO 18);

b) a sequence having at least 80% sequence identity (e.g., at least 85%, at least 90%, or at least 95% sequence identity) with the sequence defined in a); or c) a sequence having five or less (e.g., four or less, three or less, two or less such as one or two) amino acid substitutions relative to the sequence defined in a), wherein the one or two amino acid substitutions are substitutions for amino acids according to Table 3 (e.g., a similar amino acid substitution, a conservative amino acid substitution or a highly conservative amino acid substitution).

In certain embodiments, the subject antimicrobial polypeptide includes a sequence comprising:

a) a peptide sequence selected from RP550-567 (SEQ ID NO: 1 to SEQ ID NO 18); or b) a sequence having five or less (e.g., four or less, three or less, two or less such as one or two) amino acid substitutions relative to the sequence defined in a), wherein the five or less amino acid substitutions consist of substitution of a cationic amino acid of the sequence with an alternative cationic amino acid residue (e.g., K for O, O for K, K for R, etc.).

In certain cases, the sequence defined in a) comprises at least one lysine residue which is substituted for an ornithine, histidine or an arginine residue. In some cases, the sequence defined in a) comprises at least one lysine residue which is substituted for an ornithine or an arginine residue. In certain other cases, the sequence defined in a) comprises at least one ornithine residue which is substituted for a lysine, histidine or an arginine residue. In some cases, the sequence defined in a) comprises at least one ornithine residue which is substituted for a lysine or an arginine residue. In other cases, the sequence defined in a) comprises at least one arginine residue which is substituted for an ornithine, histidine or a lysine residue. In some cases, the sequence defined in a) comprises at least one arginine residue which is substituted for an ornithine or a lysine residue.

In certain cases, the subject sequence comprises RP 550 (SEQ ID NO: 1). In certain cases, the subject sequence comprises RP 551 (SEQ ID NO: 2). In certain cases, the subject sequence comprises RP 552 (SEQ ID NO: 3). In certain cases, the subject sequence comprises RP 553 (SEQ ID NO: 4). In certain cases, the subject sequence comprises RP 554 (SEQ ID NO: 5). In certain cases, the subject sequence comprises RP 555 (SEQ ID NO: 6). In certain cases, the subject sequence comprises RP 556 (SEQ ID NO: 7). In certain cases, the subject sequence comprises RP 557 (SEQ ID NO: 8). In certain cases, the subject sequence comprises RP 558 (SEQ ID NO: 9). In certain cases, the subject sequence comprises RP 559 (SEQ ID NO: 10). In certain cases, the subject sequence comprises RP 560 (SEQ ID NO: 11). In certain cases, the subject sequence comprises RP 561 (SEQ ID NO: 12). In certain cases, the subject sequence comprises RP 562 (SEQ ID NO: 13). In certain cases, the subject sequence comprises RP 563 (SEQ ID NO: 14). In certain cases, the subject sequence comprises RP 564 (SEQ ID NO: 15). In certain cases, the subject sequence comprises RP 565 (SEQ ID NO: 16). In certain cases, the subject sequence comprises RP 566 (SEQ ID NO: 17). In certain cases, the subject sequence comprises RP 567 (SEQ ID NO: 18)

In certain cases, the sequence set forth in a) is RP 550 (SEQ ID NO: 1). In certain cases, the sequence set forth in a) is RP 551 (SEQ ID NO: 2). In certain cases, the sequence set forth in a) is RP 552 (SEQ ID NO: 3). In certain cases, the sequence set forth in a) is RP 553 (SEQ ID NO: 4). In certain cases, the sequence set forth in a) is RP 554 (SEQ ID NO: 5). In certain cases, the sequence set forth in a) is RP 555 (SEQ ID NO: 6). In certain cases, the sequence set forth in a) is RP 556 (SEQ ID NO: 7). In certain cases, the sequence set forth in a) is RP 557 (SEQ ID NO: 8). In certain cases, the sequence set forth in a) is RP 558 (SEQ ID NO: 9). In certain cases, the sequence set forth in a) is RP 559 (SEQ ID NO: 10). In certain cases, the sequence set forth in a) is RP 560 (SEQ ID NO: 11). In certain cases, the sequence set forth in a) is RP 561 (SEQ ID NO: 12). In certain cases, the sequence set forth in a) is RP 562 (SEQ ID NO: 13). In certain cases, the sequence set forth in a) is RP 563 (SEQ ID NO: 14). In certain cases, the sequence set forth in a) is RP 564 (SEQ ID NO: 15). In certain cases, the sequence set forth in a) is RP 565 (SEQ ID NO: 16). In certain cases, the sequence set forth in a) is RP 566 (SEQ ID NO: 17). In certain cases, the sequence set forth in a) is RP 567 (SEQ ID NO: 18).

In certain instances of the subject peptides (e.g., described herein) and compositions, one or more of the following peptide sequences of Table 4 are excluded:

TABLE 4

| SEQ ID NO: | Amino Acid Sequence |
|---|---|
| 56 | RVFKKAFRKFKKLFKRAF |
| 57 | FARKFLKKFKRFAKKFVR |
| 58 | FKRKIKAKLRFKAKVRLK |
| 59 | FAFAFRVFKKAFRKFKKLFKRAF |
| 60 | FARKFLKKFKRFAKKFVRFAFAF |
| 61 | KIRAKLCLGRFCIRAKLR |
| 62 | KIKARLCLGKFCIKARLK |
| 63 | FAFAFKAFKKAFKKFKKAFKKAFGPGRFAKKFAKKFKKFAKK FAKFAFAF |
| 64 | FAKKFAKKFKKFAKKFAKFAFAFGPGRFAFAFKAFKKAFKKF KKAFKKAF |
| 65 | MGFKLRAKIKVRLRAKIKL |
| 66 | CVOLFPVOLFPC |
| 67 | CKLRFRGPGRIKVRLC |
| 68 | CPGFAKKFAKKFKKFAKKFAKFAFAF |
| 69 | KIRAKLCLGRFCIRAKLR |
| 70 | KKKPKPPYLPKPKPPPFFPPKLPPKI |
| 71 | FAFAFKAFKKAFKKFKKAFKKAFGPC |
| 72 | FAFAFAFKKAFKKFKKAFKKAF |
| 73 | FAFAFOAFOOAFOOFOOAFOOAF |
| 74 | FAOOFAOOFOOFAOOFAOFAFAF |
| 75 | FAKKFAKKFKKFAKKFAFAFAF |
| 76 | RLARIVGGFAOOFAOOFOOFAOOFAOFAFAF |
| 77 | CRLARIVCGGFAOOFAOOFOOFAOOFAOFAFAF |
| 78 | FOIOAOLGGCLGOFCGGIOAOLOF |

TABLE 4-continued

| SEQ ID NO: | Amino Acid Sequence |
|---|---|
| 79 | OLOSLLKTLSOAOOOOLOTOOOAISO |
| 80 | ALWMTLOOOVLOAOAOALNAVLVGANA |
| 81 | AFAFTAOOOFAOFOAOFANFAFAGFNA |

Compositions

The present disclosure provides compositions that include an antimicrobial polypeptide as described herein. For example, the antimicrobial polypeptide can be any of the polypeptides listed in Table 2 or a fragment or variant thereof that retains antimicrobial activity. In certain embodiments, the antimicrobial polypeptide included in the compositions of this disclosure will be a synthetic polypeptide (e.g., made by chemical synthesis and/or produced recombinantly).

The compositions of the invention can include a single antimicrobial polypeptide, or combinations of different antimicrobial polypeptides. The compositions can be substantially free of proteins and other polypeptides. As used herein, the term "substantially free of proteins and other polypeptides" means that less than 5% of the protein content of the composition is made up of proteins and other polypeptides that are not an antimicrobial polypeptide of the invention. A composition that is substantially free of non-antimicrobial polypeptides of the invention can have less than 4%, 3%, 2%, 1%, 0.5%, 0.1%, 0.05%, 0.01%, or less of other non-antimicrobial polypeptides.

The compositions of the invention in certain embodiments contain an antimicrobial polypeptide that is not naturally found in a human or other mammal or animal.

The subject compositions can be provided in any convenient form. In some cases, the composition is a solid composition. In certain cases, the composition is a liquid, e.g., aqueous composition. In certain instances, the solid composition is a lyophilized composition that can be provided to an end use in a solid form suitable for reconstitution with a liquid, e.g., an aqueous solution.

The compositions of the invention can include at least 0.1 mg (e.g., at least 0.2, at least 0.3, at least 0.4, at least 0.5, at least 1, at least 5, at least 10, at least 20, at least 30, at least 40, at least 50, at least 75, at least 100, at least 150, at least 200, at least 250, at least 300, at least 400, at least 500, at least 600, at least 700, at least 800, at least 900, at least 1000 mg, or more) of antimicrobial polypeptide. Thus, for example, the compositions can include an amount of antimicrobial polypeptide equal to about 0.1 mg to about 1 mg, or about 1 mg to about 1000 mg (e.g., about 5 mg to about 900 mg, about 5 mg to about 800 mg, about 5 mg to about 700 mg, about 5 mg to about 600 mg, about 10 mg to about 500 mg, about 10 mg to about 400 mg, about 10 mg to about 300 mg, about 10 mg to about 250 mg, about 10 mg to about 200 mg, about 10 mg to about 150 mg, about 10 mg to about 100 mg, about 50 mg to about 500 mg, about 50 mg to about 400 mg, about 50 mg to about 300 mg, about 50 mg to about 250 mg, about 50 mg to about 200 mg, about 50 mg to about 150 mg, about 50 mg to about 100 mg, about 75 mg to about 500 mg, about 75 mg to about 400 mg, about 75 mg to about 300 mg, about 75 mg to about 250 mg, about 75 mg to about 200 mg, about 75 mg to about 150 mg, about 75 mg to about 100 mg, about 100 mg to about 500 mg, about 100 mg to about 400 mg, about 100 mg to about 300 mg, about 100 mg to about 250 mg, about 100 mg to about 200 mg, or any other range containing two of the foregoing endpoints).

The compositions of the invention can include a solution that contains at least 0.1 mg/ml (e.g., at least 0.5, 1, 2, 3, 4, 5, 10, 15, 20, 25, 30, 35, 40, 45, 50, 55, 60, 65, 70, 75, 80, 85, 90, 95, 100 mg/ml or more) of an antimicrobial polypeptide. Thus, for example, the compositions can include a solution having an antimicrobial polypeptide concentration of about 0.1 mg/ml to about 100 mg/ml (e.g., about 5 mg/ml to about 90 mg/ml, about 5 mg/ml to about 80 mg/ml, about 5 mg/ml to about 70 mg/ml, about 5 mg/ml to about 60 mg/ml, about 5 mg/ml to about 50 mg/ml, about 10 mg/ml to about 50 mg/ml, about 10 mg/ml to about 40 mg/ml, about 10 mg/ml to about 30 mg/ml, about 10 mg/ml to about 25 mg/ml, about 10 mg/ml to about 20 mg/ml, about 10 mg/ml to about 15 mg/ml, or any other range containing two of the foregoing endpoints).

The compositions of the invention include pharmaceutical compositions. Such pharmaceutical compositions can comprise one or more antimicrobial polypeptides and a pharmaceutically acceptable carrier. Pharmaceutical compositions can further include an additional bioactive agent other than an antimicrobial polypeptide of the invention. The additional bioactive agent can be a therapeutic/antimicrobial agent, such as a conventional antibiotic. The conventional antibiotic can have antimicrobial properties or other properties that the antimicrobial polypeptides of the invention augment or are augmented by. In some embodiments, the additional bioactive agent is selected from an antimicrobial agent, an anti-inflammatory drug, an anti-nausea drug, an anti-pain medication and combinations thereof. In certain embodiments the pharmaceutical composition includes a carrier, e.g., a carrier protein such as serum albumin (e.g., HAS, BSA, etc.), which can be purified or recombinantly produced. By mixing the antimicrobial polypeptide(s) in the pharmaceutical composition with serum album, the antimicrobial polypeptides can be effectively "loaded" onto the serum albumin, allowing a greater amount of antimicrobial polypeptide to be successfully delivered to a site of infection.

The pharmaceutical compositions of the present invention can be formulated for oral administration, parenteral administration, inhalation administration, topical administration, or the like. Compositions formulated for oral delivery can, for example, include an enteric coat, to ensure that antimicrobial peptides contained therein reach the intestine and beyond. Compositions formulated for topical delivery can be, for example, suspended in a gel or cream, coated on a microneedle, or infused into a bandage or topical patch, to extend the duration of action of the antimicrobial peptides contained therein. Any inhalable formulation which can provide for an aerosolized form including a subject peptide for delivery to a patient via the intrapulmonary route may be used in conjunction with the present disclosure. In some cases, an inhalable composition includes liposomes which are delivered via an aerosol to the lungs of a human patient, the liposomes comprising free and encapsulated peptide. The liposomes may be unilamellar or multilamellar, and may be bioadhesive, containing a molecule such as hyaluronic acid. At least one therapeutic agent in addition to the free and liposome-encapsulated anti-infective may also be included in the composition. The therapeutic agent may be free peptide or encapsulated peptide present with a pharmaceutically acceptable carrier useful for direct inhalation into human lungs.

In certain embodiments, it may be desirable to administer one or more compounds of the invention locally to the area in need of treatment. This may be achieved, for example, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

In certain instances, the pharmaceutical composition is an ophthalmic composition formulated for the treatment of an eye disease or condition. The ophthalmic compositions described herein may be formulated in any applicable dosage form. Exemplary dosage forms include, but are not limited to, eye drops (liquids), ointments, oils, multi-phase systems (such as, liposome, micellular, homogenates or suspensions of liquids or semi-solid or solid particles), gels, creams, pads or strips. In one embodiment, the active ingredient (peptide) is in a water-based (aqueous) drug product. In another embodiment, the active ingredient is in a petrolatum-based drug product. One embodiment of the present invention is the use of topical formulations of peptides described herein to treat ocular infections caused by, without limitation, bacteria, herpes simplex virus, cytomegalovirus, varicella zoster virus, adenovirus and/or a combination thereof. One embodiment of the present invention is the use of topical formulations of peptides described herein to treat bacterial keratitis. In some cases, the bacterial keratitis is caused by infection with *Staphylococcus aureus* or *Pseudomonas aeruginosa*.

The composition can be topically applied to a patient in need of the treatment. In some cases, the composition is formulated as eye drops. In certain cases, the composition is formulated for subconjunctival administration. In some cases, the ophthalmic composition is an aqueous composition which includes the subject peptide or a pharmacologically acceptable salt, optionally in combination with an amount of any convenient additional excipients, e.g., a cellulose compound or a pharmacologically acceptable salt which is effective to increase intraocular absorption in the aqueous humor. The ophthalmic composition may be applied discretely one to four times per day as eye drops. Alternatively, the antimicrobial peptide may be continuously applied over time by any topical means. A hydrophilic hydrogel contact lens and an ocular polymer insert for topical application of an ophthalmic composition to the eyes of a patient is also disclosed. Any convenient methods and compositions can be adapted for use in conjunction with the subject ophthalmic compositions. See e.g., U.S. Pat. No. 9,044,425. The composition can include any carrier or excipients that known to one skilled in the art that are suitable for intraocular administration. Exemplary excipients include those discussed in U.S. Patent Application Publication No. 2008/0241252 to Lyons et al. and PCT Application Publication No. WO 2004/043480, which are incorporated by references in their entireties.

Although liposomes have been described as a vehicle to provide encapsulation of the therapeutic peptide, there is no intention to limit the formulation to liposomal formulations. A combination of immediate and sustained release formulations or carriers of an anti-infective peptide in the lung may be achieved via a multitude of ways including microspheres, polymers, gels, emulsions, particulates or suspensions, either singly or in combination. Some formulations or carriers may have properties that result in closer association with the biofilm matrix and these may prove more advantageous with respect to increasing the therapeutic levels of the anti-infective peptide proximal to the biofilm bacteria.

Aspects of the disclosure include antimicrobial compositions that find use in a variety of applications. In some instances, the subject composition finds use as an antimicrobial preservative, disinfectant or sterile storage medium. Applications of interest include use as a disinfectant or storage medium for an ocular device, such as a contact lens, an intraocular lens implant or a drug-eluting ocular device. In certain instances, the subject composition can be provided to a subject, as a solid or liquid composition, for use in a solution for storing, soaking and/or rinsing a contact lens. The solutions are well suited for ophthalmic use and are effective in cleaning, disinfecting, and sterilizing the contact lens upon exposure to the composition without the need for physical or thermal treatment of the lens. Any convenient carriers, excipients and/or diluents that find use in sterile or disinfecting solutions can be adapted for inclusion in the subject antimicrobial compositions. See e.g., U.S. Pat. No. 6,482,799.

Alternatively, the antimicrobial peptides of the present disclosure can be coated on the surface of medical devices, such as implantable medical devices, surgical instruments and indwelling medical devices (e.g., pacemakers, catheters, artificial joints, and the like), as a means of preventing infection.

Methods

The polypeptides of this disclosure provide powerful tools for treating or preventing a variety of conditions and diseases of interest. Aspects of the method include administering to a subject in need thereof a therapeutically effective amount of a subject peptide to treat the subject. By "a therapeutically effective amount" is meant the concentration of a peptide that is sufficient to elicit the desired biological effect (e.g., treatment of the condition or disease). The terms "treat," "treating," and similar words shall mean stabilizing, reducing the symptoms of, preventing the occurrence of, or curing a medical condition. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition. Thus treatment includes: (i) prevention, that is, reducing the risk of development of clinical symptoms, including causing the clinical symptoms not to develop, e.g., preventing disease progression to a harmful state; (ii) inhibition, that is, arresting the development or further development of clinical symptoms, e.g., mitigating or completely inhibiting an active disease; and/or (iii) relief, that is, causing the regression of clinical symptoms.

The antimicrobial polypeptides of the invention provide powerful tools for treating or preventing a microbial infection in a subject, caused by a variety of microorganisms (e.g., bacteria, viruses, fungi, and parasites). Accordingly, the invention provides methods of eliminating, reducing the number of, or significantly reducing the replication of at least one microbial organism in a subject. The subject peptides can have broad-spectrum antifungal and antibacterial activity. In certain cases, the subject peptides and methods provide a reduced risk of development of pathogen resistance.

The subject can be any animal, such as a domesticated animal (e.g., a horse, cow, pig, goat, sheep, rabbit, chicken, turkey, duck, etc.), a pet (e.g., a dog, cat, rabbit, hamster, gerbil, bird, fish, etc.), a lab animal (e.g., a mouse, rat, monkey, chimpanzee, owl, fish, etc.), a zoo animal (e.g., a gorilla, orangutan, chimpanzee, monkey, elephant, camel, zebra, boar, lion, tiger, giraffe, bear, bird, etc.), a wild animal (e.g., a deer, wolf, mountain lion, bird, etc.), or a human subject (e.g., a patient). In some cases, the subject is human.

A subject suitable for treatment with a peptide composition may be identified by well-established indicators of risk for developing a disease or well-established hallmarks of an existing disease. For example, indicators of an infection include fever, pus, microorganism positive cultures, inflammation, and the like. Infections that may be treated with peptides provided by the present invention include without limitation those caused by or due to microorganisms, whether the infection is primary, secondary, opportunistic, or the like. Examples of microorganisms include bacteria (e.g., Gram-positive, Gram-negative), fungi, (e.g., yeast and molds), parasites (e.g., protozoans, nematodes, cestodes and trematodes), viruses (e.g., HIV, HSV, VSV), algae, and prions. Specific organisms in these classes are well known (see, for example, Davis et al., Microbiology, 3 rd edition, Harper & Row, 1980, and Stanier et al., The Microbial World, 5th edition, Prentice Hall, 1986). Infections of interest that may be treated or prevented according to the subject methods include, but are not limited to, toxic shock syndrome, diphtheria, cholera, typhus, meningitis, whooping cough, botulism, tetanus, pyogenic infections, sinusitis, pneumonia, gingivitis, mucitis, folliculitis, cellulitis, acne and acne vulgaris, impetigo, osteomyelitis, endocarditis, ulcers, burns, dysentery, urinary tract infections, gastroenteritis, anthrax, Lyme disease, syphilis, rubella, septicemia, Buruli ulcer, mycetoma, chromoblastomycosis, vaginal candidiasis, tuberculosis, otitis media, eczema (atopic dermatitis), diabetic ulcers, impetigo, toenail fungus, venous ulcers, infected burns, infected wounds, infected ballistic wounds and plague; as well as primary, secondary, and opportunistic infections associated with, for example, trauma, surgery, endotracheal intubation, tracheostomy, and cystic fibrosis.

A subject may have other clinical indications that have associated infection or inflammation treatable or preventable with the compositions and methods of the present invention, which include without limitation those associated with implantable, indwelling, or similar medical devices, such as intravascular catheters (e.g., intravenous and intraarterial), right heart flow-directed, catheters, Hickman catheters, arteriovenus fistulae, catheters used in hemodialysis and peritoneal dialysis (e.g., silastic, central venous, Tenckhoff, and teflon catheters), vascular access ports, indwelling urinary catheters, urinary catheters, silicone catheters, ventricular catheters, synthetic vascular prostheses (e.g., aortofemoral and femoropopliteal), prosthetic heart valves, prosthetic joints, orthopedic implants, penile implants, shunts (e.g., Scribner, Torkildsen, central nervous system, portasystemic, ventricular, ventriculoperitoneal), intrauterine devices, tampons, contact lenses, dental implants, ureteral stents, pacemakers, implantable defibrillators, tubing, cannulas, probes, blood monitoring devices, needles, and the like. A "medical device" refers to any device for use in a subject, such as an animal or human.

The amount of the subject peptide composition administered can be determined using any convenient methods to be an amount sufficient to produce the desired effect in association with a pharmaceutically acceptable diluent, carrier or vehicle. The specifications for the unit dosage forms of the present disclosure will depend on the particular compound employed and the effect to be achieved, and the pharmacodynamics associated with each compound in the host.

The antimicrobial polypeptide(s) can be administered at a dose and frequency that depends on the type of animal, the size of the animal, and the condition being treated. It should also be understood that a specific dosage and treatment regimen for any particular patient will depend upon a variety of factors, including the activity of the specific compound employed, the mode of administration, the age, body weight, general health, gender, diet, rate of excretion, drug combination, and the judgment of the treating physician, the condition being treated and the severity of the condition. Such dosage may be ascertained readily by a person skilled in the art. This dosage regimen may be adjusted to provide the optimal therapeutic response. In some cases, the antimicrobial polypeptide is administered daily (or every other day, or weekly), in an amount between about 1 mg and about 1000 mg (e.g., about 5 mg to about 900 mg, about 5 mg to about 800 mg, about 5 mg to about 700 mg, about 5 mg to about 600 mg, about 10 mg to about 500 mg, about 10 mg to about 400 mg, about 10 mg to about 300 mg, about 10 mg to about 250 mg, about 10 mg to about 200 mg, about 10 mg to about 150 mg, about 10 mg to about 100 mg, about 50 mg to about 500 mg, about 50 mg to about 400 mg, about 50 mg to about 300 mg, about 50 mg to about 250 mg, about 50 mg to about 200 mg, about 50 mg to about 150 mg, about 50 mg to about 100 mg, about 75 mg to about 500 mg, about 75 mg to about 400 mg, about 75 mg to about 300 mg, about 75 mg to about 250 mg, about 75 mg to about 200 mg, about 75 mg to about 150 mg, about 75 mg to about 100 mg, about 100 mg to about 500 mg, about 100 mg to about 400 mg, about 100 mg to about 300 mg, about 100 mg to about 250 mg, about 100 mg to about 200 mg, or any other range containing two of the foregoing endpoints). The daily dose can be administered once during the day, or broken up into smaller doses that are taken at multiple time points during the day. For a human (and other similarly-sized mammals), a dose of 5 mg/kg every other day can be administered. The antimicrobial polypeptide can be administered for a fixed period of time (e.g., for 2-3 weeks), at intervals (e.g., administer polypeptide for 2-3 weeks, wait 2-3 weeks, then repeat the cycle), or until such time as the microbial organism has been eliminated or significantly reduced, the symptoms of the microbial infection have been ameliorated, or the potential microbial infection risk has been reduced o eliminated (e.g., a wound has healed).

For intrapulmonary administration, a patient can receive a dose of about 0.01 to 10 mg/kg/day of the peptide ±20% or ±10%. This dose can be administered by at least one, preferably several "puffs" from an aerosol device. The total dose per day is preferably administered at least once per day, but may be divided into two or more doses per day. Some patients may benefit from a period of "loading" the patient with the subject peptide with a higher dose or more frequent administration over a period of days or weeks, followed by a reduced or maintenance dose.

The administration of the antimicrobial polypeptides (or pharmaceutical compositions comprising such polypeptides) in conjunction with any of the foregoing methods can be performed intravenously, intraperitoneally, parenterally, orthotopically, subcutaneously, topically, via inhalation, nasally, orally, sublingually, intraocularly, by means of an implantable depot, using nanoparticle-based delivery systems, microneedle patch, microspheres, beads, osmotic or mechanical pumps, and/or other mechanical means. In some embodiments, the pharmaceutical compositions of the invention can be administered to a subject by applying the composition to a surface of a medical device prior to inserting the medical device into the subject. Systemic administration can be achieved via intravenous, intramuscular or subcutaneous injections or infusions. In certain cases, the subject peptide compositions are administered orally. In certain instances, the subject peptide compositions are administered via inhalation. In some cases, the subject peptide compositions are administered topically.

One aspect of the present disclosure is to provide methods for treating or preventing a infection of the eye by any pathogen of interest (e.g., as described herein), such as a viral or bacterial infection. In some embodiments, the methods comprise administering a pharmaceutically acceptable composition to the ocular region of a subject. Any convenient ophthalmic delivery route can be utilized in conjunction with the subject methods and compositions, including but not limited to, topical instillation, subconjunctival, subtenon, intravitreal, retrobulbar, and intracameral administration. For example, the composition may be topically applied (e.g. as eye drops, via a hydrophilic hydrogel contact lens, or via an ocular polymer insert for topical application) to the eye. The pharmaceutically acceptable composition comprises a pharmaceutically acceptable carrier and at least one peptide as described herein. In another embodiment, the composition may be orally administered to the subject. Intraocular administration of a subject ophthalmic composition can be achieved via subconjunctival (into the subconjunctival), intravitreal (into the vitreous), subretinal (under the retina), or retrobulbar (behind the eyeball) injection.

The eye infections described herein may be any applicable pathogen that can infect the eye, such as bacteria, fungi and viruses. Exemplary infections include, but are not limited to, bacterial conjunctivitis (e.g., caused by *Haemophilus influenza, Streptococcus pneumoniae* or *Staphylococcus aureus*), Gonococcal conjunctivitis, Chlamydial conjunctivitis, fungal keratitis, trachoma, bacterial endophthalmitis, bacterial keratitis, and the like.

The viral infection described herein may be any applicable virus that can infect the eye, such as viral keratitis. Exemplary viral infections include, but are not limited to, viral conjunctivitis, influenza, herpes simplex virus (HSV), human herpes virus, cytomegalovirus (CMV), Epstein-Barr virus (EBV), varicella zoster virus (VZV), orthopox virus, variola major and minor, vaccinia, cowpox, camelpox, monkeypox, papilloma virus, adenovirus, polyoma virus including JC virus, BK virus, SV40 and a combination thereof. In some embodiments, at least one viral infection is selected from cytomegalovirus, varicella zoster virus, adenovirus, herpes simplex virus and Epstein-Barr virus. In another embodiment, the viral infection is a topical viral infection.

Another aspect of the invention is to provide methods for treatment or preventing a posterior ocular condition. In some embodiments, posterior ocular condition or degeneration condition of retina or retinal nerve, is selected from macular degeneration, retinopathy, or retinitis pigmentosa. Further, in one embodiment, the pharmaceutical composition for treating posterior ocular condition is intraocular administered (for example, intraocular injection including retrobulbar, intravitreal, intraretinal, intracameral or subconjunctival injection).

Infection is the predominant determinant of wound healing, incidence of complications, and outcome of burn patients. The main organisms responsible are *Pseudomonas aeruginosa, S. aureaus, Streptococcus pyogenes*, and various gram-negative organisms. Frequent debridements and establishment of an epidermis or a surrogate, such as a graft or a skin substitute, is essential for prevention of infection. In some cases, the subject peptide composition, alone or in combination with antibiotic and/or anti-inflammatory agents, is applied to burn wounds as a gel, ointment or cream, and/or administered systemically. Topical application can prevent systemic infection following superficial colonization or eradicate a superficial infection. In some cases, the subject composition can be administered as a 0.5% to 5% gel, cream, or ointment, such as 0.5 to 2%, as described herein. Application to the skin could be performed once a day or as often as dressings are changed. Systemic administration can be achieved via intravenous, intramuscular or subcutaneous injections or infusions. Other routes of administration can also be used.

The compositions and methods of the present disclosure also find use in the treatment of nosocomial infections. For example, infection by *S. aureus* may result in impetigenous lesions or infected wounds and is associated with increased infection rates following cardiac surgery, hemodialysis, orthopedic surgery and neutropenia, both disease-induced and iatrogenic. Nasal and extra-nasal carriage of Staphylococci spp. can result in hospital outbreaks of the same Staphylococci strain that is colonizing a patient's or a hospital worker's nasal passage or extra-nasal site.

The compositions and methods of the present disclosure also find use in the treatment of acute bacterial skin and skin structure infections (ABSSSI). Also of interest are methods of treating gram-negative pathogens and multidrug-resistant gram-positive bacteria, such as community-acquired methicillin resistant *Staphylococcus aureus* (MRSA). Gram-negative bacteria of interest that may be targeted according to the subject methods include, but are not limited to, *A. baumannii* and *P. aeruginosa*; gram-positive bacteria, *S. aureus* and MRSA and fungal strains; *C. albicans, C. parapsilosis, C. krusei, Aspergillus fumigatus, Aspergillus flavus, Absidia corymbifera, Fusarium solani* and *Mucor*.

In some case, the subject being treating according to the subject methods is infected with an antibiotic-resistant microorganism selected from a gram positive bacterium, a gram negative bacterium, a biofilm-forming bacterium, *Streptococcus pneumoniae, Campylobacter, Neisseria gonorrhoeae, Salmonella*, Methicillin-resistant *Staphylococcus aureus* (MRSA), *Shigella*, Vancomycin-resistant *Enterococcus* (VRE), Vancomycin-resistant *Staphylococcus aureus* (VRSA), Erythromycin-resistant Group A *Streptococcus*, Clindamycin-resistant Group B *Streptococcus*, Carbapenem-resistant Enterobacteriaceae (CRE), drug-resistant tuberculosis, Extended spectrum Enterobacteriaceae (ESBL), multidrug-resistant *Acinetobacter* (including MRAB), *Clostridium difficile*, Enteropathogenic *E. coli* (EPEC), *Pseudomonas aeruginosa, H. pylori, Streptococcus anginosus* and Uropathogenic *E. coli* (UPEC), *S. epidermidis, E. faecalis, E. coli, S. aureus, Campylobacter*, and *Pseudomonas* or combinations thereof.

The compositions and methods of the present disclosure also find use in the treatment or inhibition of a biofilm. "Inhibition" or "inhibiting" of biofilm formation refers to a decrease of biofilm associated microorganism formation and/or growth. The subject compositions are effective against biofilms produced by a wide range of microbial species including, but not limited to, *S. epidermidis, E. faecalis, E. coli, S. aureus, Campylobacter* spp. *H. pylori* and *Pseudomonas*, alone, or in combination. The biofilm can be associated with a bacterial infection selected from impetigo, boils, abscesses, folliculitis, cellulitis, necrotizing fasciitis, pyomyositis, surgical/traumatic wound infection, and infected ulcers and burns, osteomyelitis, device-related osteoarticular infections, impetigo, secondarily infected skin lesions, meningitis, brain abscess, subdural empyema, spinal epidural abscess, arterial damage, gastritis, urinary tract infections, biliary tract infections, pyelonephritis, cystitis, sinus infections, ear infections, otitis media, otitis externa, leprosy, tuberculosis, conjunctivitis, bloodstream infections, benign prostatic hyperplasia, chronic prostatitis, lung infections, osteomyelitis, catheter infections, bloodstream infections, skin infections, acne, rosacea, dental caries, periodontitis, gingivitis, nosocomial infections, arterial damage, endocarditis, periprosthetic joint infections, open or chronic wound infections, venous stasis ulcers, diabetic ulcers, arterial leg ulcers, pressure ulcers, endocarditis, pneumonia, orthopedic prosthesis and orthopedic implant infections, peritoneal dialysis peritonitis, cirrhosis, and other acute or chronic infection that involves or possesses a biofilm.

In some embodiments, the subject antimicrobial peptide has anti-inflammatory activity. The present disclosure also provides a method of treating a condition associated with cancer. Cancers of interest include solid tumor cancers. In such methods, a pharmaceutical composition including a subject peptide (e.g., as described herein) can be administered locally at a site of interest, e.g., intra-tumorally via injection, or the like.

In conjunction with any of the foregoing methods, the antimicrobial polypeptides (or pharmaceutical compositions comprising such polypeptides) can be administered in combination with another drug, e.g., an antibiotic, antiviral, antifungal, antiprotozoal, antimalarial, or a drug for treating a non-infectious disease or other condition. In certain embodiments, the other drug is one that can reduce a symptom of a disease/microbial infection (e.g., to reduce or prevent a fever, to treat or prevent nausea, etc.). In each case, the antimicrobial polypeptide can be administered prior to, at the same time as, or after the administration of the other drug.

As noted above, the subject antimicrobial peptides may be used in a synergistic combination with an additional antimicrobial agent. Antibacterial agents of interest include, but are not limited to, penicillins, cephalosporins, carbacephems, cephamycins, carbapenems, monobactams, aminoglycosides, glycopeptides, quinolones, tetracyclines, macrolides, and fluoroquinolones. Examples of antibiotic agents include, but are not limited to, Penicillin G (CAS Registry No.: 61-33-6); Methicillin (CAS Registry No.: 61-32-5); Nafcillin (CAS Registry No.: 147-52-4); Oxacillin (CAS Registry No.: 66-79-5); Cloxacillin (CAS Registry No.: 61-72-3); Dicloxacillin (CAS Registry No.: 3116-76-5); Ampicillin (CAS Registry No.: 69-53-4); Amoxicillin (CAS Registry No.: 26787-78-0); Ticarcillin (CAS Registry No.: 34787-01-4); Carbenicillin (CAS Registry No.: 4697-36-3); Mezlocillin (CAS Registry No.: 51481-65-3); Azlocillin (CAS Registry No.: 37091-66-0); Piperacillin (CAS Registry No.: 61477-96-1); Imipenem (CAS Registry No.: 74431-23-5); Aztreonam (CAS Registry No.: 78110-38-0); Caphalothin (CAS Registry No.: 153-61-7); Cefazolin (CAS Registry No.: 25953-19-9); Cefaclor (CAS Registry No.: 70356-03-5); Cefamandole formate sodium (CAS Registry No.: 42540-40-9); Cefoxitin (CAS Registry No.: 35607-66-0); Cefuroxime (CAS Registry No.: 55268-75-2); Cefonicid (CAS Registry No.: 61270-58-4); Cefmetazole (CAS Registry No.: 56796-20-4); Cefotetan (CAS Registry No.: 69172-56-7); Cefprozil (CAS Registry No.: 92665-29-7); Loracarbef (CAS Registry No.: 121961-22-6) Cefetamet (CAS Registry No.: 65052-63-3); Cefoperazone (CAS Registry No.: 62893-19-0); Cefotaxime (CAS Registry No.: 63527-52-6); Ceftizoxime (CAS Registry No.: 68401-81-0) Ceftriazone (CAS Registry No.: 73384-59-5); Ceftazidime (CAS Registry No.: 72558-82-8); Cefepime (CAS Registry No.: 88040-23-7); Cefixime (CAS Registry No.: 79350-37-1); Cefpodoxime (CAS Registry No.: 80210-62-4); Cefsulodin (CAS Registry No.: 62587-73-9); Fleroxacin (CAS Registry No.: 79960-72-3); Nalidixic acid (CAS Registry No.: 389-08-2); Norfloxacin (CAS Registry No.: 70458-96-7); Ciprofloxacin (CAS Registry No.: 85721-33-1); Ofloxacin (CAS Registry No.: 82419-36-1); Enoxacin (CAS Registry No.: 74011-58-8); Lomefloxacin (CAS Registry No.: 98079-51-7); Cinoxacin (CAS Registry No.: 28657-80-9); Doxycycline (CAS Registry No.: 564-25-0); Minocycline (CAS Registry No.: 10118-90-8); Tetracycline (CAS Registry No.: 60-54-8); Amikacin (CAS Registry No.: 37517-28-5); Gentamicin (CAS Registry No.: 1403-66-3); Kanamycin (CAS Registry No.: 8063-07-8); Netilmicin (CAS Registry No.: 56391-56-1); Tobramycin (CAS Registry No.: 32986-56-4); Streptomycin (CAS Registry No.: 57-92-1); Azithromycin (CAS Registry No.: 83905-01-5); Clarithromycin (CAS Registry No.: 81103-11-9); Erythromycin (CAS Registry No.: 114-07-8); Erythromycin estolate (CAS Registry No.: 3521-62-8); Erythromycin ethyl succinate (CAS Registry No.: 41342-53-4); Erythromycin glucoheptonate (CAS Registry No.: 23067-13-2); Erythromycin lactobinate (CAS Registry No.: 3847-29-8); Erythromycin stearate (CAS Registry No.: 643-22-1); Vanomycin (CAS Registry No.: 1404-90-6); Teicoplanin (CAS Registry No.: 61036-64-4); Chloramphenicol (CAS Registry No.: 56-75-7); Clindamycin (CAS Registry No.: 18323-44-9); Trimethoprim (CAS Registry No.: 738-70-5); Sulfamethoxazole (CAS Registry No.: 723-46-6); Nitrofurantoin (CAS Registry No.: 67-20-9); Rifampin (CAS Registry No.: 13292-46-1); Mupirocin (CAS Registry No.: 12650-69-0); Metronidazole (CAS Registry No.: 443-48-1); Cephalexin (CAS Registry No.: 15686-71-2); Roxithromycin (CAS Registry No.: 80214-83-1); Co-amoxiclavunate; combinations of Piperacillin and Tazobactam; and their various salts, acids, bases, and other derivatives, and combinations thereof.

The subject antimicrobial peptide may also be used in combination with an anti-fungal agents. Exemplary anti-fungal agents of interest include, but are not limited to, terbinafine hydrochloride, nystatin, amphotericin B, griscofulvin, ketoconazole, miconazole nitrate, flucytosine, fluconazole, itraconazole, clotriamzole, benzoic acid, salicylic acid, and selenium sulfide.

The subject antimicrobial peptide may also be used in combination with an anti-viral agent. Exemplary anti-viral agents of interest include, but are not limited to, amantadine hydrochloride, rimantadin, acyclovir, famciclovir, foscarnet, ganciclovir sodium, idoxuridine, ribavirin, sorivudine, trifluoridine, valacyclovir, vidarabin, didanosine, stavudine, zalcitabine, zidovudine, interferon alpha, and edoxudine.

The subject antimicrobial peptide may also be used in combination with an anti-parasitic agent. Exemplary anti-parasitic agents of interest include, but are not limited to, pirethrins/piperonyl butoxide, permethrin, iodoquinol, metronidazole, diethylcarbamazine citrate, piperazine, pyrantel pamoate, mebendazole, thiabendazole, praziquantel, albendazole, proguanil, quinidine gluconate injection, quinine sulfate, chloroquine phosphate, mefloquine hydrochloride, primaquine phosphate, atovaquone, co-trimoxazole (sulfamethoxazole/trimethoprim) and pentamidine isethionate.

The subject compounds can find use in a variety of research applications including the identification and testing of candidate compounds (e.g., for pharmaceutical development) and performing research on disease conditions of interest in which a target microbe is implicated. Research applications of interest can involve use of the subject compounds in a variety of in vitro assays including high throughput screening assays, potency assays, and competitive inhibition assays where the subject peptides can be useful as a control compound or as a tool in the investigation the sample of interest.

Definitions

It is to be understood that this invention is not limited to particular embodiments described herein, which as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are described herein.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The present disclosure provides antimicrobial polypeptides, sometimes referred to as "RP peptides," that satisfy one or more of the structural formulae or sequences described herein. The present disclosure also provides antimicrobial polypeptides that share a minimum degree of homology (e.g., as described herein) with any of the exemplary RP peptides disclosed herein. Thus, a peptide or polypeptide of the present disclosure is an antimicrobial polypeptide that satisfies one of the formulae described herein or shares a minimum degree of homology with any of the exemplary RP peptides disclosed herein.

The term "antimicrobial" refers to the ability of a compound, i.e. a subject peptide, to decrease the population of microscopic flora and/or fauna in an environment or sample. Antimicrobial activity includes bacteriostatic or antibacterial activity, antifungal activity, antialgal activity, and the like. An antimicrobial need not eliminate all microbes, but simply decreases the viable population on the treated surface. Similarly, "antimicrobial activity" refers to the ability of a compound to inhibit or irreversibly prevent the growth of a microorganism. Such inhibition or prevention can be through a microbicidal action or microbistatic inhibition. "Microbicidal inhibition" refers to the ability of the antimicrobial to kill or irrevocably damage the target organism. "Microbistatic inhibition" refers to the ability of the microbistatic or antimicrobial compound to inhibit or to retard the growth of the target organism without causing death. Microbicidal or microbistatic inhibition can be applied to either an environment presently exhibiting microbial growth (i.e., therapeutic treatment) or an environment at risk of supporting such growth (i.e., prevention or prophylaxis).

"Biofilm" refers any group of microorganisms in which cells stick to each other on a surface.

The terms "peptide" and "polypeptide" are used interchangeably to refer to polymers constructed from amino acid residues.

The term "amino acid residue," as used herein, refers to any naturally occurring amino acid, non-naturally occurring amino acid, or amino acid mimetic (such as a peptoid monomer). An amino acid residue can be in an L- or D-form.

The "length" of a polypeptide is the number of amino acid residues linked end-to-end that constitutes the polypeptide, excluding any non-peptide linkers and/or modifications that the polypeptide may contain.

In certain embodiments of the antimicrobial polypeptides described herein, a numbering scheme is utilized for convenience and simplicity to refer to particular positions in the structure and/or sequence of the compounds, e.g., positions at which particular variant amino acid residues of interest are incorporated into the polypeptide motif. This numbering scheme is based on a sequential order of amino acid residues in order to assign a numbered location to an amino acid residue of interest, e.g., a location in a motif or a structural model as described herein. By way of example, an antimicrobial peptide of the sequence FIOKFAKOFKOFIOKFAK (SEQ ID NO: 55), may be described and numbered according to the following scheme: $F^1I^2O^3K^4F^5A^6K^7O^8F^9K^{10}O^{11}F^{12}I^{13}O^{14}K^{15}F^{16}A^{17}K^{18}$ (SEQ ID NO: 55). It is understood that the numbering of a sequence is not meant to be limiting on the length of a subject antimicrobial peptide and that one or more additional amino acid residues and/or terminal modifications may be included at the N-terminal and/or C-terminal of a numbered sequence. b In certain instances, the subject antimicrobial peptides can include cross-linking residues (e.g., cysteine residues capable of disulfide formation) and/or bubble regions, e.g., a region as described herein flanked by cysteine residues and/or linking residue(s), such as glycine residue(s). In such examples, the cross-linking residues are generally not included in the sequential numbering of the polypeptide motif, but may include their own separate numbering system. By way of example the antimicrobial peptide of the sequence RFCWKVCYKGICFKKCK (RP557, SEQ ID NO: 8) which includes 4 cysteine residues, may be numbered according to the following scheme: $R^1F^2$-$C^1$-$W^3K^4V^5$-$C^2$-$Y^6K^7G^8I^9$-$C^3$-$F^{10}K^{11}K^{12}$-$C^4$-$K^{13}$ (RP557, SEQ ID NO: 8). It is understood that cross-linking residues (e.g., cysteine residues) that are included in a subject peptide may capable of forming an intramolecular. In some cases, the cross-linking residue is a cysteine residue that is capable of forming a disulfide bond with another.

A "linker" or "linker sequence" can be any moiety that links two peptide sequences together. In some embodiments, a linker is an amino acid sequence that is co-linear with the peptide sequences being linked together, whereas in other embodiments a linker is a separate moiety that is attached to the two peptide sequences, e.g., via a covalent linkage. Linkers can be amino acid sequences or be non-amino acid moieties. In certain embodiments, a linker is used to facilitate dimerization of two amphipathic regions.

"Pharmaceutically acceptable" as used herein refers to those compounds, materials, compositions, and/or dosage forms which are, within the scope of sound medical judgment, suitable for use in contact with the tissues of human beings and animals (such as one or more of the animal "patients" or "subjects" as discussed above) without excessive toxicity, irritation, allergic response, or other problems or complications commensurate with a reasonable benefit/risk ratio. "Pharmaceutically acceptable salt", as used herein, refers to derivatives of the compounds defined herein, wherein the parent compound is modified by making acid or base salts thereof.

EXAMPLES

The following examples are put forth so as to provide those of ordinary skill in the art with a complete disclosure and description of how to make and use the present invention, and are not intended to limit the scope of what the inventors regard as their invention, nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

General Methods of Assessing Peptides

Example 1: Activity Against Planktonic Gram-Negative and Gram-Positive Bacteria

Peptides are tested against the following challenge organisms by the M11-A8E CLSI standard for Antimicrobial Susceptibility Testing of Anaerobic Bacteria: *Enterococcus faecium* ATCC 700221; *Enterobacter* aerogens ATCC 13048; *Staphylococcus aureus* MRSA ATCC 33591; *Streptococcus pneumoniae* ATCC 49619; *Pseudomonas aeruginosa* ATCC 27853; *Acinetobacter baumannii* ATCC 17978D-5; *Pseudomonas aeruginosa* ATCC 19660; and *Staphylococcus epidermidis* ATCC 51625. Sample dilutions range from initial sample to 1:2048. Eleven (11) concentrations are tested in duplicate on a 96 well plate by MQA Laboratories. Results are shown as Minimum bactericidal concentration (MBC), which is the concentration of each peptide necessary to yield 99.9% lethality for each of the eight challenge organisms.

Example 2: Activity Against Biofilm Bacteria

The Minimum Biofilm Eradication Concentration (MBEC) Assay is used. MBEC values provide estimates on the concentration of an antimicrobial product required to kill biofilm bacteria. The Calgary Biofilm Device (CBD) plate is used to effect biofilm formation on a lid containing 96 pegs. Bacterial cultures are grown and diluted in Tryptic Soy Broth (TSB) to approximately $1 \times 10^7$ CFU/mL before inoculation of the CBD plate, which are then incubated for 24 hr at 35° C. on a shaker at 125 rpm.

The peg lid containing biofilm is first rinsed in PBS to remove planktonic cells prior to treatment with 2-fold serial dilutions of test articles and control overnight at 35° C. The peg lid is rinsed in PBS twice before sonication in fresh media to disrupt biofilm adhered to the pegs. The plate is then incubated overnight to evaluate growth. Bacterial quantification is performed by measuring absorbance at 650 nm (A650). By definition, A650 reading of less than 0.1 indicates biofilm eradication.

Example 3: Activity Against Biothreat Bacteria (*B. thailandensis*)

In vitro activity of the Test Articles and comparator antibiotic (ceftazidime) are tested as follows: in a sterile 96-well plate, $1 \times 10^5$ CFU per well of bacteria are incubated with serial dilutions of antibiotic (control) and peptide in 10 mM phosphate buffer (3 h, 37° C.). Bacterial survival is determined by serial dilution at each peptide concentration in sterile PBS. Dilutions are plated in triplicate on nutrient agar and incubated at 37° C. for 24 h; colonies are then counted to determine survival. Bacterial survival is calculated by the ratio of the number of colonies on each experimental plate to the average number of colonies in the control plates lacking any antimicrobial peptide. The antimicrobial peptide concentration required to kill 50% of *B. thailandensis* (EC50) is determined by graphing percent survival versus log of peptide concentration. EC50 is determined by fitting the data to a standard sigmoidal dose-response curve. Each experiment was performed with three replicates.

Example 4: Antibacterial and Antifungal Activity of Selected Peptides (IC50 Values)

Measurement of antimicrobial and anti-fungal activity is determined by a standard micrometer dilution method. Briefly, cells are grown overnight in media specified for each strain, and are diluted in the same media. Serial dilutions of the peptides are added to microtiter plates in a volume of 50 ul, followed by the addition of 50 ul of bacteria or fungi, $5 \times 10^5$ CFU/ml. Plates are incubated at 37 degrees for 24 hours and the Minimum Inhibitory Concentrations (MICs) are determined as the lowest peptide concentration that inhibited 50% of bacterial growth.

Example 5: Screening of Peptides for In Vitro Bactericidal Activity

Bacteria tested included *Burkholderia cepacia* strain Toronto (B.c.), *Porphyromonas gingivalis* strains A7436 and HG405, *Actinobacillus actinomycetemcomitans* strain A7154 (A.a.), *Fusobacterium nucleatum* strain 1594 (F.n.), *Escherichia coli* strain (E.c.), *Staphylococcus aureus* ATCC strain 29213 (S.a.), and *Pseudomonas aeruginosa* strain (P.a.). All bacteria are grown in appropriate media under appropriate atmosphere to the early exponential phase of growth. Media are inoculated with a dose of bacteria to assure a minimum of five doublings before harvesting. The cultures are washed twice in saline by centrifugation and resuspended in saline at suitable concentration. In the initial screening, all peptides are used at a final concentration of 10M in saline with the target bacteria at $10^6$ CFU/ml as estimated by optical density at 660 nm. Controls are treated with an equal volume of saline. The suspensions are incubated at 37° C. in ambient atmosphere and aliquots removed temporally (0 to 2 hrs) for quantitative recovery of colony forming units. This allows determination of the kinetics of killing of the individual peptides with the different bacterial strains. Killing is considered significant if there is greater than a one-log reduction in recoverable CFU in the peptide-treated vs. the saline-treated control. Peptides that failed to kill at 10 μM are considered inactive. Any peptide that results in greater than two logs reduction is titrated by either two-fold, five-fold or ten-fold dilutions prior to testing with $10^6$ CFU/ml of the target bacteria. The endpoint titration is determined as the last concentration of peptide (in μM) that gives greater than two-logs reduction in recoverable CFU vs. the saline-treated control ("Two-log Reduction Concentration").

Example 6: Killing of Antibiotic Resistant Bacteria

*Staphylococcus aureus*, *Pseudomonas aeruginosa*, and *Clostridium difficile* are tested for their sensitivity to exemplary subject antimicrobial polypeptides. These organisms are associated with hospital-acquired infections. The experiments are performed as described in Example 5.
Assessment of Activity of Antimicrobial Peptides

Example 7: Synthesis and Evaluation of Peptides

Antimicrobial peptides (AMPs) were designed based on sequences found in naturally occurring AMPs. The subject AMPs are amphipathic cationic peptides with the ability to kill microbes by disrupting their membrane function. This mode of action rapidly kills antibiotic resistant microbes, even in biofilm. In general, the bacteria tested did not develop resistance to the subject AMPs.

Thirty-four AMPs were synthesized and evaluated in three iterative rounds. Each AMP was evaluated for antimicrobial potency against 11 strains of bacteria, 7 strains of fungi and their cytotoxicity determined using L929 fibroblasts and human keratinocytes. The AMPs were evaluated for biofilm eradication and ability to induce antimicrobial resistance.

From the in vitro screening assays three AMPs were selected for further evaluation in a qualified porcine burn wound model infected with *P. aeruginosa* and *S. aureus*. Full thickness wounds were created with heated brass rod and 2 cm trephine: approximately 10 minutes after homeostasis, wounds were infected with a 2:2:1 mixture of S. aureus, P. aeruginosa and Fuscobacterium ssp. Treatment of infected wounds began 24 hours post infection to allow for biofilm formation.

Exemplary AMP RP557 is an amphipathic, α-helical molecule having a NP (non-polar hydrophobic face) and a P (polar hydrophilic face). It has 17 amino acids and a hairpin structure formed by two disulfide bonds. The positive charges on the polar surface are capable of interacting with and disrupting the negatively charged phospholipids on the cell membranes of microorganisms.

Exemplary AMP RP557 was prepared in one gram lots at 98% purity or better. RP557 possesses appropriate physiochemical properties: RP557 is hydrophilic, highly soluble, stable at extremes of pH (<4), resistant to proteases and stable in serum (human serum for 72 hrs at 37° C. monitored via LC-MS/MS). Furthermore, advances in solid and solution phase peptide chemistry has enabled Good Manufacturing Practice (GMP) material to be produced rapidly, economically in high yield and purity.

Example 8: RP557 Activity Results

RP557 possesses broad-spectrum antimicrobial activity against multiple clinical isolates of gram-negative bacteria; A. baumannii and P. aeruginosa; gram-positive bacteria, S. aureus and MRSA and fungal strains; C. albicans, C. parapsilosis, C. krusei, Aspergillusfumigatus, Aspergillus flavus, Absidia corymbifera, Fusarium solani and Mucor.

Figure 3A:
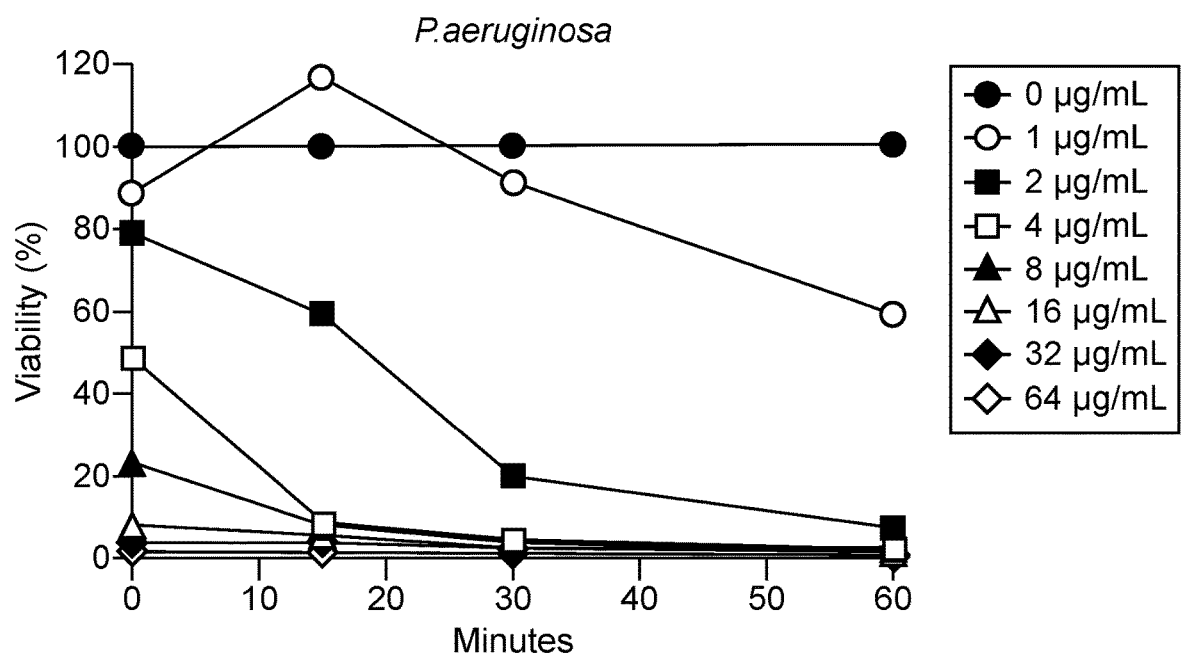
Figure 3B:
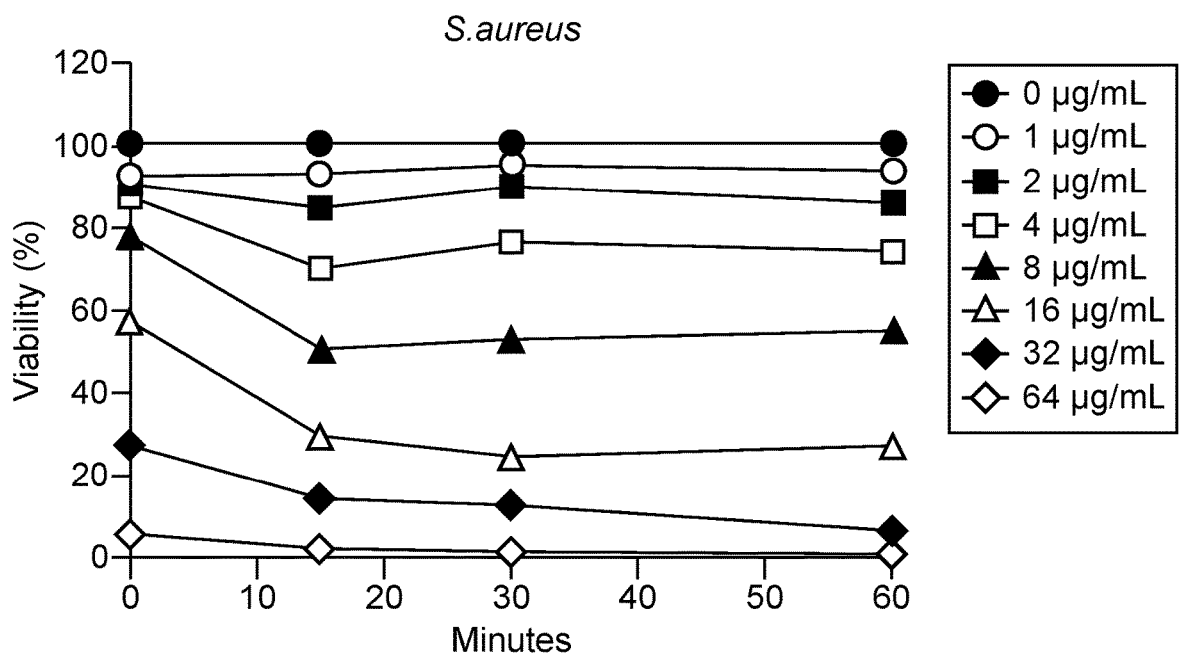

In vitro time-kill assays demonstrated RP557 quickly kills both Gram-positive and Gram-negative bacteria, at low doses (1 to 2 μg/mL) and are not cytotoxic to mammalian cells (FIG. 3). The rapid destruction of pathogenic cells by potent broad-spectrum topical anti-infectives infer a theoretical reduced likelihood of developing bacterial resistance. FIG. 3A to 3C shows RP557 rapidly eradicates P. aeruginosa and S. aureus with no cytotoxicity to mammalian cells. Cell viability was performed using bioluminescent strains of P. aeruginosa 19660 (FIG. 3A), S. aureus 49525 (FIG. 3B) & L929 fibroblast cells (FIG. 3C) and imaged with the IVIS Lumina system. Data represents the mean of 3 measurements.

Pathogens do not Develop Resistance Against RP557

Neither P. aeruginosa nor S. aureus bacteria become resistant to sub-inhibitory concentrations of RP557 after 30 rounds of selection whereas for the standard antibiotics resistance did develop, as evidenced by gentamicin and clindamycin showing growth at 4096 and 256 times the minimum inhibitory concentration (MIC) after 30 days against P. aeruginosa and S. aureus, respectively (FIG. 4A to 4B). The resistant strains at the end of 30 serial passages were then treated with RP557 and both strains were found to be readily susceptible therefore, there is no cross resistance to RP557 and gentamicin-resistant P. aeruginosa and clindamycin-resistant S. aureus.

FIG. 4A to 4B. P. aeruginosa and S. aureus did not develop resistance against RP557. Sub-inhibitory concentrations of RP557, gentamicin and clindamycin were incubated with P. aeruginosa 27853 and S. aureus 29213 for 24 hours. Bacteria showing growth in the highest concentration were re-passaged in fresh dilutions containing sub-minimum inhibitory concentration (MIC) levels of each component for 30 consecutive passages; means are shown.

Biofilm Inactivation

RP557 prevents and treats biofilms of various bacterial and fungal species found in combat wounds thereby mitigating the influence of infection on healing and regeneration. A representative study of RP557 against Candida albicans, is shown in FIG. 5A to 5B.

Figure 5A:
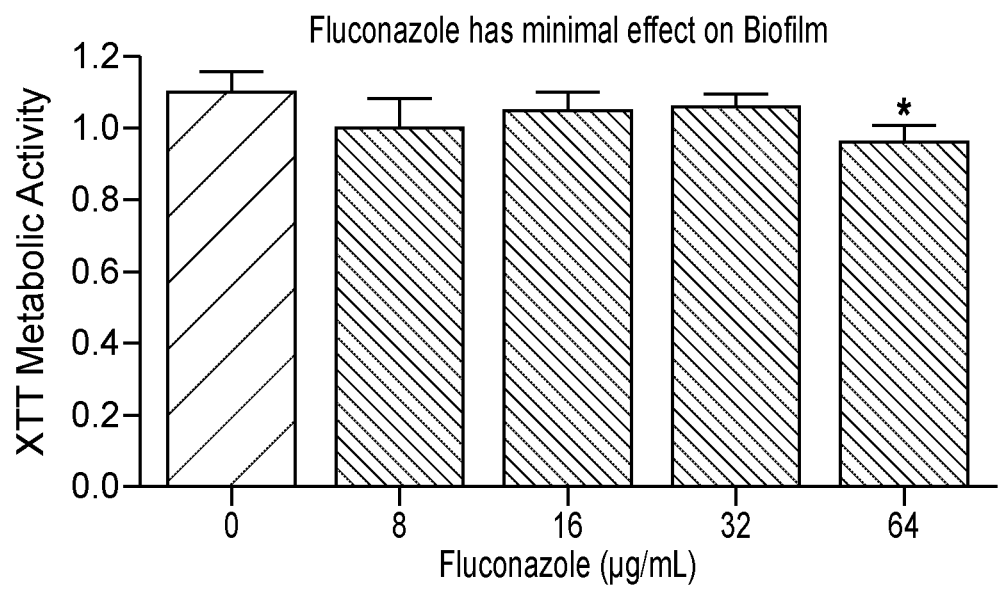
FIG. 5A to 5B show data indicating RP557 is a potent inhibitor of *Candida* biofilm. Fluconazole (FIG. 5A) or RP557 (FIG. 5B) were added to preformed *Candida* 17-88 biofilm for 24 hours and biofilm inhibition evaluated via metabolic evaluation using XTT, 2,3-bis (2-methoxy-4-nitro-5-sulfophenyl) [phenyl-amino)carbonyl]-2H.
Figure 5B:
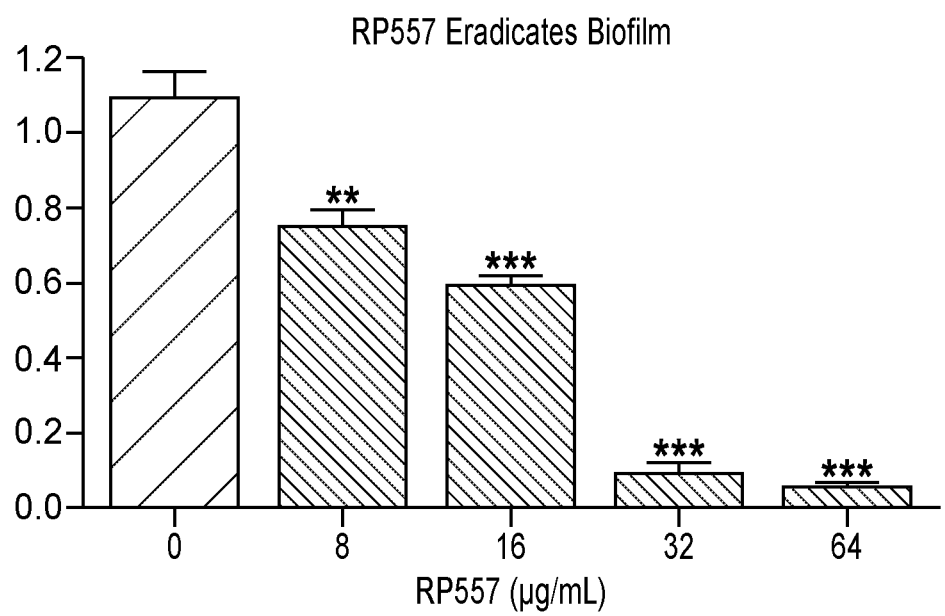

FIG. 5A to 5B: RP557 is a potent inhibitor of Candida biofilm. Fluconazole or RP557 were added to preformed Candida 17-88 biofilm for 24 hours and biofilm inhibition evaluated via metabolic evaluation using XTT, 2,3-bis (2-methoxy-4-nitro-5-sulfophenyl) [phenyl-amino)carbonyl]-2H. Data represent the mean+SD of triplicate measurements and statistical significance, compared to vehicle control, determined by one-way ANOVA followed by Dunnett's test (*p<0.05, p<0.01, and *p<0.001). These results indicate the biofilmn is not resistant to antimicrobial peptides such as RP557

Bactericidal In Vivo Activity

Figure 6A:
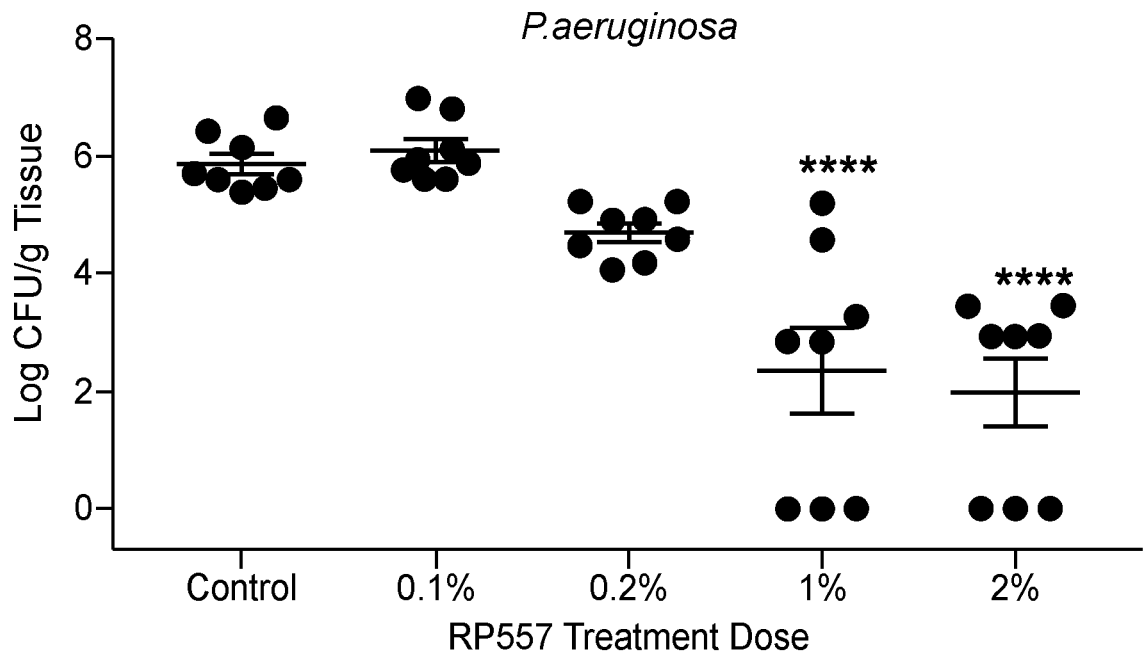
FIG. 6A to 6B shows that topical treatment with exemplary peptide RP557 reduces polymicrobial infection in an infected porcine burn model. Full thickness wounds were created with a heated brass rod and a trephine on the back of anesthetized pigs followed by infection with 2:2:1 mixture of *S. aureus* ATCC 6538 and *P. aeruginosa* (porcine isolate) and *fusobacterium* ssp.
Figure 6B:
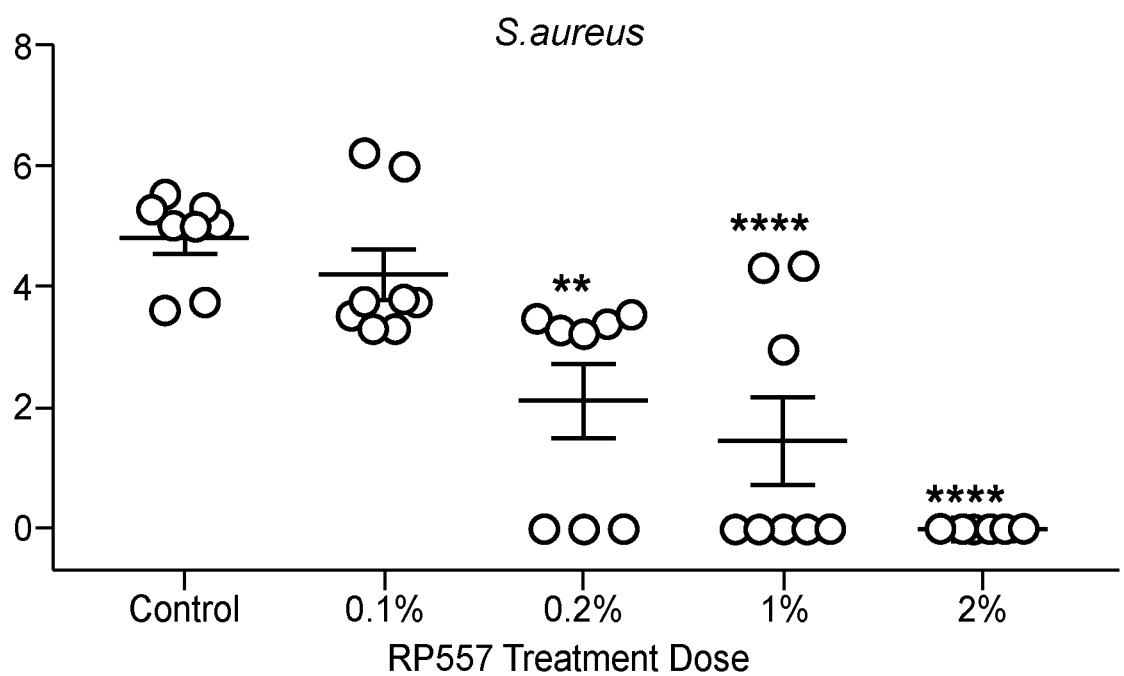

RP557 dose-dependently reduced both P. aeruginosa and S. aureus in a polymicrobial infected full-thickness thermal porcine burn model (FIG. 6A-6B). A single topical application of RP557 reduced S. aureus CFU counts from vehicle control levels of 4.81±0.724 log CFU/g tissue to 4.20±1.19, 2.11±1.75 and 1.46±2.05 log CFU/g tissue for 0.1%, 0.2% (p<0.01) and 1% RP557 (p<0.0001), respectively. Furthermore, a dose of 2% RP557 completely eradicated the S. aureus infection. Moreover, a single RP557 dose reduced the number of viable P. aeruginosa bacteria from 5.87±0.477 log CFU/g tissue to 2.34±2.10 and 1.96±1.64 log CFU/g tissue respectively for 1% (p<0.0001) and 2% (p<0.0001), respectively.

FIG. 6A to 6B shows that topical treatment with exemplary peptide RP557 reduces polymicrobial infection with dose response in an infected porcine burn model. Full thickness wounds were created with a heated brass rod and a trephine on the back of anesthetized pigs followed by infection with 2:2:1 mixture of S. aureus ATCC 6538 (FIG. 6B) and P. aeruginosa (porcine isolate) (FIG. 6A) and fusobacterium ssp. After 3 hours, 0, 0.1, 0.2, 1 or 2% RP557 were applied. After 24 hours, wounds were sampled by punch biopsy and bacterial counts, expressed as log (Colony Forming Units, CFUs/g) evaluated. Data is expressed as mean±SE of 8 replicates. Statistical significance, compared to vehicle, determined by one-way ANOVA followed by Dunnett's test (p<0.01, **p<0.0001).

RP557 Kills Infection Throughout a 24 Hour Period.

Figure 7A:
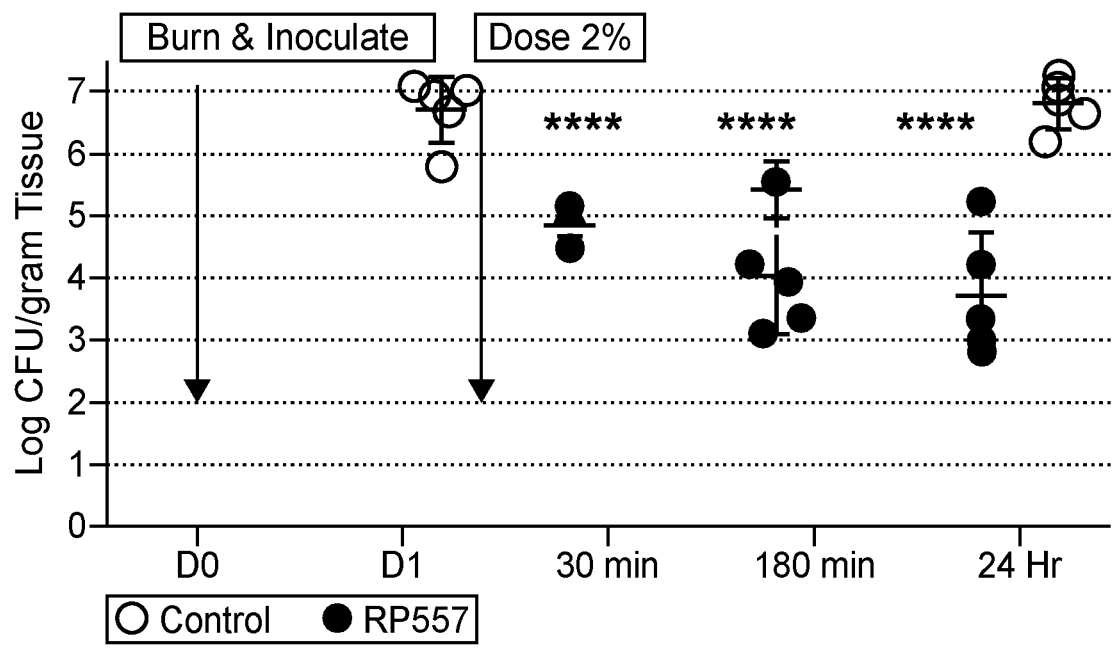
FIG. 7A to 7B show that exemplary peptide RP557 kills infection throughout a 24 hour period. Pharmacodynamic Response to RP557. 24 hours post bacterial inoculation biofilm associated wounds were treated with 2% RP557. Punch biopsies were taken at 30 min, 180 min and 24 hours post treatment, homogenized, plated and CFUs counted.
Figure 7B:
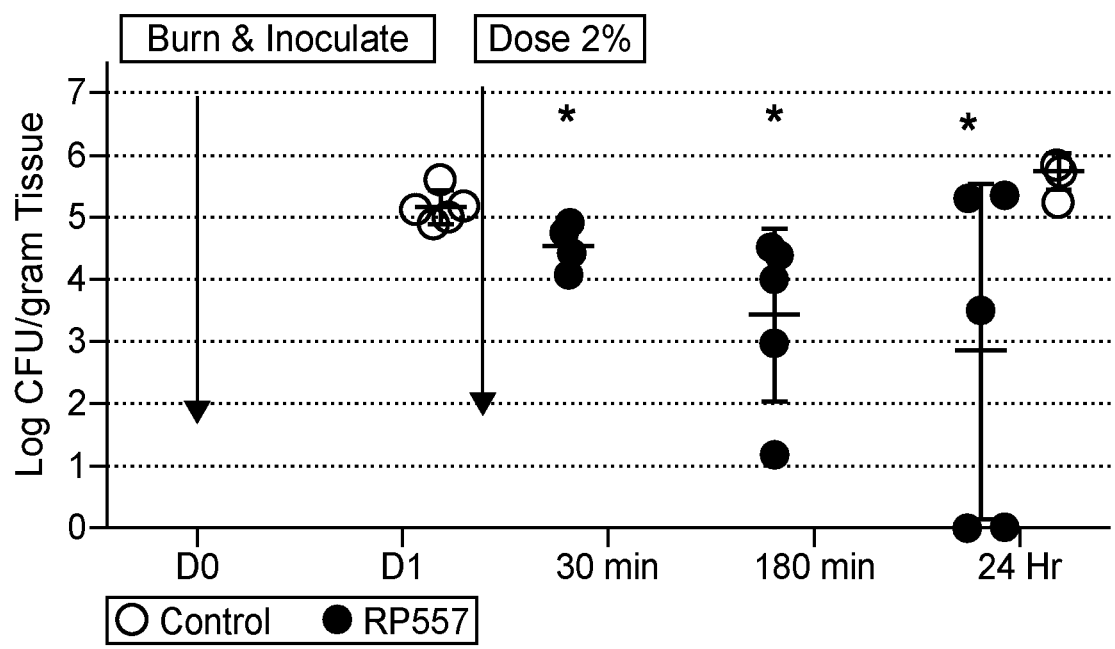

FIG. 7A-7B Pharmacodynamic Response to RP557. Twenty four hours post bacterial inoculation biofilm associated wounds were treated with 2% RP557. Punch biopsies were taken at 30 min, 180 min and 24 hours post treatment, homogenized, plated and CFUs counted. Statistical significance was calculated using the Holm-Sidak method. *p<0.05, *p<0.001, **p<0.0001, dAMP vs Control.

Fungicidal In Vivo Activity

Figure 8A:
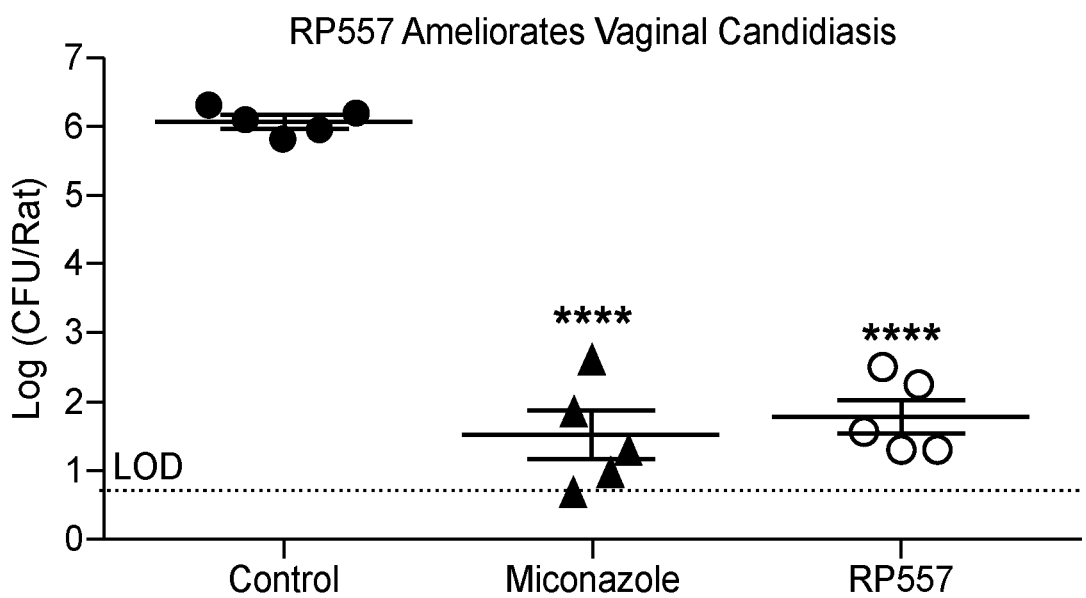
FIG. 8A to 8B indicates topical treatment of exemplary peptide RP557 reduces rodent vaginal candidiasis. Effects of RP557, miconazole and oral fluconazole in a *C. albicans* vaginal infection rodent model. On Day 0, rats were inoculated intravaginally with *C. albicans*. RP557 and miconazole were administered twice daily (FIG. 8A). A separate group received oral fluconazole (FIG. 8B). Further details are provided in the experimental section.
Figure 8B:
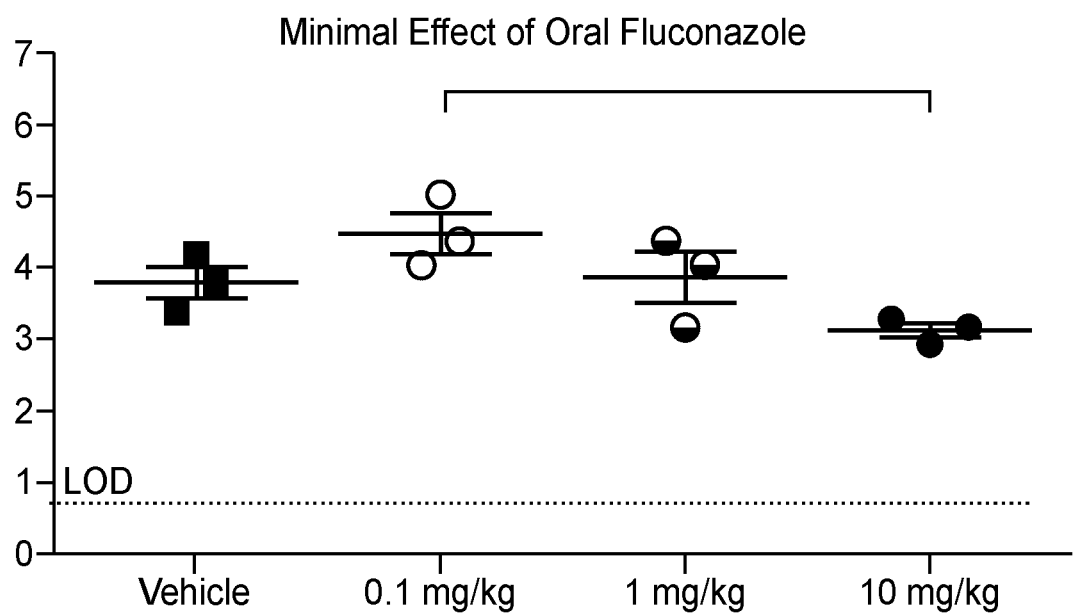

RP557 was effective in eradicating C. albicans in a rodent model of vulvovaginal candidiasis (FIG. 8A-8B). RP557 resulted in significant reductions in fungal counts relative to the vehicle control group (****p<0.0001). Furthermore, the results were more effective than oral fluconazole which exhibited minimal activity.

FIG. 8A to 8B. RP557 topical treatment reduces rodent vaginal candidiasis. Effects of RP557, miconazole and oral fluconazole in the C. albicans (ATCC 44858) vaginal infection rodent model. On Day 0, rats were inoculated intravaginally (IVG) with C. albicans at $1.46 \times 10^7$ CFU/rat. RP557 and miconazole at 20 mg/mL were administered IVG at 0.1 mL/rat twice daily at 8 hr intervals starting from 48 hr after infection for 3 days. CFUs were evaluated on Day 5 with limit of detection (LOD) 0.7 CFU/rat. Significant difference, compared to vehicle, determined by one-way ANOVA followed by Dunnett's test (*p<0.05, ****p<0.0001). A separate group receiving oral fluconazole; *p<0.05 versus 0.1 and 10 mg/kg fluconazole.

The results provided in the Examples demonstrate the efficacy of the antimicrobial peptides of the invention in killing a wide range of microbial organisms, including those that cause medically important human infections.

CLAUSES

Notwithstanding the appended claims, the following clauses are provided to illustrate aspects of the present disclosure.

Clause 1. An antimicrobial peptide, comprising:
a) a peptide sequence selected from RP550-567 (SEQ ID NO: 1 to SEQ ID NO 18);
b) a sequence having at least 80% sequence identity (e.g., at least 85%, at least 90%, or at least 95% sequence identity) with the sequence defined in a); or
c) a sequence having five or less (e.g., four or less, three or less, two or less such as one or two)amino acid substitutions relative to the sequence defined in a), wherein the five or less (e.g., four or less, three or less, two or less such as one or two) amino acid substitutions are substitutions for amino acids according to Table 2 (e.g., a similar amino acid substitution, a conservative amino acid substitution or a highly conservative amino acid substitution).

Clause 2. The antimicrobial peptide of clause 1, comprising:
a) a peptide sequence selected from RP550-567 (SEQ ID NO: 1 to SEQ ID NO 18); or
b) a sequence having five or less (e.g., four or less, three or less, two or less such as one or two)amino acid substitutions relative to the sequence defined in a), wherein the five or less (e.g., four or less, three or less, two or less such as one or two)amino acid substitutions consist of substitution of a cationic amino acid of the sequence with an alternative cationic amino acid residue (e.g., K for O, O for K, K for R, etc.).

Clause 3. The antimicrobial peptide of clause 1, comprising the peptide sequence selected from RP550-567 (SEQ ID NO: 1 to SEQ ID NO 18).

Clause 4. The antimicrobial peptide of clause 1, consisting of the peptide sequence selected from RP550-567 (SEQ ID NO: 1 to SEQ ID NO 18).

Clause 5. The antimicrobial peptide of clause 1, comprising the peptide sequence of formula $7A^1$:

$$X^1J^2\text{-}C^1\text{-}J^3X^4V\text{-}C^2\text{-}YX^7GI\text{-}C^3\text{-}J^{10}X^{11}X^{12}\text{-}C^4\text{-}X^{13} \quad (7A^1)$$
(SEQ ID NO: 47)

Wherein:
$X^1$ is selected from O and R;
$J^2$ and $J^3$ are each independently selected from F and W;
$X^4, X^7, X^{11}, X^{12}$ and $X^{13}$ are each independently selected from O and K; and
$J^{10}$ is selected from Y and F.

Clause 6. The antimicrobial peptide of clause 5, wherein the peptide sequence of formula $7A^1$ is selected from the group consisting of: RFCWKVCYKGICFKKCK (RP557) (SEQ ID NO: 8), RWCFKVCYKGICYKKCK (RP560) (SEQ ID NO: 11), OWCFOVCYOGICYOOCO (RP559) (SEQ ID NO: 10), OFCWOVCYOGICFOOCO (RP561) (SEQ ID NO: 12).

Clause 7. The antimicrobial peptide of clause 1, comprising the peptide sequence of formula $7B^1$:

$$X^1\text{-}C^1\text{-}X^2X^3J^4\text{-}C^2\text{-}IGX^7Y\text{-}C^3\text{-}VX^{10}J^{11}\text{-}C^4\text{-}J^{12}X^{13} \quad (7B^1)$$
(SEQ ID NO: 49)

wherein $X^1, X^2, X^3, X^7$ and $X^{10}$ are each independently selected from O and R;
$J^4$ is selected from Y and F;
$J^{11}$ and $J^{12}$ are each independently selected from F and W; and
$X^{13}$ is selected from K and O.

Clause 8. The antimicrobial peptide of clause 7, wherein the peptide sequence of formula $7B^1$ is selected from the group consisting of: RCRRYCIGRYCVRFCWK (RP558) (SEQ ID NO: 9) and OCOOFCIGOYCVOWCFO (RP562) (SEQ ID NO: 13).

Clause 9. The antimicrobial peptide of clause 1, comprising the peptide sequence of formula 6A:

$$FX^2IX^4AX^6L(X^8)_m\text{-}B\text{-}(X^{13})_mIX^{15}AX^{17}LX^{19}F \quad (6A)$$
(SEQ ID NO: 27)

wherein:
B is a sequence selected from $CLGX^{11}FC$ (SEQ ID NO: 28), $GCLGX^{11}FCG$ (SEQ ID NO: 29) and $GGCLGX^{11}FCGG$ (SEQ ID NO: 30), wherein each C is a cysteine residue, each G is a glycine residue and $X^{11}$ is selected from O and K;
$X^2, X^4, X^8, X^{13}, X^{15}$ and $X^{19}$ are each independently selected from O and K;
$X^6$ and $X^{17}$ are each independently selected from R and O; and
m is an integer selected from 0 or 1.

Clause 10. The antimicrobial peptide of clause 9, wherein the peptide sequence of formula 6A is selected from the group consisting of: FKIOARLCLGOFCIOARLK (RP550) (SEQ ID NO: 1), FOIOAOLGGCLGOFCGGIOAOLOF (RP564) (SEQ ID NO: 15), FOIOAOLOGGCLGOFCG-GOIOAOLOF (RP565) (SEQ ID NO: 16), FOIKAOLG-GCLGKFCGGIKAOLKF (RP566) (SEQ ID NO: 17) and FOIKAOLKGGCLGKFCGGKIKAOLKF (RP 567) (SEQ ID NO: 18).

Clause 11. The antimicrobial peptide of clause 1, comprising the peptide sequence of formula 3A:

$$FX^2J^3X^4J^5X^6J^7X^8J^9XJ^{11}X^{12}J^{13}X^{14}J^{15}X^{16}J^{17} \quad (3A)$$

wherein:
$X^2$ and $X^{14}$ are each independently selected from O and R;
$J^3$ and $J^{17}$ are each independently selected from L and I;
$X^4$ and $X^{16}$ are each independently selected from K and O;
$J^5$ is selected from A and I;
$X^6, X^8, X^{10}$ and $X^2$ are each independently selected from R, K and O;
$J^7$ is selected from F, A and I;
$J^9$ is selected from V and L;
$J^{11}$ is selected from A, V and L;
$J^{13}$ is selected from A, I and L; and
$J^{15}$ is selected from I, F and L.

Clause 12. The antimicrobial peptide of clause 11, wherein the peptide sequence of formula 3A is selected from the group consisting of: FOIKARFOVRARLOLKI (RP553) (SEQ ID NO: 4), FOLOAOIOVOLOAOIOL (RP555) (SEQ ID NO: 6), FOLOAOIKVKLOAOIOL (RP556) (SEQ ID NO: 7) and FRLKIKARLKVKIRFKL (RP554) (SEQ ID NO: 5).

Clause 13. The antimicrobial peptide of any one of clauses 1-4, wherein the peptide sequence selected from RP550-567 is RFCWKVCYKGICFKKCK (RP557) (SEQ ID NO: 8).

Clause 14. The antimicrobial peptide any one of clauses 1-4, wherein the peptide sequence selected from RP550-567 is FKIOARLCLGOFCIOARLK (RP550) (SEQ ID NO: 1).

Clause 15. The antimicrobial peptide of any one of claims 1-4, wherein the peptide sequence selected from RP550-567 is FIOKFAKOFKOFIOKFAKFAFAF (RP551) (SEQ ID NO: 2).

Clause 16. The antimicrobial peptide of any one of claims 1-4, wherein the peptide sequence selected from RP550-567 is FAFAFKAFKKAFKOFOOAFOOAF (RP552) (SEQ ID NO: 3).

Clause 17. The antimicrobial peptide of any one of claims 1-4, wherein the peptide sequence selected from RP550-567 is FOIKARFOVRARLOLKI (RP553) (SEQ ID NO: 4).

Clause 18. The antimicrobial peptide of any one of claims 1-4, wherein the peptide sequence selected from RP550-567 is FRLKIKARLKVKIRFKL (RP554) (SEQ ID NO: 5).

Clause 19. The antimicrobial peptide of any one of claims 1-4, wherein the peptide sequence selected from RP550-567 is FOLOAOIOVOLOAOIOL (RP555) (SEQ ID NO: 6).

Clause 20. The antimicrobial peptide of any one of claims 1-4, wherein the peptide sequence selected from RP550-557 is FOLOAOIKVKLOAOIOL (RP556) (SEQ ID NO: 7).

Clause 21. The antimicrobial peptide any one of clauses 1-4, wherein the peptide sequence selected from RP550-567 is RCRRYCIGRYCVRFCWK (RP558) (SEQ ID NO: 9).

Clause 22. The antimicrobial peptide of any one of claims 1-4, wherein the peptide sequence selected from RP550-567 is OWCFOVCYOGICYOOCO (RP559) (SEQ ID NO: 10).

Clause 23. The antimicrobial peptide of any one of claims 1-4, wherein the peptide sequence selected from RP550-567 is RWCFKVCYKGICYKKCK (RP560) (SEQ ID NO: 11).

Clause 24. The antimicrobial peptide of any one of claims 1-4, wherein the peptide sequence selected from RP550-567 is OFCWOVCYOGICFOOCO (RP561) (SEQ ID NO: 12).

Clause 25. The antimicrobial peptide of any one of claims 1-4, wherein the peptide sequence selected from RP550-567 is OCOOFCIGOYCVOWCFO (RP562) (SEQ ID NO: 13).

Clause 26. The antimicrobial peptide of any one of claims 1-4, wherein the peptide sequence selected from RP550-567 is RGVCVCFRRRCYCLRGGR (RP563) (SEQ ID NO: 14).

Clause 27. The antimicrobial peptide of any one of claims 1-4, wherein the peptide sequence selected from RP550-557 is FOIOAOLGGCLGOFCGGIOAOLOF (RP564) (SEQ ID NO: 15).

Clause 28. The antimicrobial peptide of any one of claims 1-4, wherein the peptide sequence selected from RP550-557 is FOIOAOLOGGCLGOFCGGOIOAOLOF (RP565) (SEQ ID NO: 16).

Clause 29. The antimicrobial peptide of any one of claims 1-4, wherein the peptide sequence selected from RP550-557 is FOIKAOLGGCLGKFCGGIKAOLKF (RP566) (SEQ ID NO: 17).

Clause 30. The antimicrobial peptide of any one of claims 1-4, wherein the peptide sequence selected from RP550-557 is FOIKAOLKGGCLGKFCGGKIKAOLKF (RP567) (SEQ ID NO: 18).

Clause 31. An antimicrobial peptide, comprising the peptide sequence of formula (7A$^1$):

$$X^1-J^2-C^1-J^3X^4V-C^2-YX^7GI-C^3-J^{10}X^{11}X^{12}-C^4-X^{13} \quad (7A^1)$$
(SEQ ID NO: 47)

Wherein:
$X^1$ is selected from O and R;
$J^2$ and $J^3$ are each independently selected from F and W;
$X^4$, $X^7$, $X^{11}$, $X^{12}$ and $X^{13}$ are each independently selected from O and K; and
$J^{10}$ is selected from Y and F.

Clause 32. The antimicrobial peptide of clause 31, wherein the peptide sequence of formula 7A$^1$ is selected from the group consisting of: RFCWKVCYKGICFKKCK (RP557) (SEQ ID NO: 8), RWCFKVCYKGICYKKCK (RP560) (SEQ ID NO: 11), OWCFOVCYOGICYOOCO (RP559) (SEQ ID NO: 10), OFCWOVCYOGICFOOCO (RP661) (SEQ ID NO: 12).

Clause 33. An antimicrobial peptide, comprising the peptide sequence of formula (7B$^1$)

$$X^1-C^1-X^2X^3J^4-C^2-IGX^7Y-C^3-VX^{10}J^{11}-C^4-J^{12}X^{13} \quad (7B^1)$$
(SEQ ID NO: 49)

wherein $X^1$, $X^2$, $X^3$, $X^7$ and $X^{10}$ are each independently selected from O and R;
$J^4$ is selected from Y and F;
$J^{11}$ and $J^{12}$ are each independently selected from F and W; and
$X^{13}$ is selected from K and O.

Clause 34. The antimicrobial peptide of clause 33, wherein the peptide sequence of formula 7B$^1$ is selected from the group consisting of: RCRRYCIGRYCVRFCWK (RP558) (SEQ ID NO: 9), OCOOFCIGOYCVOWCFO (RP562) (SEQ ID NO: 13).

Clause 35. An antimicrobial peptide, comprising the peptide sequence of formula (6A)

$$FX^2IX^4AX^6L(X^8)_m-B-(X^{13})_mIX^{15}AX^{17}LX^{19}F \quad (6A)$$
(SEQ ID NO: 27)

wherein:
B is a sequence selected from CLGX$^{11}$FC (SEQ ID NO: 28), GCLGX$^{11}$FCG (SEQ ID NO: 29) and GGCLGX$^{11}$FCGG (SEQ ID NO: 30), wherein each C is a cysteine residue, each G is a glycine residue and $X^{11}$ is selected from O and K; $X^2$, $X^4$, $X^8$, $X^{13}$, $X^{15}$ and $X^{19}$ are each independently selected from O and K;
$X^6$ and $X^{17}$ are each independently selected from R and O; and
m is an integer selected from 0 or 1.

Clause 36. The antimicrobial peptide of clause 35, wherein the peptide sequence of formula 6A is selected from the group consisting of: FKIOARLCLGOFCIOARLK (RP550) (SEQ ID NO: 1), FOIOAOLGGCLGOFCGGIOAOLOF (RP564) (SEQ ID NO: 15), FOIOAOLOGGCLGOFCGGOIOAOLOF (RP565) (SEQ ID NO: 16), FOIKAOLGGCLGKFCGGIKAOLKF (RP566) (SEQ ID NO: 17), FOIKAOLKGGCLGKFCGGKIKAOLKF (RP 567) (SEQ ID NO: 18).

Clause 37. An antimicrobial peptide, comprising the peptide sequence of formula (3A)

$$FX^2J^3X^4J^5X^6J^7X^8J^9X^{10}J^{11}X^{12}J^{13}X^{14}J^{15}X^{16}J^{17} \quad (3A)$$

wherein:
$X^2$ and $X^{14}$ are each independently selected from O and R;
$J^3$ and $J^{17}$ are each independently selected from L and I;
$X^4$ and $X^{16}$ are each independently selected from K and O;
$J^5$ is selected from A and I;
$X^6$, $X^8$, $X^{10}$ and $X^{12}$ are each independently selected from R, K and O;
$J^7$ is selected from F, A and I;
$J^9$ is selected from V and L;
$J^{11}$ is selected from A, V and L;
$J^{13}$ is selected from A, I and L; and
$J^{15}$ is selected from I, F and L.

Clause 38. The antimicrobial peptide of clause 37, wherein the peptide sequence of formula 3A is selected from the group consisting of: FOIKARFOVRARLOLKI (RP553) (SEQ ID NO: 4), FOLOAOIOVOLOAOIOL (RP555) (SEQ ID NO: 6), FOLOAOIKVKLOAOIOL (RP556) (SEQ ID NO: 7), FRLKIKARLKVKIRFKL (RP554) (SEQ ID NO: 5).

Clause 39. A pharmaceutical composition, comprising the antimicrobial peptide of any one of clauses 1-38 and a pharmaceutically acceptable carrier.

Clause 40. The pharmaceutical composition of clause 39, wherein the composition is formulated for oral administration, parenteral administration, or topical administration.

Clause 41. The pharmaceutical composition of clause 39, wherein the composition is formulated for oral administration and further comprises an enteric coating.

Clause 42. The pharmaceutical composition of clause 39, wherein the composition is formulated for topical delivery in a form selected from the group consisting of: a gel suspension, a cream, microneedle, and infused into a bandage or topical patch.

Clause 43. The pharmaceutical composition of clause 39, wherein the composition is formulated for inhalation.

Clause 44. The pharmaceutical composition of clause 39, wherein the composition is an ophthalmic composition formulated for delivery to the eye of a subject, e.g., via topical instillation, subconjunctival, subtenon, intravitreal, retrobulbar, or intracameral administration.

Clause 45. The pharmaceutical composition of clause 43, wherein the composition further comprises liposomes comprising free and/or encapsulated antimicrobial peptide.

Clause 46. The pharmaceutical composition of any one of clauses 39-45, further comprising an additional bioactive agent.

Clause 47. The pharmaceutical composition of clause 46, wherein the additional bioactive agent is selected from an antimicrobial agent, an anti-inflammatory drug, an anti-nausea drug, an anti-pain medication, and combinations thereof.

Clause 48. The pharmaceutical composition of clause 39, wherein the composition is formulated to be coated on the surface of an implantable medical device.

Clause 49. The pharmaceutical composition of clause 48, wherein the medical device is selected from surgical instruments and indwelling medical devices.

Clause 50. A method of treating or preventing a microbial infection (e.g., as described herein) in a subject in need thereof, the method comprising administering a pharmaceutical composition according to any one of clauses 39-49 to the subject.

Clause 51. The method of clause 50, wherein the pharmaceutical composition is administered to the subject orally, parenterally, via inhalation or topically.

Clause 52. The method of clause 50, wherein the pharmaceutical composition is an ophthalmic composition administered to the eye of a subject (e.g., as described herein via topical instillation, subconjunctival, subtenon, intravitreal, retrobulbar, or intracameral route of administration).

Clause 53. The method of clause 50, wherein the pharmaceutical composition is administered to the subject by applying the composition to a surface of a medical device prior to inserting the medical device into the subject.

Clause 54. The method of any one of clauses 50-53, wherein the subject is selected from the group consisting of: a human, a domesticated animal, a farm animal, and a zoo animal.

Clause 55. The method of any one of clauses 50-54, wherein the pharmaceutical composition is administered in combination with an antimicrobial agent and/or antibiotic.

Clause 56 A method of treating microbial infection in an animal, comprising administering to an infected or at-risk animal a pharmaceutical or veterinary product, a medical device or a dietary product comprising a peptide (e.g., as described herein) in an amount effective to enhance growth and weight gain of the animal.

Clause 57. A method of inhibiting a microbial growth, colony or infection (e.g., as described herein) in a sample comprising microbes, the method comprising contacting the sample with an antimicrobial peptide according to any one of clauses 1-38 to inhibit the microbial growth, colony or infection.

Clause 58. The method of clause 57, wherein the sample is a cell sample.

It will also be recognized by those skilled in the art that, while the invention has been described above in terms of preferred embodiments, it is not limited thereto. Various features and aspects of the above described invention may be used individually or jointly. Further, although the invention has been described in the context of its implementation in a particular environment, and for particular applications those skilled in the art will recognize that its usefulness is not limited thereto and that the present invention can be beneficially utilized in any number of environments and implementations. Accordingly, the claims set forth below should be construed in view of the full breadth and spirit of the invention as disclosed herein.

What is claimed:

1. An antimicrobial peptide, comprising:
   a) a peptide sequence selected from:

| | |
   |---|---|
   | FIOKFAKOFKOFIOKFAKFAFAF(RP551) | (SEQ ID NO: 2); |
   | FAFAFKAFKKAFKOFOOAFOOAF(RP552) | (SEQ ID NO: 3); |
   | FOIKARFOVRARLOLKI(RP553) | (SEQ ID NO: 4); |
   | FRLKIKARLKVKIRFKL(RP554) | (SEQ ID NO: 5); |
   | FOLOAOIOVOLOAOIOL(RP555) | (SEQ ID NO: 6); |
   | FOLOAOIKVKLOAOIOL(RP556) | (SEQ ID NO: 7); |
   | RFCWKVCYKGICFKKCK(RP557) | (SEQ ID NO: 8); |
   | OWCFOVCYOGICYOOCO(RP559) | (SEQ ID NO: 10); |
   | OFCWOVCYOGICFOOCO(RP561) | (SEQ ID NO: 12); |
   | OCOOFCIGOYCVOWCFO(RP562) | (SEQ ID NO: 13); |
   | FOIOAOLOGGCLGOFCGGOIOAOLOF (RP565) | (SEQ ID NO: 16); |
   | FOIKAOLGGCLGKFCGGIKAOLKF (RP566) | (SEQ ID NO: 17); and |
   | FOIKAOLKGGCLGKFCGGKIKAOLKF (RP567) | (SEQ ID NO: 18). |

2. The antimicrobial peptide of claim 1, wherein the peptide comprises the sequence RFCWKVCYKGICFKKCK (RP557) (SEQ ID NO: 8).

3. The antimicrobial peptide of claim 1, wherein the peptide comprises the sequence FOLOAOIOVOLOAOIOL (RP555) (SEQ ID NO: 6).

4. The antimicrobial peptide of claim 1, wherein the peptide comprises the sequence FIOKFAKOFKOFIOK-FAKFAFAF (RP551) (SEQ ID NO: 2).

5. The antimicrobial peptide of claim 1, wherein the peptide comprises the sequence FAFAFKAFKKAFKO-FOOAFOOAF (RP552) (SEQ ID NO: 3).

6. The antimicrobial peptide of claim 1, wherein the peptide comprises the sequence FOIKARFOVRARLOLKI (RP553) (SEQ ID NO: 4).

7. The antimicrobial peptide of claim 1, wherein the peptide comprises the sequence FOLOAOIKVKLOAOIOL (RP556) (SEQ ID NO: 7).

8. The antimicrobial peptide of claim 1, wherein the peptide comprises the sequence FRLKIKARLKVKIRFKL (RP554) (SEQ ID NO: 5).

9. The antimicrobial peptide of claim 1, wherein the peptide comprises the sequence OCOOFCIGOYCVOW-CFO (RP562) (SEQ ID NO: 13).

10. The antimicrobial peptide of claim 1, wherein the peptide comprises the sequence FOIOAOLOGGCLG-OFCGGOIOAOLOF (RP565) (SEQ ID NO: 16).

11. The antimicrobial peptide of claim 1, wherein the peptide comprises the sequence FOIKAOLGGCLGKFCG-GIKAOLKF (RP566) (SEQ ID NO: 17).

12. The antimicrobial peptide of claim 1, wherein the peptide comprises the sequence FOIKAOLKGGCLGK-FCGGKIKAOLKF (RP567) (SEQ ID NO: 18).

13. An antimicrobial peptide comprising:
   a) a peptide sequence selected from SEQ ID NO: 2,4-8, 10, 12, 13 and 18; or
   b) a sequence having five or less amino acid substitutions relative to the sequence defined in a), wherein the five or less amino acid substitutions consist of substitution of a cationic amino acid of the sequence with an alternative cationic amino acid residue; or
   c) a peptide sequence having at least 90% sequence identity with a sequence selected from SEQ ID NO: 2, 4-8, 10, 12, 13 and 18.

14. The antimicrobial peptide of claim 13, comprising a peptide sequence selected from:

| | |
   |---|---|
   | RFCWKVCYKGICFKKCK(RP557) | (SEQ ID NO: 8); |
   | OFCWOVCYOGICFOOCO(RP561) | (SEQ ID NO: 12); and |
   | OWCFOVCYOGICYOOCO(RP559) | (SEQ ID NO: 10). |

15. An antimicrobial peptide, comprising the sequence RWCFKVCYKGICYKKCK (RP560) (SEQ ID NO: 11).

16. A pharmaceutical composition, comprising the antimicrobial peptide of claim 1 and a pharmaceutically acceptable carrier.

17. The pharmaceutical composition of claim 16, wherein the composition is formulated for oral administration, parenteral administration, inhalation administration, intra-tumoral administration, subcutaneous administration, intraperitoneal administration, systemic or topical administration.

18. The pharmaceutical composition of claim 16, wherein the composition is formulated for oral administration and further comprises an enteric coating.

19. The pharmaceutical composition of claim 16, wherein the composition is formulated for topical delivery in a form selected from a gel suspension, a cream, microneedle, and infused into a bandage or topical patch.

20. The pharmaceutical composition of claim 16, wherein the composition is formulated for inhalation.

21. The pharmaceutical composition of claim 16, further comprising an additional bioactive agent.

22. The pharmaceutical composition of claim 21, wherein the additional bioactive agent is selected from an antimicrobial agent, an anti-inflammatory drug, an anti-nausea drug, an anti-pain medication, and combinations thereof.

23. The pharmaceutical composition of claim 16, wherein the composition is formulated to be coated on the surface of an implantable medical device.

\* \* \* \* \*

SEQUENCE LISTING

```
<160> NUMBER OF SEQ ID NOS: 81

<210> SEQ ID NO 1
<211> LENGTH: 19
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (4)..(4)
<223> OTHER INFORMATION: Xaa is ornithine
<220> FEATURE:
<221> NAME/KEY: misc_feature
<222> LOCATION: (11)..(11)
<223> OTHER INFORMATION: Xaa is ornithine
<220> FEATURE:
<221> NAME/KEY: misc_feature
<222> LOCATION: (15)..(15)
<223> OTHER INFORMATION: Xaa is ornithine
```

-continued

```
<400> SEQUENCE: 1

Phe Lys Ile Xaa Ala Arg Leu Cys Leu Gly Xaa Phe Cys Ile Xaa Ala
1               5                   10                  15

Arg Leu Lys

<210> SEQ ID NO 2
<211> LENGTH: 23
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (3)..(3)
<223> OTHER INFORMATION: Xaa is ornithine
<220> FEATURE:
<221> NAME/KEY: misc_feature
<222> LOCATION: (8)..(8)
<223> OTHER INFORMATION: Xaa is ornithine
<220> FEATURE:
<221> NAME/KEY: misc_feature
<222> LOCATION: (11)..(11)
<223> OTHER INFORMATION: Xaa is ornithine
<220> FEATURE:
<221> NAME/KEY: misc_feature
<222> LOCATION: (14)..(14)
<223> OTHER INFORMATION: Xaa is ornithine

<400> SEQUENCE: 2

Phe Ile Xaa Lys Phe Ala Lys Xaa Phe Lys Xaa Phe Ile Xaa Lys Phe
1               5                   10                  15

Ala Lys Phe Ala Phe Ala Phe
            20

<210> SEQ ID NO 3
<211> LENGTH: 23
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (14)..(14)
<223> OTHER INFORMATION: Xaa is ornithine
<220> FEATURE:
<221> NAME/KEY: misc_feature
<222> LOCATION: (16)..(17)
<223> OTHER INFORMATION: Xaa is ornithine
<220> FEATURE:
<221> NAME/KEY: misc_feature
<222> LOCATION: (20)..(21)
<223> OTHER INFORMATION: Xaa is ornithine

<400> SEQUENCE: 3

Phe Ala Phe Ala Phe Lys Ala Phe Lys Lys Ala Phe Lys Xaa Phe Xaa
1               5                   10                  15

Xaa Ala Phe Xaa Xaa Ala Phe
            20

<210> SEQ ID NO 4
<211> LENGTH: 17
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (2)..(2)
<223> OTHER INFORMATION: Xaa is ornithine
<220> FEATURE:
```

```
<221> NAME/KEY: misc_feature
<222> LOCATION: (8)..(8)
<223> OTHER INFORMATION: Xaa is ornithine
<220> FEATURE:
<221> NAME/KEY: misc_feature
<222> LOCATION: (14)..(14)
<223> OTHER INFORMATION: Xaa is ornithine

<400> SEQUENCE: 4

Phe Xaa Ile Lys Ala Arg Phe Xaa Val Arg Ala Arg Leu Xaa Leu Lys
1               5                   10                  15

Ile

<210> SEQ ID NO 5
<211> LENGTH: 17
<212> TYPE: PRT
<213> ORGANISM: Artificial Sequence
<220> FEATURE:
<223> OTHER INFORMATION: Synthetic sequence

<400> SEQUENCE: 5

Phe Arg Leu Lys Ile Lys Ala Arg Leu Lys Val Lys Ile Arg Phe Lys
1               5                   10                  15

Leu

<210> SEQ ID NO 6
<211> LENGTH: 17
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (2)..(2)
<223> OTHER INFORMATION: Xaa is ornithine
<220> FEATURE:
<221> NAME/KEY: misc_feature
<222> LOCATION: (4)..(4)
<223> OTHER INFORMATION: Xaa is ornithine
<220> FEATURE:
<221> NAME/KEY: misc_feature
<222> LOCATION: (6)..(6)
<223> OTHER INFORMATION: Xaa is ornithine
<220> FEATURE:
<221> NAME/KEY: misc_feature
<222> LOCATION: (8)..(8)
<223> OTHER INFORMATION: Xaa is ornithine
<220> FEATURE:
<221> NAME/KEY: misc_feature
<222> LOCATION: (10)..(10)
<223> OTHER INFORMATION: Xaa is ornithine
<220> FEATURE:
<221> NAME/KEY: misc_feature
<222> LOCATION: (12)..(12)
<223> OTHER INFORMATION: Xaa is ornithine
<220> FEATURE:
<221> NAME/KEY: misc_feature
<222> LOCATION: (14)..(14)
<223> OTHER INFORMATION: Xaa is ornithine
<220> FEATURE:
<221> NAME/KEY: misc_feature
<222> LOCATION: (16)..(16)
<223> OTHER INFORMATION: Xaa is ornithine

<400> SEQUENCE: 6

Phe Xaa Leu Xaa Ala Xaa Ile Xaa Val Xaa Leu Xaa Ala Xaa Ile Xaa
1               5                   10                  15

Leu

<210> SEQ ID NO 7
```

```
<211> LENGTH: 17
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (2)..(2)
<223> OTHER INFORMATION: Xaa is ornithine
<220> FEATURE:
<221> NAME/KEY: misc_feature
<222> LOCATION: (4)..(4)
<223> OTHER INFORMATION: Xaa is ornithine
<220> FEATURE:
<221> NAME/KEY: misc_feature
<222> LOCATION: (6)..(6)
<223> OTHER INFORMATION: Xaa is ornithine
<220> FEATURE:
<221> NAME/KEY: misc_feature
<222> LOCATION: (12)..(12)
<223> OTHER INFORMATION: Xaa is ornithine
<220> FEATURE:
<221> NAME/KEY: misc_feature
<222> LOCATION: (14)..(14)
<223> OTHER INFORMATION: Xaa is ornithine
<220> FEATURE:
<221> NAME/KEY: misc_feature
<222> LOCATION: (16)..(16)
<223> OTHER INFORMATION: Xaa is ornithine

<400> SEQUENCE: 7

Phe Xaa Leu Xaa Ala Xaa Ile Lys Val Lys Leu Xaa Ala Xaa Ile Xaa
1               5                   10                  15

Leu

<210> SEQ ID NO 8
<211> LENGTH: 17
<212> TYPE: PRT
<213> ORGANISM: Artificial Sequence
<220> FEATURE:
<223> OTHER INFORMATION: Synthetic sequence

<400> SEQUENCE: 8

Arg Phe Cys Trp Lys Val Cys Tyr Lys Gly Ile Cys Phe Lys Lys Cys
1               5                   10                  15

Lys

<210> SEQ ID NO 9
<211> LENGTH: 17
<212> TYPE: PRT
<213> ORGANISM: Artificial Sequence
<220> FEATURE:
<223> OTHER INFORMATION: Synthetic sequence

<400> SEQUENCE: 9

Arg Cys Arg Arg Tyr Cys Ile Gly Arg Tyr Cys Val Arg Phe Cys Trp
1               5                   10                  15

Lys

<210> SEQ ID NO 10
<211> LENGTH: 17
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: Xaa is ornithine
<220> FEATURE:
```

```
<221> NAME/KEY: misc_feature
<222> LOCATION: (5)..(5)
<223> OTHER INFORMATION: Xaa is ornithine
<220> FEATURE:
<221> NAME/KEY: misc_feature
<222> LOCATION: (9)..(9)
<223> OTHER INFORMATION: Xaa is ornithine
<220> FEATURE:
<221> NAME/KEY: misc_feature
<222> LOCATION: (14)..(15)
<223> OTHER INFORMATION: Xaa is ornithine
<220> FEATURE:
<221> NAME/KEY: misc_feature
<222> LOCATION: (17)..(17)
<223> OTHER INFORMATION: Xaa is ornithine

<400> SEQUENCE: 10

Xaa Trp Cys Phe Xaa Val Cys Tyr Xaa Gly Ile Cys Tyr Xaa Xaa Cys
1               5                   10                  15

Xaa

<210> SEQ ID NO 11
<211> LENGTH: 17
<212> TYPE: PRT
<213> ORGANISM: Artificial Sequence
<220> FEATURE:
<223> OTHER INFORMATION: Synthetic sequence

<400> SEQUENCE: 11

Arg Trp Cys Phe Lys Val Cys Tyr Lys Gly Ile Cys Tyr Lys Lys Cys
1               5                   10                  15

Lys

<210> SEQ ID NO 12
<211> LENGTH: 17
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: Xaa is ornithine
<220> FEATURE:
<221> NAME/KEY: misc_feature
<222> LOCATION: (5)..(5)
<223> OTHER INFORMATION: Xaa is ornithine
<220> FEATURE:
<221> NAME/KEY: misc_feature
<222> LOCATION: (9)..(9)
<223> OTHER INFORMATION: Xaa is ornithine
<220> FEATURE:
<221> NAME/KEY: misc_feature
<222> LOCATION: (14)..(15)
<223> OTHER INFORMATION: Xaa is ornithine
<220> FEATURE:
<221> NAME/KEY: misc_feature
<222> LOCATION: (17)..(17)
<223> OTHER INFORMATION: Xaa is ornithine

<400> SEQUENCE: 12

Xaa Phe Cys Trp Xaa Val Cys Tyr Xaa Gly Ile Cys Phe Xaa Xaa Cys
1               5                   10                  15

Xaa

<210> SEQ ID NO 13
<211> LENGTH: 17
<212> TYPE: PRT
<213> ORGANISM: Artificial Sequence
<220> FEATURE:
```

```
<223> OTHER INFORMATION: Synthetic sequence
<220> FEATURE:
<221> NAME/KEY: misc_feature
<222> LOCATION: (1)..(1)
<223> OTHER INFORMATION: Xaa is ornithine
<220> FEATURE:
<221> NAME/KEY: misc_feature
<222> LOCATION: (3)..(4)
<223> OTHER INFORMATION: Xaa is ornithine
<220> FEATURE:
<221> NAME/KEY: misc_feature
<222> LOCATION: (9)..(9)
<223> OTHER INFORMATION: Xaa is ornithine
<220> FEATURE:
<221> NAME/KEY: misc_feature
<222> LOCATION: (13)..(13)
<223> OTHER INFORMATION: Xaa is ornithine
<220> FEATURE:
<221> NAME/KEY: misc_feature
<222> LOCATION: (17)..(17)
<223> OTHER INFORMATION: Xaa is ornithine

<400> SEQUENCE: 13

Xaa Cys Xaa Xaa Phe Cys Ile Gly Xaa Tyr Cys Val Xaa Trp Cys Phe
1               5                   10                  15

Xaa

<210> SEQ ID NO 14
<211> LENGTH: 18
<212> TYPE: PRT
<213> ORGANISM: Artificial Sequence
<220> FEATURE:
<223> OTHER INFORMATION: Synthetic sequence

<400> SEQUENCE: 14

Arg Gly Val Cys Val Cys Phe Arg Arg Cys Tyr Cys Leu Arg Gly
1               5                   10                  15

Gly Arg

<210> SEQ ID NO 15
<211> LENGTH: 24
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (2)..(2)
<223> OTHER INFORMATION: Xaa is ornithine
<220> FEATURE:
<221> NAME/KEY: misc_feature
<222> LOCATION: (4)..(4)
<223> OTHER INFORMATION: Xaa is ornithine
<220> FEATURE:
<221> NAME/KEY: misc_feature
<222> LOCATION: (6)..(6)
<223> OTHER INFORMATION: Xaa is ornithine
<220> FEATURE:
<221> NAME/KEY: misc_feature
<222> LOCATION: (13)..(13)
<223> OTHER INFORMATION: Xaa is ornithine
<220> FEATURE:
<221> NAME/KEY: misc_feature
<222> LOCATION: (19)..(19)
<223> OTHER INFORMATION: Xaa is ornithine
<220> FEATURE:
<221> NAME/KEY: misc_feature
<222> LOCATION: (21)..(21)
<223> OTHER INFORMATION: Xaa is ornithine
<220> FEATURE:
<221> NAME/KEY: misc_feature
<222> LOCATION: (23)..(23)
<223> OTHER INFORMATION: Xaa is ornithine
```

<400> SEQUENCE: 15

Phe Xaa Ile Xaa Ala Xaa Leu Gly Gly Cys Leu Gly Xaa Phe Cys Gly
1               5                   10                  15

Gly Ile Xaa Ala Xaa Leu Xaa Phe
            20

<210> SEQ ID NO 16
<211> LENGTH: 26
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (2)..(2)
<223> OTHER INFORMATION: Xaa is ornithine
<220> FEATURE:
<221> NAME/KEY: misc_feature
<222> LOCATION: (4)..(4)
<223> OTHER INFORMATION: Xaa is ornithine
<220> FEATURE:
<221> NAME/KEY: misc_feature
<222> LOCATION: (6)..(6)
<223> OTHER INFORMATION: Xaa is ornithine
<220> FEATURE:
<221> NAME/KEY: misc_feature
<222> LOCATION: (8)..(8)
<223> OTHER INFORMATION: Xaa is ornithine
<220> FEATURE:
<221> NAME/KEY: misc_feature
<222> LOCATION: (14)..(14)
<223> OTHER INFORMATION: Xaa is ornithine
<220> FEATURE:
<221> NAME/KEY: misc_feature
<222> LOCATION: (19)..(19)
<223> OTHER INFORMATION: Xaa is ornithine
<220> FEATURE:
<221> NAME/KEY: misc_feature
<222> LOCATION: (21)..(21)
<223> OTHER INFORMATION: Xaa is ornithine
<220> FEATURE:
<221> NAME/KEY: misc_feature
<222> LOCATION: (23)..(23)
<223> OTHER INFORMATION: Xaa is ornithine
<220> FEATURE:
<221> NAME/KEY: misc_feature
<222> LOCATION: (25)..(25)
<223> OTHER INFORMATION: Xaa is ornithine

<400> SEQUENCE: 16

Phe Xaa Ile Xaa Ala Xaa Leu Xaa Gly Gly Cys Leu Gly Xaa Phe Cys
1               5                   10                  15

Gly Gly Xaa Ile Xaa Ala Xaa Leu Xaa Phe
            20                  25

<210> SEQ ID NO 17
<211> LENGTH: 24
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (2)..(2)
<223> OTHER INFORMATION: Xaa is ornithine
<220> FEATURE:
<221> NAME/KEY: misc_feature
<222> LOCATION: (6)..(6)
<223> OTHER INFORMATION: Xaa is ornithine
<220> FEATURE:
<221> NAME/KEY: misc_feature
<222> LOCATION: (21)..(21)

<223> OTHER INFORMATION: Xaa is ornithine

<400> SEQUENCE: 17

Phe Xaa Ile Lys Ala Xaa Leu Gly Gly Cys Leu Gly Lys Phe Cys Gly
1               5                   10                  15

Gly Ile Lys Ala Xaa Leu Lys Phe
            20

<210> SEQ ID NO 18
<211> LENGTH: 26
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (2)..(2)
<223> OTHER INFORMATION: Xaa is ornithine
<220> FEATURE:
<221> NAME/KEY: misc_feature
<222> LOCATION: (6)..(6)
<223> OTHER INFORMATION: Xaa is ornithine
<220> FEATURE:
<221> NAME/KEY: misc_feature
<222> LOCATION: (23)..(23)
<223> OTHER INFORMATION: Xaa is ornithine

<400> SEQUENCE: 18

Phe Xaa Ile Lys Ala Xaa Leu Lys Gly Gly Cys Leu Gly Lys Phe Cys
1               5                   10                  15

Gly Gly Lys Ile Lys Ala Xaa Leu Lys Phe
            20                  25

<210> SEQ ID NO 19
<211> LENGTH: 5
<212> TYPE: PRT
<213> ORGANISM: Artificial Sequence
<220> FEATURE:
<223> OTHER INFORMATION: Synthetic sequence

<400> SEQUENCE: 19

Phe Ala Phe Ala Phe
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic sequence

<400> SEQUENCE: 20

Ala Phe Ala Phe Ala
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic sequence

<400> SEQUENCE: 21

Cys Leu Gly Arg Phe Cys
1               5

<210> SEQ ID NO 22

```
<211> LENGTH: 6
<212> TYPE: PRT
<213> ORGANISM: Artificial Sequence
<220> FEATURE:
<223> OTHER INFORMATION: Synthetic sequence

<400> SEQUENCE: 22

Cys Tyr Lys Gly Ile Cys
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: Xaa is a hydrophobic amino acid residue or a
      hydrophilic amino acid residue
<220> FEATURE:
<221> NAME/KEY: misc_feature
<222> LOCATION: (6)..(6)
<223> OTHER INFORMATION: Xaa is a hydrophobic amino acid residue or a
      hydrophilic amino acid residue

<400> SEQUENCE: 23

Xaa Gly Pro Gly Arg Xaa
1               5

<210> SEQ ID NO 24
<211> LENGTH: 17
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (2)..(2)
<223> OTHER INFORMATION: Xaa is Ornithine
<220> FEATURE:
<221> NAME/KEY: misc_feature
<222> LOCATION: (3)..(3)
<223> OTHER INFORMATION: Xaa is I or L
<220> FEATURE:
<221> NAME/KEY: misc_feature
<222> LOCATION: (4)..(4)
<223> OTHER INFORMATION: Xaa is ornithine or K
<220> FEATURE:
<221> NAME/KEY: misc_feature
<222> LOCATION: (6)..(6)
<223> OTHER INFORMATION: Xaa is ornithine or R
<220> FEATURE:
<221> NAME/KEY: misc_feature
<222> LOCATION: (7)..(7)
<223> OTHER INFORMATION: Xaa is I or F
<220> FEATURE:
<221> NAME/KEY: misc_feature
<222> LOCATION: (8)..(8)
<223> OTHER INFORMATION: Xaa is ornithine or K
<220> FEATURE:
<221> NAME/KEY: misc_feature
<222> LOCATION: (10)..(10)
<223> OTHER INFORMATION: Xaa is Ornithine, K, or R
<220> FEATURE:
<221> NAME/KEY: misc_feature
<222> LOCATION: (11)..(11)
<223> OTHER INFORMATION: Xaa is A or L
<220> FEATURE:
<221> NAME/KEY: misc_feature
<222> LOCATION: (12)..(12)
<223> OTHER INFORMATION: Xaa is ornithine or R
<220> FEATURE:
<221> NAME/KEY: misc_feature
```

```
<222> LOCATION: (13)..(13)
<223> OTHER INFORMATION: Xaa is A or L
<220> FEATURE:
<221> NAME/KEY: misc_feature
<222> LOCATION: (14)..(14)
<223> OTHER INFORMATION: Xaa is ornithine
<220> FEATURE:
<221> NAME/KEY: misc_feature
<222> LOCATION: (15)..(15)
<223> OTHER INFORMATION: Xaa is I or L
<220> FEATURE:
<221> NAME/KEY: misc_feature
<222> LOCATION: (16)..(16)
<223> OTHER INFORMATION: Xaa is ornithine or K
<220> FEATURE:
<221> NAME/KEY: misc_feature
<222> LOCATION: (17)..(17)
<223> OTHER INFORMATION: Xaa is I or L

<400> SEQUENCE: 24

Phe Xaa Xaa Xaa Ala Xaa Xaa Xaa Val Xaa Xaa Xaa Xaa Xaa Xaa Xaa
1               5                   10                  15

Xaa

<210> SEQ ID NO 25
<211> LENGTH: 11
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (4)..(4)
<223> OTHER INFORMATION: Xaa is a hydrophobic amino acid residue or a
      hydrophilic amino acid residue
<220> FEATURE:
<221> NAME/KEY: misc_feature
<222> LOCATION: (5)..(5)
<223> OTHER INFORMATION: Xaa is a hydrophobic amino acid residue or a
      hydrophilic amino acid residue
<220> FEATURE:
<221> NAME/KEY: misc_feature
<222> LOCATION: (6)..(6)
<223> OTHER INFORMATION: Xaa is a hydrophobic amino acid residue or a
      hydrophilic amino acid residue
<220> FEATURE:
<221> NAME/KEY: misc_feature
<222> LOCATION: (7)..(7)
<223> OTHER INFORMATION: Xaa is a hydrophobic amino acid residue, a
      hydrophilic amino acid residue, or is not present
<220> FEATURE:
<221> NAME/KEY: misc_feature
<222> LOCATION: (8)..(8)
<223> OTHER INFORMATION: Xaa is a hydrophobic amino acid residue, a
      hydrophilic amino acid residue, or is not present

<400> SEQUENCE: 25

Gly Gly Cys Xaa Xaa Xaa Xaa Xaa Cys Gly Gly
1               5                   10

<210> SEQ ID NO 26
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: This stretch of residues may be repeated
<220> FEATURE:
<221> NAME/KEY: misc_feature
<222> LOCATION: (3)..(3)
<223> OTHER INFORMATION: Xaa is a hydrophobic amino acid residue
```

```
<220> FEATURE:
<221> NAME/KEY: misc_feature
<222> LOCATION: (4)..(4)
<223> OTHER INFORMATION: Xaa is a hydrophobic amino acid residue
<220> FEATURE:
<221> NAME/KEY: misc_feature
<222> LOCATION: (5)..(5)
<223> OTHER INFORMATION: Xaa is a hydrophilic amino acid residue
<220> FEATURE:
<221> NAME/KEY: misc_feature
<222> LOCATION: (6)..(6)
<223> OTHER INFORMATION: Xaa is a hydrophobic amino acid residue
<220> FEATURE:
<221> NAME/KEY: misc_feature
<222> LOCATION: (8)..(8)
<223> OTHER INFORMATION: This stretch of residues may be repeated

<400> SEQUENCE: 26

Gly Cys Xaa Xaa Xaa Xaa Cys Gly
1               5

<210> SEQ ID NO 27
<211> LENGTH: 17
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (2)..(2)
<223> OTHER INFORMATION: Xaa is ornithine or K
<220> FEATURE:
<221> NAME/KEY: misc_feature
<222> LOCATION: (4)..(4)
<223> OTHER INFORMATION: Xaa is ornithine or K
<220> FEATURE:
<221> NAME/KEY: misc_feature
<222> LOCATION: (6)..(6)
<223> OTHER INFORMATION: Xaa is ornithine or R
<220> FEATURE:
<221> NAME/KEY: misc_feature
<222> LOCATION: (8)..(8)
<223> OTHER INFORMATION: Xaa is ornithine or K
<220> FEATURE:
<221> NAME/KEY: misc_feature
<222> LOCATION: (9)..(9)
<223> OTHER INFORMATION: Xaa is a naturally occuring amino acid
<220> FEATURE:
<221> NAME/KEY: misc_feature
<222> LOCATION: (10)..(10)
<223> OTHER INFORMATION: Xaa is ornithine or K
<220> FEATURE:
<221> NAME/KEY: misc_feature
<222> LOCATION: (12)..(12)
<223> OTHER INFORMATION: Xaa is ornithine or K
<220> FEATURE:
<221> NAME/KEY: misc_feature
<222> LOCATION: (14)..(14)
<223> OTHER INFORMATION: Xaa is ornithine or R
<220> FEATURE:
<221> NAME/KEY: misc_feature
<222> LOCATION: (16)..(16)
<223> OTHER INFORMATION: Xaa is ornithine or K

<400> SEQUENCE: 27

Phe Xaa Ile Xaa Ala Xaa Leu Xaa Xaa Xaa Ile Xaa Ala Xaa Leu Xaa
1               5                   10                  15

Phe

<210> SEQ ID NO 28
<211> LENGTH: 6
<212> TYPE: PRT
<213> ORGANISM: Artificial Sequence
<220> FEATURE:
```

```
<223> OTHER INFORMATION: Synthetic sequence
<220> FEATURE:
<221> NAME/KEY: misc_feature
<222> LOCATION: (4)..(4)
<223> OTHER INFORMATION: Xaa is Ornithine or K

<400> SEQUENCE: 28

Cys Leu Gly Xaa Phe Cys
1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (5)..(5)
<223> OTHER INFORMATION: Xaa is Ornithine or K

<400> SEQUENCE: 29

Gly Cys Leu Gly Xaa Phe Cys Gly
1               5

<210> SEQ ID NO 30
<211> LENGTH: 10
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (6)..(6)
<223> OTHER INFORMATION: Xaa is Ornithine or K

<400> SEQUENCE: 30

Gly Gly Cys Leu Gly Xaa Phe Cys Gly Gly
1               5                   10

<210> SEQ ID NO 31
<211> LENGTH: 24
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: Xaa is a hydrophobic amino acid residue
<220> FEATURE:
<221> NAME/KEY: misc_feature
<222> LOCATION: (2)..(2)
<223> OTHER INFORMATION: Xaa is a hydrophilic amino acid residue
<220> FEATURE:
<221> NAME/KEY: misc_feature
<222> LOCATION: (3)..(3)
<223> OTHER INFORMATION: Xaa is a hydrophobic amino acid residue
<220> FEATURE:
<221> NAME/KEY: misc_feature
<222> LOCATION: (4)..(4)
<223> OTHER INFORMATION: Xaa is a hydrophilic amino acid residue
<220> FEATURE:
<221> NAME/KEY: misc_feature
<222> LOCATION: (5)..(5)
<223> OTHER INFORMATION: Xaa is a hydrophobic amino acid residue
<220> FEATURE:
<221> NAME/KEY: misc_feature
<222> LOCATION: (6)..(6)
<223> OTHER INFORMATION: Xaa is a hydrophilic amino acid residue
<220> FEATURE:
<221> NAME/KEY: misc_feature
<222> LOCATION: (7)..(7)
```

```
<223> OTHER INFORMATION: Xaa is a hydrophobic amino acid residue
<220> FEATURE:
<221> NAME/KEY: misc_feature
<222> LOCATION: (11)..(11)
<223> OTHER INFORMATION: Xaa is a hydrophobic amino acid residue
<220> FEATURE:
<221> NAME/KEY: misc_feature
<222> LOCATION: (12)..(12)
<223> OTHER INFORMATION: Xaa is a hydrophobic amino acid residue
<220> FEATURE:
<221> NAME/KEY: misc_feature
<222> LOCATION: (13)..(13)
<223> OTHER INFORMATION: Xaa is a hydrophilic amino acid residue
<220> FEATURE:
<221> NAME/KEY: misc_feature
<222> LOCATION: (14)..(14)
<223> OTHER INFORMATION: Xaa is a hydrophobic amino acid residue
<220> FEATURE:
<221> NAME/KEY: misc_feature
<222> LOCATION: (18)..(18)
<223> OTHER INFORMATION: Xaa is a hydrophobic amino acid residue
<220> FEATURE:
<221> NAME/KEY: misc_feature
<222> LOCATION: (19)..(19)
<223> OTHER INFORMATION: Xaa is a hydrophilic amino acid residue
<220> FEATURE:
<221> NAME/KEY: misc_feature
<222> LOCATION: (20)..(20)
<223> OTHER INFORMATION: Xaa is a hydrophobic amino acid residue
<220> FEATURE:
<221> NAME/KEY: misc_feature
<222> LOCATION: (21)..(21)
<223> OTHER INFORMATION: Xaa is a hydrophilic amino acid residue
<220> FEATURE:
<221> NAME/KEY: misc_feature
<222> LOCATION: (22)..(22)
<223> OTHER INFORMATION: Xaa is a hydrophobic amino acid residue
<220> FEATURE:
<221> NAME/KEY: misc_feature
<222> LOCATION: (23)..(23)
<223> OTHER INFORMATION: Xaa is a a hydrophilic amino acid residue
<220> FEATURE:
<221> NAME/KEY: misc_feature
<222> LOCATION: (24)..(24)
<223> OTHER INFORMATION: Xaa is a hydrophobic amino acid residue

<400> SEQUENCE: 31

Xaa Xaa Xaa Xaa Xaa Xaa Xaa Gly Gly Cys Xaa Xaa Xaa Xaa Cys Gly
1               5                   10                  15

Gly Xaa Xaa Xaa Xaa Xaa Xaa Xaa
            20

<210> SEQ ID NO 32
<211> LENGTH: 26
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: Xaa is a hydrophobic amino acid residue
<220> FEATURE:
<221> NAME/KEY: misc_feature
<222> LOCATION: (2)..(2)
<223> OTHER INFORMATION: Xaa is a hydrophilic amino acid residue
<220> FEATURE:
<221> NAME/KEY: misc_feature
<222> LOCATION: (3)..(3)
<223> OTHER INFORMATION: Xaa is a hydrophobic amino acid residue
<220> FEATURE:
<221> NAME/KEY: misc_feature
<222> LOCATION: (4)..(4)
<223> OTHER INFORMATION: Xaa is a hydrophilic amino acid residue
<220> FEATURE:
<221> NAME/KEY: misc_feature
```

```
<222> LOCATION: (5)..(5)
<223> OTHER INFORMATION: Xaa is a hydrophobic amino acid residue
<220> FEATURE:
<221> NAME/KEY: misc_feature
<222> LOCATION: (6)..(6)
<223> OTHER INFORMATION: Xaa is a hydrophilic amino acid residue
<220> FEATURE:
<221> NAME/KEY: misc_feature
<222> LOCATION: (7)..(7)
<223> OTHER INFORMATION: Xaa is a hydrophobic amino acid residue
<220> FEATURE:
<221> NAME/KEY: misc_feature
<222> LOCATION: (8)..(8)
<223> OTHER INFORMATION: Xaa is a hydrophilic amino acid residue
<220> FEATURE:
<221> NAME/KEY: misc_feature
<222> LOCATION: (12)..(12)
<223> OTHER INFORMATION: Xaa is a hydrophobic amino acid residue
<220> FEATURE:
<221> NAME/KEY: misc_feature
<222> LOCATION: (13)..(13)
<223> OTHER INFORMATION: Xaa is a hydrophobic amino acid residue
<220> FEATURE:
<221> NAME/KEY: misc_feature
<222> LOCATION: (14)..(14)
<223> OTHER INFORMATION: Xaa is a hydrophilic amino acid residue
<220> FEATURE:
<221> NAME/KEY: misc_feature
<222> LOCATION: (15)..(15)
<223> OTHER INFORMATION: Xaa is a hydrophobic amino acid residue
<220> FEATURE:
<221> NAME/KEY: misc_feature
<222> LOCATION: (19)..(19)
<223> OTHER INFORMATION: Xaa is a hydrophilic amino acid residue
<220> FEATURE:
<221> NAME/KEY: misc_feature
<222> LOCATION: (20)..(20)
<223> OTHER INFORMATION: Xaa is a hydrophobic amino acid residue
<220> FEATURE:
<221> NAME/KEY: misc_feature
<222> LOCATION: (21)..(21)
<223> OTHER INFORMATION: Xaa is a hydrophilic amino acid residue
<220> FEATURE:
<221> NAME/KEY: misc_feature
<222> LOCATION: (22)..(22)
<223> OTHER INFORMATION: Xaa is a hydrophobic amino acid residue
<220> FEATURE:
<221> NAME/KEY: misc_feature
<222> LOCATION: (23)..(23)
<223> OTHER INFORMATION: Xaa is a hydrophilic amino acid residue
<220> FEATURE:
<221> NAME/KEY: misc_feature
<222> LOCATION: (24)..(24)
<223> OTHER INFORMATION: Xaa is a hydrophobic amino acid residue
<220> FEATURE:
<221> NAME/KEY: misc_feature
<222> LOCATION: (25)..(25)
<223> OTHER INFORMATION: Xaa is a hydrophilic amino acid residue
<220> FEATURE:
<221> NAME/KEY: misc_feature
<222> LOCATION: (26)..(26)
<223> OTHER INFORMATION: Xaa is a hydrophobic amino acid residue

<400> SEQUENCE: 32

Xaa Xaa Xaa Xaa Xaa Xaa Xaa Xaa Gly Gly Cys Xaa Xaa Xaa Xaa Cys
1               5                   10                  15

Gly Gly Xaa Xaa Xaa Xaa Xaa Xaa Xaa Xaa
            20                  25

<210> SEQ ID NO 33
<211> LENGTH: 7
<212> TYPE: PRT
<213> ORGANISM: Artificial Sequence
<220> FEATURE:
<223> OTHER INFORMATION: Synthetic sequence
<220> FEATURE:
```

```
<221> NAME/KEY: misc_feature
<222> LOCATION: (2)..(2)
<223> OTHER INFORMATION: Xaa is Ornithine or K
<220> FEATURE:
<221> NAME/KEY: misc_feature
<222> LOCATION: (4)..(4)
<223> OTHER INFORMATION: Xaa is Ornithine or K
<220> FEATURE:
<221> NAME/KEY: misc_feature
<222> LOCATION: (6)..(6)
<223> OTHER INFORMATION: Xaa is Ornithine or R

<400> SEQUENCE: 33

Phe Xaa Ile Xaa Ala Xaa Leu
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (4)..(4)
<223> OTHER INFORMATION: Xaa is Ornithine

<400> SEQUENCE: 34

Phe Lys Ile Xaa Ala Arg Leu
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (2)..(2)
<223> OTHER INFORMATION: Xaa is Ornithine
<220> FEATURE:
<221> NAME/KEY: misc_feature
<222> LOCATION: (4)..(4)
<223> OTHER INFORMATION: Xaa is Ornithine
<220> FEATURE:
<221> NAME/KEY: misc_feature
<222> LOCATION: (6)..(6)
<223> OTHER INFORMATION: Xaa is Ornithine

<400> SEQUENCE: 35

Phe Xaa Ile Xaa Ala Xaa Leu
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (2)..(2)
<223> OTHER INFORMATION: Xaa is Ornithine
<220> FEATURE:
<221> NAME/KEY: misc_feature
<222> LOCATION: (6)..(6)
<223> OTHER INFORMATION: Xaa is Ornithine

<400> SEQUENCE: 36

Phe Xaa Ile Lys Ala Xaa Leu
1               5
```

```
<210> SEQ ID NO 37
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (2)..(2)
<223> OTHER INFORMATION: Xaa is Ornithine or K
<220> FEATURE:
<221> NAME/KEY: misc_feature
<222> LOCATION: (4)..(4)
<223> OTHER INFORMATION: Xaa is Ornithine or R
<220> FEATURE:
<221> NAME/KEY: misc_feature
<222> LOCATION: (6)..(6)
<223> OTHER INFORMATION: Xaa is Ornithine or K

<400> SEQUENCE: 37

Ile Xaa Ala Xaa Leu Xaa Phe
1               5

<210> SEQ ID NO 38
<211> LENGTH: 6
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (2)..(2)
<223> OTHER INFORMATION: Xaa is Ornithine

<400> SEQUENCE: 38

Ile Xaa Ala Arg Leu Lys
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (2)..(2)
<223> OTHER INFORMATION: Xaa is Ornithine
<220> FEATURE:
<221> NAME/KEY: misc_feature
<222> LOCATION: (4)..(4)
<223> OTHER INFORMATION: Xaa is Ornithine
<220> FEATURE:
<221> NAME/KEY: misc_feature
<222> LOCATION: (6)..(6)
<223> OTHER INFORMATION: Xaa is Ornithine

<400> SEQUENCE: 39

Ile Xaa Ala Xaa Leu Xaa Phe
1               5

<210> SEQ ID NO 40
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (4)..(4)
<223> OTHER INFORMATION: Xaa is Ornithine
```

<400> SEQUENCE: 40

Ile Lys Ala Xaa Leu Lys Phe
1               5

<210> SEQ ID NO 41
<211> LENGTH: 6
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (4)..(4)
<223> OTHER INFORMATION: Xaa is Ornithine

<400> SEQUENCE: 41

Cys Leu Gly Xaa Phe Cys
1               5

<210> SEQ ID NO 42
<211> LENGTH: 6
<212> TYPE: PRT
<213> ORGANISM: Artificial Sequence
<220> FEATURE:
<223> OTHER INFORMATION: Synthetic sequence

<400> SEQUENCE: 42

Cys Leu Gly Lys Phe Cys
1               5

<210> SEQ ID NO 43
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (6)..(6)
<223> OTHER INFORMATION: Xaa is Ornithine

<400> SEQUENCE: 43

Gly Gly Cys Leu Gly Xaa Phe Cys
1               5

<210> SEQ ID NO 44
<211> LENGTH: 10
<212> TYPE: PRT
<213> ORGANISM: Artificial Sequence
<220> FEATURE:
<223> OTHER INFORMATION: Synthetic sequence

<400> SEQUENCE: 44

Gly Gly Cys Leu Gly Lys Phe Cys Gly Gly
1               5                   10

<210> SEQ ID NO 45
<211> LENGTH: 9
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: Xaa is a naturally occuring amino acid
<220> FEATURE:
<221> NAME/KEY: misc_feature
<222> LOCATION: (3)..(3)
<223> OTHER INFORMATION: Xaa is a naturally occuring amino acid
<220> FEATURE:
<221> NAME/KEY: misc_feature
<222> LOCATION: (5)..(5)
<223> OTHER INFORMATION: Xaa is a naturally occuring amino acid
<220> FEATURE:
<221> NAME/KEY: misc_feature
<222> LOCATION: (7)..(7)
<223> OTHER INFORMATION: Xaa is a naturally occuring amino acid
<220> FEATURE:
<221> NAME/KEY: misc_feature
<222> LOCATION: (9)..(9)
<223> OTHER INFORMATION: Xaa is a naturally occuring amino acid

<400> SEQUENCE: 45

Xaa Cys Xaa Cys Xaa Cys Xaa Cys Xaa
1               5

<210> SEQ ID NO 46
<211> LENGTH: 17
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: Xaa is a hydrophilic amino acid residue
<220> FEATURE:
<221> NAME/KEY: misc_feature
<222> LOCATION: (2)..(2)
<223> OTHER INFORMATION: Xaa is a hydrophobic amino acid residue
<220> FEATURE:
<221> NAME/KEY: misc_feature
<222> LOCATION: (4)..(4)
<223> OTHER INFORMATION: Xaa is a hydrophobic amino acid residue
<220> FEATURE:
<221> NAME/KEY: misc_feature
<222> LOCATION: (5)..(5)
<223> OTHER INFORMATION: Xaa is a hydrophilic amino acid residue
<220> FEATURE:
<221> NAME/KEY: misc_feature
<222> LOCATION: (6)..(6)
<223> OTHER INFORMATION: Xaa is a hydrophobic amino acid residue
<220> FEATURE:
<221> NAME/KEY: misc_feature
<222> LOCATION: (8)..(8)
<223> OTHER INFORMATION: Xaa is a hydrophobic amino acid residue
<220> FEATURE:
<221> NAME/KEY: misc_feature
<222> LOCATION: (9)..(9)
<223> OTHER INFORMATION: Xaa is a hydrophilic amino acid residue
<220> FEATURE:
<221> NAME/KEY: misc_feature
<222> LOCATION: (10)..(10)
<223> OTHER INFORMATION: Xaa is a hydrophobic amino acid residue
<220> FEATURE:
<221> NAME/KEY: misc_feature
<222> LOCATION: (11)..(11)
<223> OTHER INFORMATION: Xaa is a hydrophobic amino acid residue
<220> FEATURE:
<221> NAME/KEY: misc_feature
<222> LOCATION: (13)..(13)
<223> OTHER INFORMATION: Xaa is a hydrophobic amino acid residue
<220> FEATURE:
<221> NAME/KEY: misc_feature
<222> LOCATION: (14)..(14)
<223> OTHER INFORMATION: Xaa is a hydrophilic amino acid residue
<220> FEATURE:
<221> NAME/KEY: misc_feature
<222> LOCATION: (15)..(15)
<223> OTHER INFORMATION: Xaa is a hydrophilic amino acid residue
<220> FEATURE:
<221> NAME/KEY: misc_feature
<222> LOCATION: (17)..(17)
<223> OTHER INFORMATION: Xaa is a hydrophilic amino acid residue -continued

<400> SEQUENCE: 46

Xaa Xaa Cys Xaa Xaa Xaa Cys Xaa Xaa Xaa Xaa Cys Xaa Xaa Xaa Cys
1               5                   10                  15

Xaa

<210> SEQ ID NO 47
<211> LENGTH: 17
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: Xaa is Ornithine or R
<220> FEATURE:
<221> NAME/KEY: misc_feature
<222> LOCATION: (2)..(2)
<223> OTHER INFORMATION: Xaa is F or W
<220> FEATURE:
<221> NAME/KEY: misc_feature
<222> LOCATION: (4)..(4)
<223> OTHER INFORMATION: Xaa is F or W
<220> FEATURE:
<221> NAME/KEY: misc_feature
<222> LOCATION: (5)..(5)
<223> OTHER INFORMATION: Xaa is Ornithine or K
<220> FEATURE:
<221> NAME/KEY: misc_feature
<222> LOCATION: (9)..(9)
<223> OTHER INFORMATION: Xaa is Ornithine or K
<220> FEATURE:
<221> NAME/KEY: misc_feature
<222> LOCATION: (13)..(13)
<223> OTHER INFORMATION: Xaa is F or W
<220> FEATURE:
<221> NAME/KEY: misc_feature
<222> LOCATION: (14)..(14)
<223> OTHER INFORMATION: Xaa is Ornithine or K
<220> FEATURE:
<221> NAME/KEY: misc_feature
<222> LOCATION: (15)..(15)
<223> OTHER INFORMATION: Xaa is Ornithine or K
<220> FEATURE:
<221> NAME/KEY: misc_feature
<222> LOCATION: (17)..(17)
<223> OTHER INFORMATION: Xaa is Ornithine or K

<400> SEQUENCE: 47

Xaa Xaa Cys Xaa Xaa Val Cys Tyr Xaa Gly Ile Cys Xaa Xaa Xaa Cys
1               5                   10                  15

Xaa

<210> SEQ ID NO 48
<211> LENGTH: 17
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: Xaa is a hydrophilic amino acid residue
<220> FEATURE:
<221> NAME/KEY: misc_feature
<222> LOCATION: (3)..(3)
<223> OTHER INFORMATION: Xaa is a hydrophilic amino acid residue
<220> FEATURE:
<221> NAME/KEY: misc_feature
<222> LOCATION: (4)..(4)
<223> OTHER INFORMATION: Xaa is a hydrophilic amino acid residue
<220> FEATURE:

```
<221> NAME/KEY: misc_feature
<222> LOCATION: (5)..(5)
<223> OTHER INFORMATION: Xaa is a hydrophobic amino acid residue
<220> FEATURE:
<221> NAME/KEY: misc_feature
<222> LOCATION: (7)..(7)
<223> OTHER INFORMATION: Xaa is a hydrophobic amino acid residue
<220> FEATURE:
<221> NAME/KEY: misc_feature
<222> LOCATION: (8)..(8)
<223> OTHER INFORMATION: Xaa is a hydrophobic amino acid residue
<220> FEATURE:
<221> NAME/KEY: misc_feature
<222> LOCATION: (9)..(9)
<223> OTHER INFORMATION: Xaa is a hydrophilic amino acid residue
<220> FEATURE:
<221> NAME/KEY: misc_feature
<222> LOCATION: (10)..(10)
<223> OTHER INFORMATION: Xaa is a hydrophobic amino acid residue
<220> FEATURE:
<221> NAME/KEY: misc_feature
<222> LOCATION: (12)..(12)
<223> OTHER INFORMATION: Xaa is a hydrophobic amino acid residue
<220> FEATURE:
<221> NAME/KEY: misc_feature
<222> LOCATION: (13)..(13)
<223> OTHER INFORMATION: Xaa is a hydrophilic amino acid residue
<220> FEATURE:
<221> NAME/KEY: misc_feature
<222> LOCATION: (14)..(14)
<223> OTHER INFORMATION: Xaa is a hydrophobic amino acid residue
<220> FEATURE:
<221> NAME/KEY: misc_feature
<222> LOCATION: (16)..(16)
<223> OTHER INFORMATION: Xaa is a hydrophobic amino acid residue
<220> FEATURE:
<221> NAME/KEY: misc_feature
<222> LOCATION: (17)..(17)
<223> OTHER INFORMATION: Xaa is a hydrophilic amino acid residue

<400> SEQUENCE: 48

Xaa Cys Xaa Xaa Xaa Cys Xaa Xaa Xaa Cys Xaa Xaa Xaa Cys Xaa
1               5                   10                  15

Xaa

<210> SEQ ID NO 49
<211> LENGTH: 17
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: Xaa is a Ornithine or R
<220> FEATURE:
<221> NAME/KEY: misc_feature
<222> LOCATION: (3)..(3)
<223> OTHER INFORMATION: Xaa is a Ornithine or R
<220> FEATURE:
<221> NAME/KEY: misc_feature
<222> LOCATION: (4)..(4)
<223> OTHER INFORMATION: Xaa is a Ornithine or R
<220> FEATURE:
<221> NAME/KEY: misc_feature
<222> LOCATION: (5)..(5)
<223> OTHER INFORMATION: Xaa is Y or F
<220> FEATURE:
<221> NAME/KEY: misc_feature
<222> LOCATION: (9)..(9)
<223> OTHER INFORMATION: Xaa is a Ornithine or R
<220> FEATURE:
<221> NAME/KEY: misc_feature
<222> LOCATION: (13)..(13)
<223> OTHER INFORMATION: Xaa is a Ornithine or R
<220> FEATURE:
```

```
<221> NAME/KEY: misc_feature
<222> LOCATION: (14)..(14)
<223> OTHER INFORMATION: Xaa is F or W
<220> FEATURE:
<221> NAME/KEY: misc_feature
<222> LOCATION: (16)..(16)
<223> OTHER INFORMATION: Xaa is F or W
<220> FEATURE:
<221> NAME/KEY: misc_feature
<222> LOCATION: (17)..(17)
<223> OTHER INFORMATION: Xaa is Ornithine or K

<400> SEQUENCE: 49

Xaa Cys Xaa Xaa Xaa Cys Ile Gly Xaa Tyr Cys Val Xaa Xaa Cys Xaa
1               5                   10                  15

Xaa

<210> SEQ ID NO 50
<211> LENGTH: 18
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: Xaa is a hydrophilic amino acid residue
<220> FEATURE:
<221> NAME/KEY: misc_feature
<222> LOCATION: (2)..(2)
<223> OTHER INFORMATION: Xaa is a hydrophobic amino acid residue
<220> FEATURE:
<221> NAME/KEY: misc_feature
<222> LOCATION: (3)..(3)
<223> OTHER INFORMATION: Xaa is a hydrophobic amino acid residue
<220> FEATURE:
<221> NAME/KEY: misc_feature
<222> LOCATION: (5)..(5)
<223> OTHER INFORMATION: Xaa is a hydrophobic amino acid residue
<220> FEATURE:
<221> NAME/KEY: misc_feature
<222> LOCATION: (7)..(7)
<223> OTHER INFORMATION: Xaa is a hydrophobic amino acid residue
<220> FEATURE:
<221> NAME/KEY: misc_feature
<222> LOCATION: (8)..(8)
<223> OTHER INFORMATION: Xaa is a hydrophilic amino acid residue
<220> FEATURE:
<221> NAME/KEY: misc_feature
<222> LOCATION: (9)..(9)
<223> OTHER INFORMATION: Xaa is a hydrophilic amino acid residue
<220> FEATURE:
<221> NAME/KEY: misc_feature
<222> LOCATION: (10)..(10)
<223> OTHER INFORMATION: Xaa is a hydrophilic amino acid residue
<220> FEATURE:
<221> NAME/KEY: misc_feature
<222> LOCATION: (12)..(12)
<223> OTHER INFORMATION: Xaa is a hydrophobic amino acid residue
<220> FEATURE:
<221> NAME/KEY: misc_feature
<222> LOCATION: (14)..(14)
<223> OTHER INFORMATION: Xaa is a hydrophobic amino acid residue
<220> FEATURE:
<221> NAME/KEY: misc_feature
<222> LOCATION: (15)..(15)
<223> OTHER INFORMATION: Xaa is a hydrophilic amino acid residue
<220> FEATURE:
<221> NAME/KEY: misc_feature
<222> LOCATION: (16)..(16)
<223> OTHER INFORMATION: Xaa is a hydrophobic amino acid residue
<220> FEATURE:
<221> NAME/KEY: misc_feature
<222> LOCATION: (17)..(17)
<223> OTHER INFORMATION: Xaa is a hydrophobic amino acid residue
<220> FEATURE:
```

```
<221> NAME/KEY: misc_feature
<222> LOCATION: (18)..(18)
<223> OTHER INFORMATION: Xaa is a hydrophilic amino acid residue

<400> SEQUENCE: 50

Xaa Xaa Xaa Cys Xaa Cys Xaa Xaa Xaa Xaa Cys Xaa Cys Xaa Xaa Xaa
1               5                   10                  15

Xaa Xaa

<210> SEQ ID NO 51
<211> LENGTH: 6
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (3)..(3)
<223> OTHER INFORMATION: Xaa is Ornithine

<400> SEQUENCE: 51

Cys Tyr Xaa Gly Ile Cys
1               5

<210> SEQ ID NO 52
<211> LENGTH: 6
<212> TYPE: PRT
<213> ORGANISM: Artificial Sequence
<220> FEATURE:
<223> OTHER INFORMATION: Synthetic sequence

<400> SEQUENCE: 52

Cys Ile Gly Arg Tyr Cys
1               5

<210> SEQ ID NO 53
<211> LENGTH: 6
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (4)..(4)
<223> OTHER INFORMATION: Xaa is Ornithine

<400> SEQUENCE: 53

Cys Ile Gly Xaa Tyr Cys
1               5

<210> SEQ ID NO 54
<211> LENGTH: 6
<212> TYPE: PRT
<213> ORGANISM: Artificial Sequence
<220> FEATURE:
<223> OTHER INFORMATION: Synthetic sequence

<400> SEQUENCE: 54

Cys Phe Arg Arg Arg Cys
1               5

<210> SEQ ID NO 55
<211> LENGTH: 18
<212> TYPE: PRT
<213> ORGANISM: Artificial Sequence
<220> FEATURE:
<223> OTHER INFORMATION: Synthetic sequence
<220> FEATURE:
```

```
<221> NAME/KEY: misc_feature
<222> LOCATION: (3)..(3)
<223> OTHER INFORMATION: Xaa is Ornithine
<220> FEATURE:
<221> NAME/KEY: misc_feature
<222> LOCATION: (8)..(8)
<223> OTHER INFORMATION: Xaa is Ornithine
<220> FEATURE:
<221> NAME/KEY: misc_feature
<222> LOCATION: (11)..(11)
<223> OTHER INFORMATION: Xaa is Ornithine
<220> FEATURE:
<221> NAME/KEY: misc_feature
<222> LOCATION: (14)..(14)
<223> OTHER INFORMATION: Xaa is Ornithine

<400> SEQUENCE: 55

Phe Ile Xaa Lys Phe Ala Lys Xaa Phe Lys Xaa Phe Ile Xaa Lys Phe
1               5                   10                  15

Ala Lys

<210> SEQ ID NO 56
<211> LENGTH: 18
<212> TYPE: PRT
<213> ORGANISM: Artificial Sequence
<220> FEATURE:
<223> OTHER INFORMATION: Synthetic sequence

<400> SEQUENCE: 56

Arg Val Phe Lys Lys Ala Phe Arg Lys Phe Lys Lys Leu Phe Lys Arg
1               5                   10                  15

Ala Phe

<210> SEQ ID NO 57
<211> LENGTH: 18
<212> TYPE: PRT
<213> ORGANISM: Artificial Sequence
<220> FEATURE:
<223> OTHER INFORMATION: Synthetic sequence

<400> SEQUENCE: 57

Phe Ala Arg Lys Phe Leu Lys Lys Phe Lys Arg Phe Ala Lys Lys Phe
1               5                   10                  15

Val Arg

<210> SEQ ID NO 58
<211> LENGTH: 18
<212> TYPE: PRT
<213> ORGANISM: Artificial Sequence
<220> FEATURE:
<223> OTHER INFORMATION: Synthetic sequence

<400> SEQUENCE: 58

Phe Lys Arg Lys Ile Lys Ala Lys Leu Arg Phe Lys Ala Lys Val Arg
1               5                   10                  15

Leu Lys

<210> SEQ ID NO 59
<211> LENGTH: 23
<212> TYPE: PRT
<213> ORGANISM: Artificial Sequence
<220> FEATURE:
<223> OTHER INFORMATION: Synthetic sequence

<400> SEQUENCE: 59

Phe Ala Phe Ala Phe Arg Val Phe Lys Lys Ala Phe Arg Lys Phe Lys
```

```
1               5                   10                  15

Lys Leu Phe Lys Arg Ala Phe
            20

<210> SEQ ID NO 60
<211> LENGTH: 23
<212> TYPE: PRT
<213> ORGANISM: Artificial Sequence
<220> FEATURE:
<223> OTHER INFORMATION: Synthetic sequence

<400> SEQUENCE: 60

Phe Ala Arg Lys Phe Leu Lys Lys Phe Lys Arg Phe Ala Lys Lys Phe
1               5                   10                  15

Val Arg Phe Ala Phe Ala Phe
            20

<210> SEQ ID NO 61
<211> LENGTH: 18
<212> TYPE: PRT
<213> ORGANISM: Artificial Sequence
<220> FEATURE:
<223> OTHER INFORMATION: Synthetic sequence

<400> SEQUENCE: 61

Lys Ile Arg Ala Lys Leu Cys Leu Gly Arg Phe Cys Ile Arg Ala Lys
1               5                   10                  15

Leu Arg

<210> SEQ ID NO 62
<211> LENGTH: 18
<212> TYPE: PRT
<213> ORGANISM: Artificial Sequence
<220> FEATURE:
<223> OTHER INFORMATION: Synthetic sequence

<400> SEQUENCE: 62

Lys Ile Lys Ala Arg Leu Cys Leu Gly Lys Phe Cys Ile Lys Ala Arg
1               5                   10                  15

Leu Lys

<210> SEQ ID NO 63
<211> LENGTH: 50
<212> TYPE: PRT
<213> ORGANISM: Artificial Sequence
<220> FEATURE:
<223> OTHER INFORMATION: Synthetic sequence

<400> SEQUENCE: 63

Phe Ala Phe Ala Phe Lys Ala Phe Lys Lys Phe Lys Phe Lys
1               5                   10                  15

Lys Ala Phe Lys Lys Ala Phe Gly Pro Gly Arg Phe Ala Lys Lys Phe
                20                  25                  30

Ala Lys Lys Phe Lys Lys Phe Ala Lys Lys Phe Ala Lys Phe Ala Phe
                35                  40                  45

Ala Phe
        50

<210> SEQ ID NO 64
<211> LENGTH: 50
<212> TYPE: PRT
<213> ORGANISM: Artificial Sequence
<220> FEATURE:
```

<223> OTHER INFORMATION: Synthetic sequence

<400> SEQUENCE: 64

Phe Ala Lys Lys Phe Ala Lys Lys Phe Lys Lys Phe Ala Lys Lys Phe
1               5                   10                  15
Ala Lys Phe Ala Phe Ala Phe Gly Pro Gly Arg Phe Ala Phe Ala Phe
            20                  25                  30
Lys Ala Phe Lys Lys Ala Phe Lys Lys Phe Lys Lys Ala Phe Lys Lys
        35                  40                  45
Ala Phe
    50

<210> SEQ ID NO 65
<211> LENGTH: 19
<212> TYPE: PRT
<213> ORGANISM: Artificial Sequence
<220> FEATURE:
<223> OTHER INFORMATION: Synthetic sequence

<400> SEQUENCE: 65

Met Gly Phe Lys Leu Arg Ala Lys Ile Lys Val Arg Leu Arg Ala Lys
1               5                   10                  15
Ile Lys Leu

<210> SEQ ID NO 66
<211> LENGTH: 12
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (3)..(3)
<223> OTHER INFORMATION: Xaa is Ornithine
<220> FEATURE:
<221> NAME/KEY: misc_feature
<222> LOCATION: (8)..(8)
<223> OTHER INFORMATION: Xaa is Ornithine

<400> SEQUENCE: 66

Cys Val Xaa Leu Phe Pro Val Xaa Leu Phe Pro Cys
1               5                   10

<210> SEQ ID NO 67
<211> LENGTH: 16
<212> TYPE: PRT
<213> ORGANISM: Artificial Sequence
<220> FEATURE:
<223> OTHER INFORMATION: Synthetic sequence

<400> SEQUENCE: 67

Cys Lys Leu Arg Phe Arg Gly Pro Gly Arg Ile Lys Val Arg Leu Cys
1               5                   10                  15

<210> SEQ ID NO 68
<211> LENGTH: 26
<212> TYPE: PRT
<213> ORGANISM: Artificial Sequence
<220> FEATURE:
<223> OTHER INFORMATION: Synthetic sequence

<400> SEQUENCE: 68

Cys Pro Gly Phe Ala Lys Lys Phe Ala Lys Lys Phe Lys Lys Phe Ala
1               5                   10                  15
Lys Lys Phe Ala Lys Phe Ala Phe Ala Phe

```
                      20                  25

<210> SEQ ID NO 69
<211> LENGTH: 18
<212> TYPE: PRT
<213> ORGANISM: Artificial Sequence
<220> FEATURE:
<223> OTHER INFORMATION: Synthetic sequence

<400> SEQUENCE: 69

Lys Ile Arg Ala Lys Leu Cys Leu Gly Arg Phe Cys Ile Arg Ala Lys
1               5                   10                  15

Leu Arg

<210> SEQ ID NO 70
<211> LENGTH: 26
<212> TYPE: PRT
<213> ORGANISM: Artificial Sequence
<220> FEATURE:
<223> OTHER INFORMATION: Synthetic sequence

<400> SEQUENCE: 70

Lys Lys Lys Pro Lys Pro Pro Tyr Leu Pro Lys Pro Lys Pro Pro Pro
1               5                   10                  15

Phe Phe Pro Pro Lys Leu Pro Pro Lys Ile
                20                  25

<210> SEQ ID NO 71
<211> LENGTH: 26
<212> TYPE: PRT
<213> ORGANISM: Artificial Sequence
<220> FEATURE:
<223> OTHER INFORMATION: Synthetic sequence

<400> SEQUENCE: 71

Phe Ala Phe Ala Phe Lys Ala Phe Lys Lys Ala Phe Lys Lys Phe Lys
1               5                   10                  15

Lys Ala Phe Lys Lys Ala Phe Gly Pro Cys
                20                  25

<210> SEQ ID NO 72
<211> LENGTH: 22
<212> TYPE: PRT
<213> ORGANISM: Artificial Sequence
<220> FEATURE:
<223> OTHER INFORMATION: Synthetic sequence

<400> SEQUENCE: 72

Phe Ala Phe Ala Phe Ala Phe Lys Lys Ala Phe Lys Lys Phe Lys Lys
1               5                   10                  15

Ala Phe Lys Lys Ala Phe
                20

<210> SEQ ID NO 73
<211> LENGTH: 23
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (6)..(6)
<223> OTHER INFORMATION: Xaa is Ornithine
<220> FEATURE:
<221> NAME/KEY: misc_feature
<222> LOCATION: (9)..(10)
```

```
<223> OTHER INFORMATION: Xaa is Ornithine
<220> FEATURE:
<221> NAME/KEY: misc_feature
<222> LOCATION: (13)..(13)
<223> OTHER INFORMATION: Xaa is Ornithine
<220> FEATURE:
<221> NAME/KEY: misc_feature
<222> LOCATION: (14)..(14)
<223> OTHER INFORMATION: Xaa is Ornithine
<220> FEATURE:
<221> NAME/KEY: misc_feature
<222> LOCATION: (16)..(16)
<223> OTHER INFORMATION: Xaa is Ornithine
<220> FEATURE:
<221> NAME/KEY: misc_feature
<222> LOCATION: (17)..(17)
<223> OTHER INFORMATION: Xaa is Ornithine
<220> FEATURE:
<221> NAME/KEY: misc_feature
<222> LOCATION: (20)..(20)
<223> OTHER INFORMATION: Xaa is Ornithine
<220> FEATURE:
<221> NAME/KEY: misc_feature
<222> LOCATION: (21)..(21)
<223> OTHER INFORMATION: Xaa is Ornithine

<400> SEQUENCE: 73

Phe Ala Phe Ala Phe Xaa Ala Phe Xaa Xaa Ala Phe Xaa Xaa Phe Xaa
1               5                   10                  15

Xaa Ala Phe Xaa Xaa Ala Phe
            20

<210> SEQ ID NO 74
<211> LENGTH: 23
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (3)..(3)
<223> OTHER INFORMATION: Xaa is Ornithine
<220> FEATURE:
<221> NAME/KEY: misc_feature
<222> LOCATION: (4)..(4)
<223> OTHER INFORMATION: Xaa is Ornithine
<220> FEATURE:
<221> NAME/KEY: misc_feature
<222> LOCATION: (7)..(7)
<223> OTHER INFORMATION: Xaa is Ornithine
<220> FEATURE:
<221> NAME/KEY: misc_feature
<222> LOCATION: (8)..(8)
<223> OTHER INFORMATION: Xaa is Ornithine
<220> FEATURE:
<221> NAME/KEY: misc_feature
<222> LOCATION: (10)..(10)
<223> OTHER INFORMATION: Xaa is Ornithine
<220> FEATURE:
<221> NAME/KEY: misc_feature
<222> LOCATION: (11)..(11)
<223> OTHER INFORMATION: Xaa is Ornithine
<220> FEATURE:
<221> NAME/KEY: misc_feature
<222> LOCATION: (14)..(14)
<223> OTHER INFORMATION: Xaa is Ornithine
<220> FEATURE:
<221> NAME/KEY: misc_feature
<222> LOCATION: (15)..(15)
<223> OTHER INFORMATION: Xaa is Ornithine
<220> FEATURE:
<221> NAME/KEY: misc_feature
<222> LOCATION: (18)..(18)
<223> OTHER INFORMATION: Xaa is Ornithine

<400> SEQUENCE: 74
```

-continued

Phe Ala Xaa Xaa Phe Ala Xaa Xaa Phe Xaa Xaa Phe Ala Xaa Xaa Phe
1               5                   10                  15

Ala Xaa Phe Ala Phe Ala Phe
            20

<210> SEQ ID NO 75
<211> LENGTH: 22
<212> TYPE: PRT
<213> ORGANISM: Artificial Sequence
<220> FEATURE:
<223> OTHER INFORMATION: Synthetic sequence

<400> SEQUENCE: 75

Phe Ala Lys Lys Phe Ala Lys Lys Phe Lys Lys Phe Ala Lys Lys Phe
1               5                   10                  15

Ala Phe Ala Phe Ala Phe
            20

<210> SEQ ID NO 76
<211> LENGTH: 31
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (11)..(11)
<223> OTHER INFORMATION: Xaa is Ornithine
<220> FEATURE:
<221> NAME/KEY: misc_feature
<222> LOCATION: (12)..(12)
<223> OTHER INFORMATION: Xaa is Ornithine
<220> FEATURE:
<221> NAME/KEY: misc_feature
<222> LOCATION: (15)..(15)
<223> OTHER INFORMATION: Xaa is Ornithine
<220> FEATURE:
<221> NAME/KEY: misc_feature
<222> LOCATION: (16)..(16)
<223> OTHER INFORMATION: Xaa is Ornithine
<220> FEATURE:
<221> NAME/KEY: misc_feature
<222> LOCATION: (18)..(18)
<223> OTHER INFORMATION: Xaa is Ornithine
<220> FEATURE:
<221> NAME/KEY: misc_feature
<222> LOCATION: (19)..(19)
<223> OTHER INFORMATION: Xaa is Ornithine
<220> FEATURE:
<221> NAME/KEY: misc_feature
<222> LOCATION: (22)..(22)
<223> OTHER INFORMATION: Xaa is Ornithine
<220> FEATURE:
<221> NAME/KEY: misc_feature
<222> LOCATION: (23)..(23)
<223> OTHER INFORMATION: Xaa is Ornithine
<220> FEATURE:
<221> NAME/KEY: misc_feature
<222> LOCATION: (26)..(26)
<223> OTHER INFORMATION: Xaa is Ornithine

<400> SEQUENCE: 76

Arg Leu Ala Arg Ile Val Gly Gly Phe Ala Xaa Xaa Phe Ala Xaa Xaa
1               5                   10                  15

Phe Xaa Xaa Phe Ala Xaa Xaa Phe Ala Xaa Phe Ala Phe Ala Phe
            20                  25                  30

<210> SEQ ID NO 77
<211> LENGTH: 33
<212> TYPE: PRT

```
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (13)..(13)
<223> OTHER INFORMATION: Xaa is Ornithine
<220> FEATURE:
<221> NAME/KEY: misc_feature
<222> LOCATION: (14)..(14)
<223> OTHER INFORMATION: Xaa is Ornithine
<220> FEATURE:
<221> NAME/KEY: misc_feature
<222> LOCATION: (17)..(17)
<223> OTHER INFORMATION: Xaa is Ornithine
<220> FEATURE:
<221> NAME/KEY: misc_feature
<222> LOCATION: (18)..(18)
<223> OTHER INFORMATION: Xaa is Ornithine
<220> FEATURE:
<221> NAME/KEY: misc_feature
<222> LOCATION: (20)..(20)
<223> OTHER INFORMATION: Xaa is Ornithine
<220> FEATURE:
<221> NAME/KEY: misc_feature
<222> LOCATION: (21)..(21)
<223> OTHER INFORMATION: Xaa is Ornithine
<220> FEATURE:
<221> NAME/KEY: misc_feature
<222> LOCATION: (24)..(24)
<223> OTHER INFORMATION: Xaa is Ornithine
<220> FEATURE:
<221> NAME/KEY: misc_feature
<222> LOCATION: (25)..(25)
<223> OTHER INFORMATION: Xaa is Ornithine
<220> FEATURE:
<221> NAME/KEY: misc_feature
<222> LOCATION: (28)..(28)
<223> OTHER INFORMATION: Xaa is Ornithine

<400> SEQUENCE: 77

Cys Arg Leu Ala Arg Ile Val Cys Gly Gly Phe Ala Xaa Xaa Phe Ala
 1               5                  10                  15

Xaa Xaa Phe Xaa Xaa Phe Ala Xaa Xaa Phe Ala Xaa Phe Ala Phe Ala
            20                  25                  30

Phe

<210> SEQ ID NO 78
<211> LENGTH: 24
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (2)..(2)
<223> OTHER INFORMATION: Xaa is Ornithine
<220> FEATURE:
<221> NAME/KEY: misc_feature
<222> LOCATION: (4)..(4)
<223> OTHER INFORMATION: Xaa is Ornithine
<220> FEATURE:
<221> NAME/KEY: misc_feature
<222> LOCATION: (6)..(6)
<223> OTHER INFORMATION: Xaa is Ornithine
<220> FEATURE:
<221> NAME/KEY: misc_feature
<222> LOCATION: (13)..(13)
<223> OTHER INFORMATION: Xaa is Ornithine
<220> FEATURE:
<221> NAME/KEY: misc_feature
<222> LOCATION: (19)..(19)
<223> OTHER INFORMATION: Xaa is Ornithine
<220> FEATURE:
<221> NAME/KEY: misc_feature
```

```
<222> LOCATION: (21)..(21)
<223> OTHER INFORMATION: Xaa is Ornithine
<220> FEATURE:
<221> NAME/KEY: misc_feature
<222> LOCATION: (23)..(23)
<223> OTHER INFORMATION: Xaa is Ornithine

<400> SEQUENCE: 78

Phe Xaa Ile Xaa Ala Xaa Leu Gly Gly Cys Leu Gly Xaa Phe Cys Gly
1               5                   10                  15

Gly Ile Xaa Ala Xaa Leu Xaa Phe
            20

<210> SEQ ID NO 79
<211> LENGTH: 26
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: Xaa is Ornithine
<220> FEATURE:
<221> NAME/KEY: misc_feature
<222> LOCATION: (3)..(3)
<223> OTHER INFORMATION: Xaa is Ornithine
<220> FEATURE:
<221> NAME/KEY: misc_feature
<222> LOCATION: (11)..(11)
<223> OTHER INFORMATION: Xaa is Ornithine
<220> FEATURE:
<221> NAME/KEY: misc_feature
<222> LOCATION: (13)..(13)
<223> OTHER INFORMATION: Xaa is Ornithine
<220> FEATURE:
<221> NAME/KEY: misc_feature
<222> LOCATION: (14)..(14)
<223> OTHER INFORMATION: Xaa is Ornithine
<220> FEATURE:
<221> NAME/KEY: misc_feature
<222> LOCATION: (15)..(15)
<223> OTHER INFORMATION: Xaa is Ornithine
<220> FEATURE:
<221> NAME/KEY: misc_feature
<222> LOCATION: (16)..(16)
<223> OTHER INFORMATION: Xaa is Ornithine
<220> FEATURE:
<221> NAME/KEY: misc_feature
<222> LOCATION: (18)..(18)
<223> OTHER INFORMATION: Xaa is Ornithine
<220> FEATURE:
<221> NAME/KEY: misc_feature
<222> LOCATION: (20)..(20)
<223> OTHER INFORMATION: Xaa is Ornithine
<220> FEATURE:
<221> NAME/KEY: misc_feature
<222> LOCATION: (21)..(21)
<223> OTHER INFORMATION: Xaa is Ornithine
<220> FEATURE:
<221> NAME/KEY: misc_feature
<222> LOCATION: (22)..(22)
<223> OTHER INFORMATION: Xaa is Ornithine
<220> FEATURE:
<221> NAME/KEY: misc_feature
<222> LOCATION: (26)..(26)
<223> OTHER INFORMATION: Xaa is Ornithine

<400> SEQUENCE: 79

Xaa Leu Xaa Ser Leu Leu Lys Thr Leu Ser Xaa Ala Xaa Xaa Xaa Xaa
1               5                   10                  15

Leu Xaa Thr Xaa Xaa Xaa Ala Ile Ser Xaa
            20                  25
```

```
<210> SEQ ID NO 80
<211> LENGTH: 27
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (7)..(7)
<223> OTHER INFORMATION: Xaa is Ornithine
<220> FEATURE:
<221> NAME/KEY: misc_feature
<222> LOCATION: (8)..(8)
<223> OTHER INFORMATION: Xaa is Ornithine
<220> FEATURE:
<221> NAME/KEY: misc_feature
<222> LOCATION: (9)..(9)
<223> OTHER INFORMATION: Xaa is Ornithine
<220> FEATURE:
<221> NAME/KEY: misc_feature
<222> LOCATION: (12)..(12)
<223> OTHER INFORMATION: Xaa is Ornithine
<220> FEATURE:
<221> NAME/KEY: misc_feature
<222> LOCATION: (14)..(14)
<223> OTHER INFORMATION: Xaa is Ornithine
<220> FEATURE:
<221> NAME/KEY: misc_feature
<222> LOCATION: (16)..(16)
<223> OTHER INFORMATION: Xaa is Ornithine

<400> SEQUENCE: 80

Ala Leu Trp Met Thr Leu Xaa Xaa Xaa Val Leu Xaa Ala Xaa Ala Xaa
1               5                   10                  15

Ala Leu Asn Ala Val Leu Val Gly Ala Asn Ala
            20                  25

<210> SEQ ID NO 81
<211> LENGTH: 27
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (7)..(7)
<223> OTHER INFORMATION: Xaa is Ornithine
<220> FEATURE:
<221> NAME/KEY: misc_feature
<222> LOCATION: (8)..(8)
<223> OTHER INFORMATION: Xaa is Ornithine
<220> FEATURE:
<221> NAME/KEY: misc_feature
<222> LOCATION: (9)..(9)
<223> OTHER INFORMATION: Xaa is Ornithine
<220> FEATURE:
<221> NAME/KEY: misc_feature
<222> LOCATION: (12)..(12)
<223> OTHER INFORMATION: Xaa is Ornithine
<220> FEATURE:
<221> NAME/KEY: misc_feature
<222> LOCATION: (14)..(14)
<223> OTHER INFORMATION: Xaa is Ornithine
<220> FEATURE:
<221> NAME/KEY: misc_feature
<222> LOCATION: (16)..(16)
<223> OTHER INFORMATION: Xaa is Ornithine

<400> SEQUENCE: 81

Ala Phe Ala Phe Thr Ala Xaa Xaa Xaa Phe Ala Xaa Phe Xaa Ala Xaa
1               5                   10                  15

Phe Ala Asn Phe Ala Phe Ala Gly Phe Asn Ala
            20                  25
```

UNITED STATES PATENT AND TRADEMARK OFFICE
CERTIFICATE OF CORRECTION

| | | |
|---|---|---|
| PATENT NO. | : 10,548,944 B1 | Page 1 of 1 |
| APPLICATION NO. | : 16/165727 | |
| DATED | : February 4, 2020 | |
| INVENTOR(S) | : Jesse Jaynes et al. | |

It is certified that error appears in the above-identified patent and that said Letters Patent is hereby corrected as shown below:

In the Specification

Column 1, Line 8 Please replace "contract DM140274" with -- contract W81XWH-15-1-0616 --.

Signed and Sealed this
Twenty-sixth Day of October, 2021

Drew Hirshfeld
*Performing the Functions and Duties of the*
*Under Secretary of Commerce for Intellectual Property and*
*Director of the United States Patent and Trademark Office*